(12) United States Patent
Chee et al.

(10) Patent No.: US 7,147,633 B2
(45) Date of Patent: Dec. 12, 2006

(54) METHOD AND APPARATUS FOR TREATMENT OF ATRIAL FIBRILLATION

(75) Inventors: U. Hiram Chee, Santa Cruz, CA (US); Richard L. Mueller, Byron, CA (US); James R. Kermode, Los Altos, CA (US); Curtis P. Tom, San Mateo, CA (US); Douglas Murphy-Chutorian, Palo Alto, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 501 days.

(21) Appl. No.: 10/099,528

(22) Filed: Mar. 14, 2002

(65) Prior Publication Data

US 2002/0183738 A1 Dec. 5, 2002

Related U.S. Application Data

(60) Provisional application No. 60/340,980, filed on Dec. 7, 2001, provisional application No. 60/327,053, filed on Oct. 3, 2001, provisional application No. 60/275,923, filed on Mar. 14, 2001, provisional application No. 60/137,265, filed on Jun. 2, 1999.

(51) Int. Cl.
*A61B 18/18* (2006.01)
(52) U.S. Cl. .............................. 606/41; 606/48; 606/49; 606/51; 606/52; 607/101; 607/104
(58) Field of Classification Search ................ 606/41, 606/54–47, 45–52; 607/115, 116, 122, 101, 607/104, 105, 113, 119
See application file for complete search history.

(56) References Cited

U.S. PATENT DOCUMENTS

| 1,846,596 A | 2/1932 | Hertzberg |
| 2,491,978 A | 12/1949 | Helfman et al. |
| 2,699,166 A | 1/1955 | Dickinson, Jr. et al. |
| 3,057,349 A | 10/1962 | Ismach |
| 3,424,154 A | 1/1969 | Kinsley |
| 3,773,034 A | 11/1973 | Burns et al. |
| 3,859,996 A | 1/1975 | Mizzy et al. |
| 3,952,742 A | 4/1976 | Taylor |
| 4,171,852 A | 10/1979 | Haentjens |
| 4,204,528 A | 5/1980 | Termanini |

(Continued)

FOREIGN PATENT DOCUMENTS

CA 2236958 7/1973

(Continued)

OTHER PUBLICATIONS

US 5,733,250 (withdrawn).

(Continued)

*Primary Examiner*—Rosiland Rollins
(74) *Attorney, Agent, or Firm*—Jones Day

(57) ABSTRACT

Methods and apparatus of embodiments of the invention are adapted to treat tissue inside a patient's body. Aspects of the invention can be used in a wide variety of applications, but certain embodiments provide minimally invasive alternatives for treating atrial fibrillation by delivering a tissue-damaging agent to selected areas of the heart. One exemplary embodiment of the invention provides a method of treating cardiac arrhythmia. This method includes positioning a distal tissue-contacting portion of a body in surface contact with a tissue surface of cardiac tissue; detecting the surface contact between the tissue-contacting portion and the tissue surface; and thereafter, injecting a tissue-ablating agent into the cardiac tissue through the tissue-contacting portion of the body.

32 Claims, 28 Drawing Sheets

U.S. PATENT DOCUMENTS

| | | | |
|---|---|---|---|
| 4,243,035 A | 1/1981 | Barrett |
| 4,266,541 A | 5/1981 | Landau |
| 4,296,100 A | 10/1981 | Franco |
| 4,447,225 A | 5/1984 | Taff et al. |
| 4,531,936 A | 7/1985 | Gordon |
| 4,576,591 A | 3/1986 | Kaye et al. |
| 4,592,742 A | 6/1986 | Landau |
| 4,657,536 A | 4/1987 | Dorman |
| 4,680,027 A | 7/1987 | Parsons et al. |
| 4,767,416 A | 8/1988 | Wolf et al. |
| 4,770,653 A | 9/1988 | Shturman |
| 4,838,850 A | 6/1989 | Rosengart |
| 4,846,814 A | 7/1989 | Ruiz |
| 4,861,339 A | 8/1989 | Jonischkeit |
| 4,898,574 A | 2/1990 | Uchiyama et al. |
| 4,911,148 A | 3/1990 | Sosnowski et al. |
| 4,946,442 A | 8/1990 | Sanagi |
| 4,994,033 A | 2/1991 | Shockey et al. |
| 5,034,003 A | 7/1991 | Denance |
| 5,061,273 A | 10/1991 | Yock |
| 5,064,413 A | 11/1991 | McKinnon et al. |
| 5,100,792 A | 3/1992 | Sanford et al. |
| 5,106,370 A | 4/1992 | Stewart |
| 5,114,423 A | 5/1992 | Kasprzyk et al. |
| 5,130,141 A | 7/1992 | Law et al. |
| 5,179,022 A | 1/1993 | Sanford et al. |
| 5,185,004 A | 2/1993 | Lashinski |
| 5,197,946 A | 3/1993 | Tachibana |
| 5,203,772 A | 4/1993 | Hammerslag et al. |
| 5,228,883 A | 7/1993 | Blakely et al. |
| 5,244,460 A | 9/1993 | Unger et al. |
| 5,307,803 A | 5/1994 | Matsuura et al. |
| 5,308,324 A | 5/1994 | Hammerslag et al. |
| 5,322,511 A | 6/1994 | Armbruster et al. |
| 5,328,470 A | 7/1994 | Nabel et al. |
| 5,336,178 A | 8/1994 | Kaplan et al. |
| 5,356,388 A | 10/1994 | Sepetka et al. |
| 5,370,685 A | 12/1994 | Stevens |
| 5,372,587 A | 12/1994 | Hammerslag et al. |
| 5,380,279 A | 1/1995 | Schmidt |
| 5,383,851 A | 1/1995 | McKinnon, Jr. et al. |
| 5,385,148 A | 1/1995 | Lesh et al. |
| 5,389,096 A | 2/1995 | Aita et al. |
| 5,395,312 A | 3/1995 | Desai |
| 5,397,339 A * | 3/1995 | Desai ..................... 607/116 |
| 5,399,163 A | 3/1995 | Peterson et al. |
| 5,409,000 A | 4/1995 | Imran |
| 5,419,777 A | 5/1995 | Hofling |
| 5,429,131 A | 7/1995 | Scheinman et al. |
| 5,431,168 A | 7/1995 | Webster, Jr. |
| 5,474,540 A | 12/1995 | Miller et al. |
| 5,476,100 A | 12/1995 | Galel |
| 5,480,381 A | 1/1996 | Weston |
| 5,480,382 A | 1/1996 | Hammerslag et al. |
| 5,489,575 A | 2/1996 | Lee et al. |
| 5,492,119 A | 2/1996 | Abrams |
| 5,499,971 A | 3/1996 | Shapland et al. |
| 5,507,724 A | 4/1996 | Hofmann et al. |
| 5,520,639 A | 5/1996 | Peterson et al. |
| 5,569,160 A | 10/1996 | Sauer et al. |
| 5,569,217 A | 10/1996 | Luther |
| 5,571,088 A | 11/1996 | Lennox et al. |
| 5,571,215 A | 11/1996 | Sterman et al. |
| 5,580,859 A | 12/1996 | Felgner et al. |
| 5,589,466 A | 12/1996 | Felgner et al. |
| 5,591,195 A | 1/1997 | Taheri et al. |
| 5,630,795 A | 5/1997 | Kuramoto et al. |
| 5,642,730 A | 7/1997 | Baran |
| 5,652,225 A | 7/1997 | Isner |
| 5,653,684 A | 8/1997 | Laptewicz et al. |
| 5,661,133 A | 8/1997 | Leiden et al. |
| 5,662,124 A | 9/1997 | Wilk |
| 5,693,029 A | 12/1997 | Leonhardt |
| 5,693,622 A | 12/1997 | Wolff et al. |
| 5,698,531 A | 12/1997 | Nabel et al. |
| 5,703,055 A | 12/1997 | Felgner et al. |
| 5,707,969 A | 1/1998 | Nabel et al. |
| 5,713,851 A | 2/1998 | Boudewijn et al. |
| 5,725,523 A | 3/1998 | Mueller |
| 5,730,723 A | 3/1998 | Castellano et al. |
| 5,733,280 A | 3/1998 | Avitall |
| 5,739,118 A | 4/1998 | Carrano et al. |
| 5,760,081 A | 6/1998 | Leaf et al. |
| 5,764,714 A | 6/1998 | Stansell et al. |
| 5,772,590 A | 6/1998 | Webster, Jr. |
| 5,782,239 A | 7/1998 | Webster, Jr. |
| 5,782,802 A | 7/1998 | Landau |
| 5,792,453 A | 8/1998 | Hammond et al. |
| 5,797,870 A | 8/1998 | March et al. |
| 5,797,960 A | 8/1998 | Stevens et al. |
| 5,803,083 A | 9/1998 | Buck et al. |
| 5,807,306 A | 9/1998 | Shapland et al. |
| 5,820,592 A | 10/1998 | Hammerslag |
| 5,827,216 A | 10/1998 | Igo et al. |
| 5,830,993 A | 11/1998 | Blecha et al. |
| 5,833,658 A | 11/1998 | Levy et al. |
| 5,836,905 A | 11/1998 | Lemelson et al. |
| 5,837,533 A | 11/1998 | Boutin |
| 5,840,031 A | 11/1998 | Crowley |
| 5,840,059 A | 11/1998 | March et al. |
| 5,840,062 A | 11/1998 | Gumaste et al. |
| 5,843,050 A | 12/1998 | Jones et al. |
| 5,845,646 A | 12/1998 | Lemelson |
| 5,846,221 A | 12/1998 | Snoke et al. |
| 5,846,225 A | 12/1998 | Rosengart et al. |
| 5,846,946 A | 12/1998 | Huebner et al. |
| 5,854,209 A | 12/1998 | Jacobs, Jr. et al. |
| 5,857,464 A | 1/1999 | Desai |
| 5,860,953 A | 1/1999 | Snoke et al. |
| 5,861,397 A | 1/1999 | Wheeler |
| 5,865,811 A | 2/1999 | Doying, Sr. et al. |
| 5,871,462 A | 2/1999 | Yoder et al. |
| 5,871,495 A | 2/1999 | Mueller |
| 5,876,373 A | 3/1999 | Giba et al. |
| 5,882,332 A | 3/1999 | Wijay |
| 5,885,272 A | 3/1999 | Aita et al. |
| 5,891,086 A | 4/1999 | Weston |
| 5,891,133 A | 4/1999 | Murphy-Chutorian |
| 5,891,136 A | 4/1999 | McGee et al. |
| 5,931,831 A | 8/1999 | Linder |
| 5,935,063 A | 8/1999 | Nguyen |
| 5,941,845 A | 8/1999 | Tu et al. |
| 5,941,868 A | 8/1999 | Kaplan et al. |
| 5,947,988 A | 9/1999 | Smith |
| 5,951,516 A | 9/1999 | Bunyan |
| 5,964,754 A | 10/1999 | Osypka |
| 5,971,983 A | 10/1999 | Lesh |
| 5,993,443 A | 11/1999 | Murphy-Chutorian et al. |
| 5,997,509 A | 12/1999 | Rosengart et al. |
| 5,997,525 A | 12/1999 | March et al. |
| 6,004,269 A | 12/1999 | Crowley et al. |
| 6,006,123 A | 12/1999 | Nguyen et al. |
| 6,007,531 A | 12/1999 | Snoke et al. |
| 6,012,457 A | 1/2000 | Lesh |
| 6,017,322 A | 1/2000 | Snoke et al. |
| 6,024,703 A | 2/2000 | Zanelli et al. |
| 6,036,677 A | 3/2000 | Javier, Jr. et al. |
| 6,056,716 A | 5/2000 | D'Antonio et al. |
| 6,063,022 A | 5/2000 | Ben-Haim |
| 6,102,046 A | 8/2000 | Weinstein et al. |
| 6,102,887 A | 8/2000 | Altman |
| 6,133,233 A | 10/2000 | Ross et al. |
| 6,161,543 A | 12/2000 | Cox et al. |
| 6,171,303 B1 | 1/2001 | Ben-Haim et al. |

| | | | |
|---|---|---|---|
| 6,179,809 B1 | 1/2001 | Khairkhahan et al. | |
| 6,182,444 B1 | 2/2001 | Fulton et al. | |
| 6,183,444 B1 | 2/2001 | Glines et al. | |
| 6,224,584 B1 | 5/2001 | March et al. | |
| 6,237,605 B1 | 5/2001 | Vaska et al. | |
| 6,251,104 B1 | 6/2001 | Kesten et al. | |
| 6,267,760 B1 | 7/2001 | Swanson | |
| 6,309,375 B1 | 10/2001 | Glines et al. | |
| 6,314,962 B1 | 11/2001 | Vaska et al. | |
| 6,314,963 B1 | 11/2001 | Vaska et al. | |
| 6,315,184 B1 * | 11/2001 | Whitman | 227/180.1 |
| 6,322,548 B1 | 11/2001 | Payne et al. | |
| 6,344,027 B1 | 2/2002 | Goll | |
| 6,517,536 B1 * | 2/2003 | Hooven et al. | 606/41 |
| 6,858,028 B1 * | 2/2005 | Mulier et al. | 606/51 |
| 2001/0034501 A1 | 10/2001 | Tom | |

FOREIGN PATENT DOCUMENTS

| | | |
|---|---|---|
| DE | 34 21 390 | 12/1982 |
| DE | 199 04 995 A1 | 2/1999 |
| EP | 489 496 | 6/1992 |
| EP | 908 194 A2 | 4/1999 |
| WO | WO 92/10142 | 6/1992 |
| WO | WO 94/21237 | 9/1994 |
| WO | WO 94/24263 | 10/1994 |
| WO | WO 96/32129 | 10/1996 |
| WO | WO 96/35469 | 11/1996 |
| WO | WO 97/17099 | 5/1997 |
| WO | WO 97/25101 | 7/1997 |
| WO | WO 97/36633 | 10/1997 |
| WO | WO 97/42998 | 11/1997 |
| WO | WO 97/47253 | 12/1997 |
| WO | WO 97/49450 | 12/1997 |
| WO | WO 98/05307 | 2/1998 |
| WO | WO 98/10750 | 3/1998 |
| WO | WO 98/31409 | 7/1998 |
| WO | WO 98/34657 | 8/1998 |
| WO | WO 98/57695 | 12/1998 |
| WO | WO 98/57696 | 12/1998 |
| WO | WO 99/04704 | 4/1999 |
| WO | WO 99/39624 | 8/1999 |
| WO | WO 00/02612 | 1/2000 |
| WO | WO 00/57895 | 10/2000 |
| WO | WO 69348 A | 11/2000 |
| WO | WO/00/72908 | 12/2000 |
| WO | WO 00/72908 | 12/2000 |
| WO | WO 01 05306 A | 1/2001 |

OTHER PUBLICATIONS

Padua et al., "Basic fibroblast growth factor is cardioprotective in ischemia-reperfusion injury" Molecular and Cellular Biochemistry 143: 129-135 (1995).

Shi et al., "PR-39, a proline-rich antibacterial peptide that inhibits phagocyte NADPH oxidase activity by binding to Src homology 3 domains of p47phox" Proc. Natl. Acad. Sci. 93:6014-6018 (1996).

Uchida et al., "Angiogenic therapy of acute myocardial infarction by intrapericardial injection of basic fibroblast growth factor and heparin sulfate: An experimental study" Am. Heart J., 130:1182-1188 (1995).

Unger et al. "Basic fibroblast growth factor enhances myocardial collateral flow in a canine model" Am J. Physiol., 266:H1577-H1595 (1994).

Walterberger et al., "Ischemia-Induced Transplant Arteriosclerosis in the Rat" Arteriosclerosis, Thrombosis and Vascular Biology 16(12):1516-1523 (1996).

Xiaobing, et al. "Ischemia and Reperfusion reduce the Endogenous Basic Fibroblast Growth Factor (bf GF) in Rat Skeletal Muscles" Chinese Medical Journal 108(9): 699-703, (1995).

U.S. Appl. No. 08/646,856, filed May 8, 1996, Payne.

U.S. Appl. No. 60/191,610, filed Mar. 23, 2000, Tom.

U.S. Appl. No. 09/566,196, filed May 5, 2000, Mueller.

Boretos, "Improved Intravascular Delivery of Drug Via a Polyethylene Jet Catheter" 13th Annual Meeting of the Society for Biomaterials, Jun. 2-6, pp. 128 (1987).

Newman and Ross, "Primary Pulmonary Hypertension: A Look at the Future" JACC 14(3):551-555 (1989).

Nicolau, et al., Crit. Rev. Ther. Drug Carrier Syst. 6:239-271 (1989).

Padua et al., "Basic fibroblast growth factor is cardioprotective in ischemia-reperfusion injury" Molecular and Cellular Biochemistry 143: 129-135 (1995).

Yang, N. "Particle Bombardment Technology for Gene Transfer"; ed., Oxford University Press, New York NY pp. 10-11 (1994).

Schumacher et al. "Induction of Neoangiogenesis in Ischemic Myocardium by Human Growth Factors" Circulation 97:645-650 (1998).

Seldinger "Catheter Replacement of the Needle in Percutaneous Arteriography" Acta Radiologica 38:368-376 (1953).

Uchida et al., "Angiogenic therapy of acute myocardial infarction by intrapericardial injection of basic fibroblast growth factor and heparin sulfate: An experimental study" Am. Heart J., 130:1182-1188(1995).

Unger et al. "Basic fibroblast growth factor enhances myocardial collateral flow in a canine model" Am J. Physiol., 266:H1577-H1595 (1994).

Waltenberger et al., "Ischemia-Induce Transplant Arteriosclerosis in the Rat" Arterioclerosis, Thrombosis and Vascular Biology 16(12):1516-1523 (1996).

Xiaobing, et al. "Ischemia and Reperfusion reduce the Endogenous Basic Fibroblast Growth Factor (bf GF) in Rat Skeletal Muscles" Chinese Medical Journal 108(9): 699-703, (1995).

Summers D A et al., The Impact of Waterjets on Human Flesh Proceedings of the International Symposium on Jet Cutting Technology,, GB, Cranfield,BHRA vol. SYMP. 9, pp. 423-433, XP000139962 Oct. 4, 1998.

* cited by examiner

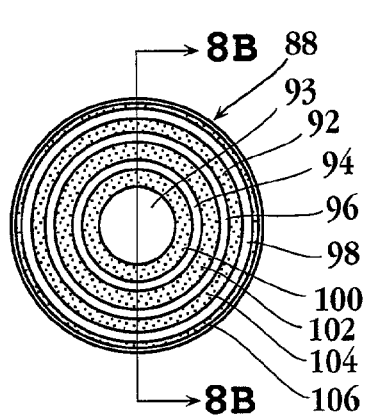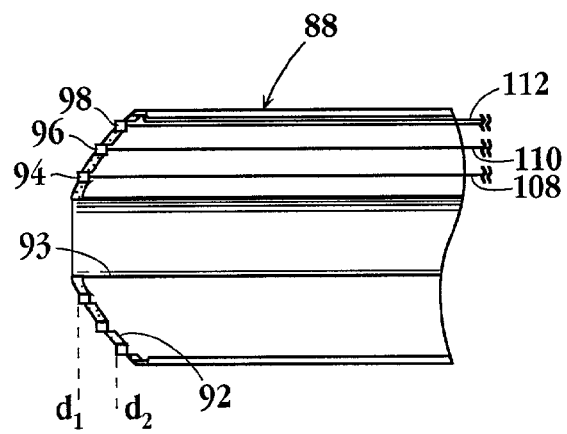
Fig. 8A  Fig. 8B
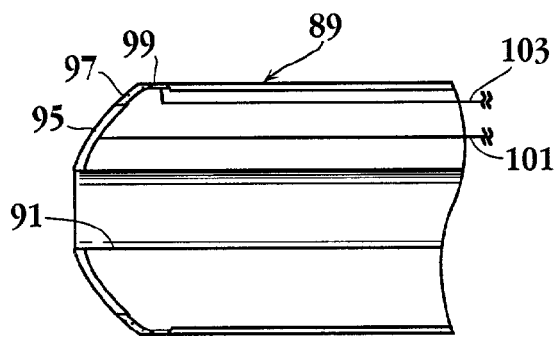
Fig. 8C
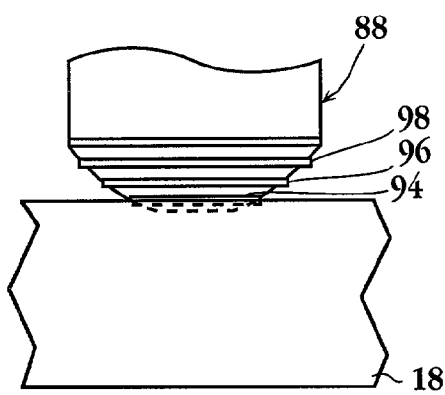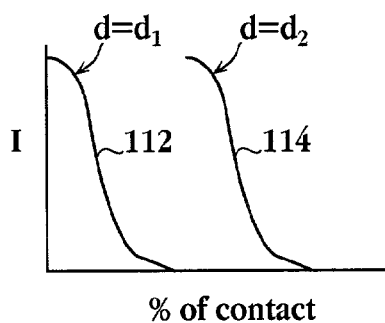
Fig. 9A  Fig. 9B

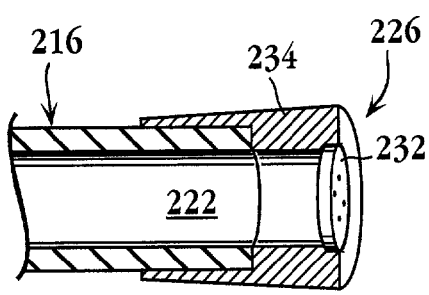
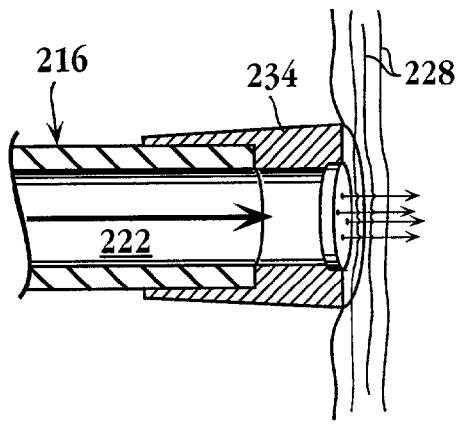
Fig. 16A    Fig. 16B
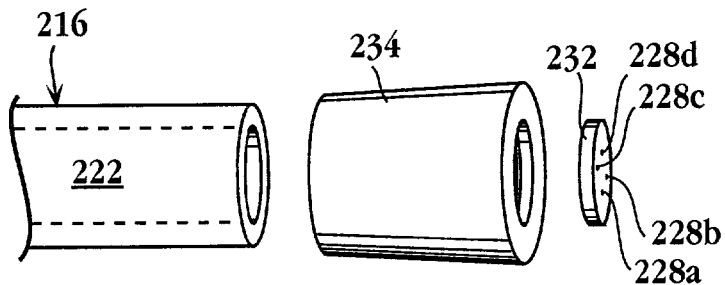
Fig. 17
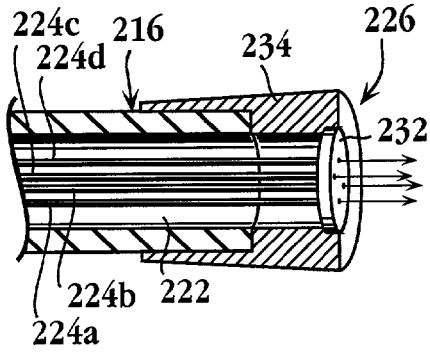
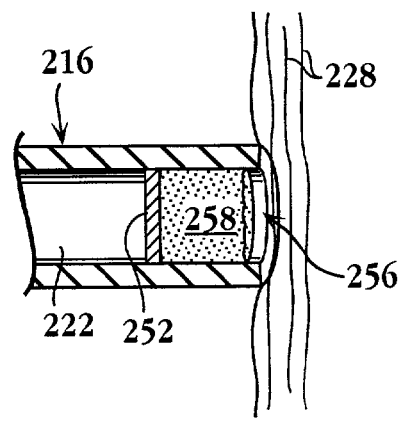
Fig. 18    Fig. 19

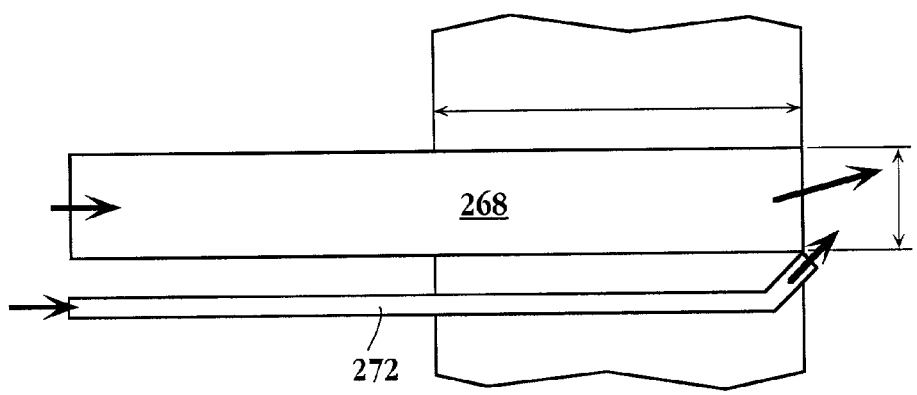
Fig. 20A
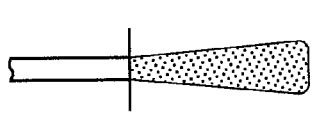   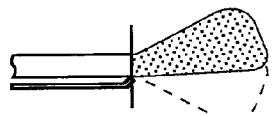   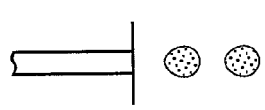
Fig. 20B   Fig. 20C   Fig. 20D
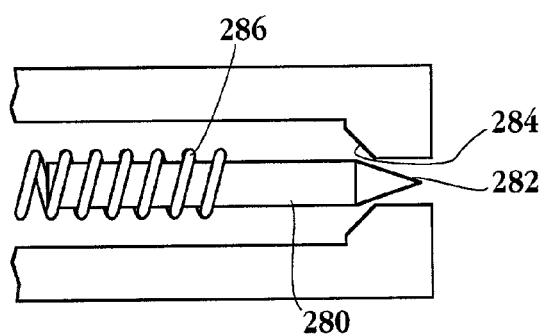
Fig. 21

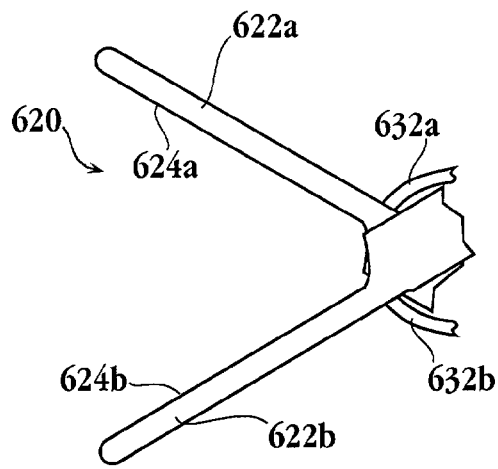
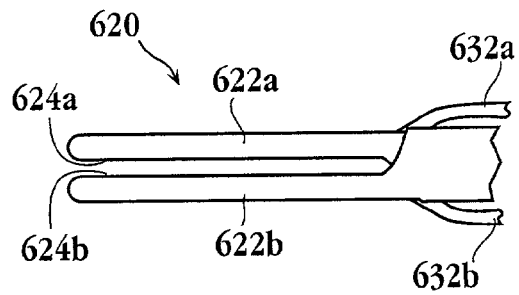
Fig. 38A          Fig. 38B
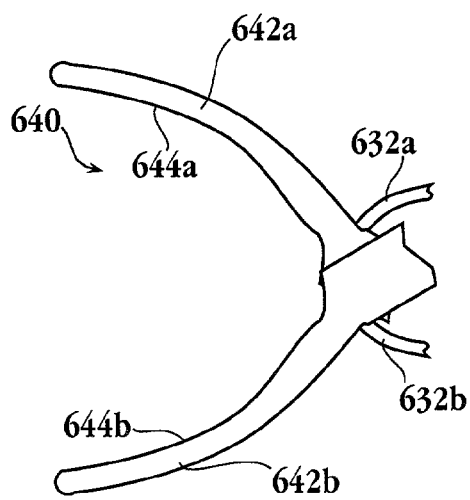
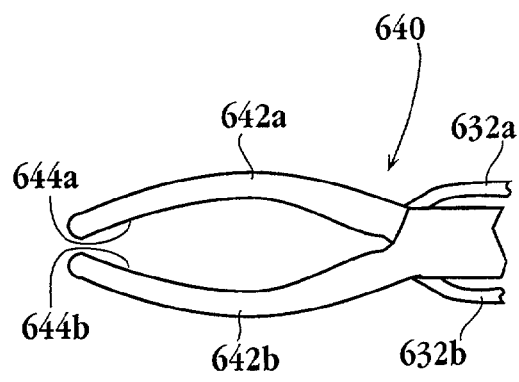
Fig. 39A          Fig. 39B

METHOD AND APPARATUS FOR TREATMENT OF ATRIAL FIBRILLATION

CROSS-REFERENCE TO RELATED APPLICATION(S)

This application claims priority from the following U.S. patent applications, each of which is incorporated herein by reference in its entirety: U.S. Provisional Patent Application 60/137,265, filed Jun. 2, 1999; U.S. patent application Ser. No. 09/585,983, titled "Devices and Methods for Delivering a Drug" filed Jun. 2, 2000; International Application No. PCT/US00/15386, titled "Devices and Methods for Delivering a Drug" filed Jun. 2, 2000 (which was published in English 7 Dec. 2000 as International Publication No. WO 00/72908); U.S. Provisional Patent Application No. 60/275,923, titled "Sensor Device and Apparatus for Affecting a Body Tissue at an Internal Target Region" filed Mar. 14, 2001; U.S. Provisional Patent Application No. 60/327,053, titled "Method and Apparatus for Guided Interventional Procedures" filed Oct. 3, 2001; and U.S. Provisional Patent Application No. 60/340,980, titled "Method and Apparatus for Treatment of Atrial Fibrillation" filed Dec. 7, 2001.

TECHNICAL FIELD

Embodiments of the invention relate generally to medical procedures and interventional medical devices that can be used to treat cardiac arrhythmias and other conditions. Many of these embodiments have particular utility in treating atrial fibrillation.

BACKGROUND

A wide variety of diseases and maladies can be treated by surgical intervention. Increasingly, however, less invasive procedures are sought to achieve similar objectives while reducing risks and recovery time associated with more traditional surgical approaches. For example, a variety of thoracic surgical procedures, such as treatment of aortic aneurysms and arterial stenosis, were traditionally performed via a gross thoracotomy. Less invasive procedures, such as balloon-expanded stents and PTCA, have been developed which avoid the need for a gross thoracotomy, requiring instead only a small incision to gain access to the thoracic cavity intravascularly or through an intercostal opening.

Cardiac arrhythmias present a significant health problem. Cardiac arrhythmias include ventricular tachycardias, supra ventricular tachycardias, and atrial fibrillation. Of these, atrial fibrillation is the most common cardiac arrhythmia. It has been estimated that over one million people in the United States alone suffer from atrial fibrillation. Incidence of atrial fibrillation is expected to increase over the next several decades as populations in the United States and Europe trend older because atrial fibrillation tends to become more common with increasing age.

Atrial fibrillation may be treated with medication intended to maintain normal sinus rhythm and/or decrease ventricular response rates. Not all atrial fibrillation may be successfully managed with medication, though. A surgical approach was developed to create an electrical maze in the atrium with the intention of preventing the atria from fibrillating. Known, appropriately, as the "maze" procedure, this technique involves making atrial incisions which interrupt pathways for reentry circuits which can cause atrial fibrillation and instead direct the cardiac electrical impulse through both atria before allowing the signal to activate the ventricles. As a result, virtually the entire atrial myocardium, with the exception of the atrial appendages and the pulmonary veins, can be electrically activated. The maze procedure is very effective in reducing or eliminating atrial fibrillation. Unfortunately, the procedure is difficult to perform and has traditionally required a gross thoracotomy and cardiopulmonary bypass to permit the surgeon appropriate access to the patient's heart.

Several less invasive techniques have been proposed for achieving a similar maze-like effect in the atrial myocardium without requiring direct surgical intervention. For example, U.S. Pat. No. 6,267,760 (Swanson) and U.S. Pat. No. 6,237,605 (Vaska et al.), both of which are incorporated entirely herein by reference, suggest RF ablation devices intended to ablate cardiac tissue and create atrial myocardial lesions to achieve much the same purpose as the surgical incisions of the standard maze procedure. U.S. Pat. No. 6,161,543 (Cox et al.), which is also incorporated entirely herein by reference, suggests that a cryogenic probe be employed to freeze tissue instead of using the RF ablation devices to heat tissue. Each of these approaches leaves something to be desired, however.

SUMMARY

Embodiments of the present invention provide methods and apparatus adapted to treat tissue inside a patient's body. Some of the embodiments of the invention can be used in a wide variety of applications to treat a number of diseases or conditions. For example, embodiments of the invention can be used to accurately deliver a therapeutic agent (e.g., DNA for gene therapy) to a diseased tissue or deliver an angiogenic substance to induce angiogenesis in hypoxic tissue.

One embodiment of the invention provides a medical device adapted to treat patient tissue which includes a fluid reservoir, a tissue contacting member, and a fluid delivery conduit. The tissue contacting member is adapted to be manipulated into contact with a surface of a target tissue. It also includes a body, first and second tissue-contacting surfaces spaced from one another to define a gap therebetween, and a recess proximate to the gap. The fluid delivery conduit is in fluid communication with the reservoir and has a plurality of outlet ports. A length of the fluid delivery conduit is received in the recess with the outlet ports oriented toward, but spaced from, the gap.

Another embodiment of the invention provides an alternative medical device which includes a fluid reservoir, a tissue grasping member, and first and second fluid delivery conduits in fluid communication with the reservoir. The tissue grasping member has a first tissue contacting member and an opposed second tissue contacting member. The first and second tissue contacting members are operatively associated with one another and movable between a first configuration wherein they have a first relative orientation adapted to receive the tissue therebetween and a second configuration wherein they have a second relative orientation adapted to grasp tissue therebetween. The first fluid delivery conduit has a distal length carried by the first tissue contacting member and a plurality of outlet ports spaced along that distal length. The second fluid delivery conduit has a distal length carried by the second tissue contacting member and a plurality of outlet ports spaced along that distal length. The outlet ports of the first and second fluid delivery conduits are oriented generally inwardly toward one another when the tissue grasping member is in the second configuration.

A method in accordance with an embodiment of the invention can be used to create a line of ablated tissue on a hollow organ or vessel having opposed walls. While this organ may comprise the heart, other organs or body vessel may be treated with this method, as well. The opposed walls of the organ are brought closer together, but not in contact with one another, along a distance within a plane. Tissue in the opposing walls is ablated along the plane to form a corresponding line of ablated tissue through the opposed walls.

A number of embodiments of the invention are particularly well suited for use in treating cardiac arrhythmias. In certain embodiments, the invention provides a minimally invasive alternative for treating atrial fibrillation by delivering a tissue-damaging agent to selected areas of the heart.

One such embodiment provides a medical device that can be used for, among other things, treating cardiac arrhythmia. This medical device includes a reservoir for an injectable tissue-ablating agent. The device may also include an elongate body adapted for introduction into a thoracic cavity. The body may have a distal tissue-contacting member having a length that is flexible and adapted to conform to a surface of a target tissue. A plurality of outlet ports is spaced along the tissue-contacting member and a lumen in the body communicates the fluid supply with the outlet ports. A pressure control is in fluid communication with the reservoir and is operable to establish an elevated pressure within the lumen and propel the tissue-ablating agent from the fluid supply through the outlet ports to define a plurality of spaced-apart fluid jets capable of penetrating the target tissue.

A method of treating cardiac arrhythmia in accordance with a different embodiment of the invention may include positioning a tissue grasping member adjacent a target tissue of a heart atrium or a pulmonary vein. The target tissue has two spaced-apart wall segments. Opposed tissue-contacting members of the tissue grasping member may be moved toward one another to deform the target tissue such that the wall segments are moved closer to, but remain spaced from, one another. Target tissue in contact with the tissue contacting members may be ablated to create a lesion extending through both wall segments.

Still another embodiment of the invention provides a method of at least partially electrically isolating a pulmonary vein from a heart atrium having two spaced-apart wall segments. In this method, the two wall segments are juxtaposed along a first plane. Tissue in both wall segments is ablated along the first plane with an ablating member to form a lesion along a first length of each wall segment. The ablating member may be moved and the two wall segments may be juxtaposed along a second plane, which may coincide with the first plane. Tissue in both wall segments is ablated along the second plane with the ablating member to form a lesion along a second length of each wall segment, the second length adjoining the first length.

In an alternative embodiment of the invention for treating cardiac arrhythmia, a body of an injectate delivery device is guided within a patient's thoracic cavity to position a distal tissue-contacting portion of the body in surface contact with a tissue surface of cardiac tissue. Surface contact between the tissue-contacting portion and the tissue surface is detected. Thereafter, a tissue-ablating agent (e.g., an alcohol, hypertonic saline, or suitably hot or cold saline) is injected into the cardiac tissue through the tissue-contacting portion of the body. If so desired, the surface contact may be detected by supplying an excitation voltage to a plurality of electrodes positioned on the tissue-contacting portion of the body and measuring a level of at least one current conducted by the plurality of electrodes. This level may depend upon a degree of contact between at least two of the electrodes and the tissue surface.

In accordance with another embodiment, a method of treating atrial fibrillation includes guiding an elongate, flexible body into proximity with an exterior tissue surface of a predetermined portion of a cardiac tissue. An elongate tissue-contacting portion of the body is brought into surface contact with the tissue surface. This tissue-contacting portion may include a plurality of electrodes and a level of at least one current conducted by the plurality of electrodes may be measured, with the current level depending on a degree of contact between at least two of the electrodes and the tissue surface. Thereafter, a tissue-ablating fluid may be injected into the cardiac tissue through the tissue-contacting portion of the body, creating a signal-impeding lesion in the cardiac tissue.

BRIEF DESCRIPTION OF THE DRAWINGS

FIG. 8A is an end view of an embodiment of a probe with sensors.

FIG. 8B is a cross-sectional view of an embodiment of a probe with sensors.

FIG. 8C is a cross-sectional view of an embodiment of a probe with sensors.

FIG. 9A is a diagram of an embodiment of a probe with sensors partially intruding into body tissue.

FIG. 9B is a graph of current as a function of percentage of contact between sensors and body tissue.

FIG. 16A is an enlarged, side-sectional view of a distal-end region of the device shown in FIG. 15.

FIG. 16B shows the device of FIGS. 15 and 16A being used to direct four high-energy jets carrying one or more selected therapeutic and/or diagnostic agents through a wall of a selected body organ and into the tissue.

FIG. 17 is an exploded view of the apparatus of FIGS. 16A–B.

FIG. 18 is a partial, side-sectional view of a further embodiment of an agent-delivery apparatus for delivering selected diagnostic and/or therapeutic agents to target sites within a selected body tissue using high-energy jets, according to the teachings of the present invention.

FIG. 19 shows the distal-end region of a steerable catheter-type device for delivering selected diagnostic and/or therapeutic agents to target sites within a selected body tissue using ultrasonic energy, according to one embodiment of the present invention.

FIG. 20A shows, in partial side-sectional view, an exemplary agent-delivery port and a secondary drug or gas port that meets the delivery port at an angle.

FIG. 20B-C schematically illustrates exemplary jet or spray patterns which may be achieved using the apparatus of FIG. 20A.

FIG. 21 is a partial side view, with portions shown in section, of an exemplary valving mechanism operable to regulate fluid flow through an agent-delivery lumen and/or outlet port.

FIGS. 38A and 38B are isolation views of a distal portion of the tissue treatment device of FIG. 37A in an open configuration and in a closed configuration, respectively.

FIGS. 39A and 39B are isolation views of an alternative distal portion, useful in the tissue treatment device of FIG. 37A, in an open configuration and in a closed configuration, respectively.

DETAILED DESCRIPTION

Figure 1:
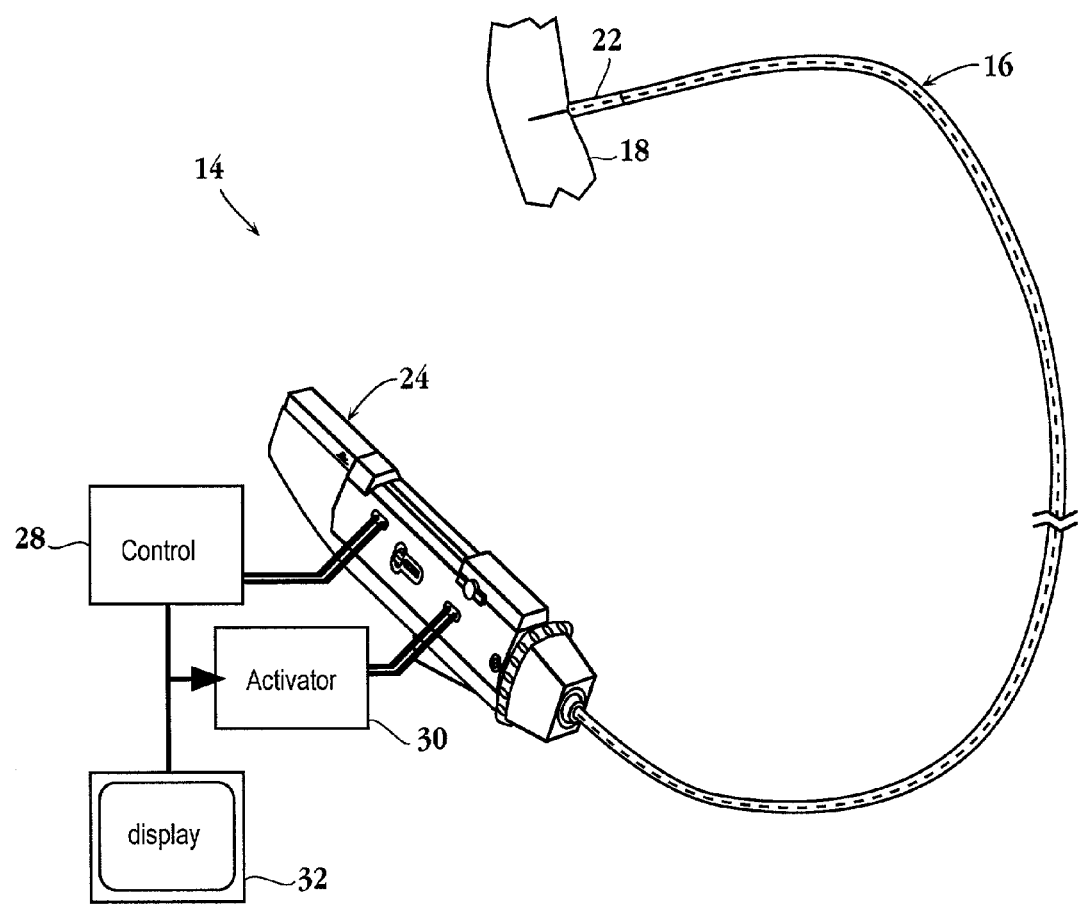
FIG. 1 is a diagram of an embodiment of a catheter apparatus.

Various embodiments of the present invention provide medical devices that can be used in a wide range of applications and several methods that can be used for, among other things, treating cardiac arrhythmia. The following description provides specific details of certain embodiments of the invention illustrated in the drawings to provide a thorough understanding of those embodiments. It should be recognized, however, that the present invention can be reflected in additional embodiments and the invention may be practiced without some of the details in the following description. In the following discussion, embodiments of the invention employing tissue contact sensors are discussed first, followed by embodiments including needles, embodiments providing for needleless injection, and treatment methods in accordance with embodiments of the invention.

Embodiments Including Tissue Contact Sensor(s)

Certain embodiments of the invention provide medical apparatus including sensors that accurately indicate the position of the apparatus in relation to body tissue. The sensors may provide this indication without secondary sources of information, such as previously developed maps of body regions. In certain embodiments, the sensors that provide the position information further provide physiological information. The sensor or sensors may be placed on various locations on the catheter shaft and on the distal tip, depending on the application and desired information required for the surgical or diagnostic procedure. In one embodiment, the sensors are electrodes that indicate a degree of contact between the apparatus and a tissue surface, and also indicate an orientation of the apparatus with respect to the tissue surface. The sensors further transmit an EKG signal from the body tissue. The indication of the degree of contact includes a pressure indication, or an indication of the degree the apparatus intrudes into the body tissue. In one embodiment, a working element includes a sensor. For example, in one embodiment, the working element is a needle that delivers a drug and also transmits an EKG signal such that the condition of the tissue is monitored before and after the drug is delivered. In one embodiment, the apparatus includes a catheter with sensors on a distal probe for positioning the distal probe, and a working element with a sensor disposed in a lumen of the catheter.

FIG. 1 is a diagram of an embodiment of an apparatus 14 for guided interventional procedures. The apparatus 14 includes an assembly 16 for accessing a body tissue surface 18 inside a patient's body, and an actuator 24. The actuator 24 is attached to the assembly 16 in such a way as to steer the assembly 16 by one of several known methods. A distal end probe 22 is placed in contact with the tissue surface 18 in order to perform an interventional procedure. Sensors (not shown in the figure) in the distal probe 22 are electrically connected to a control unit 28. The control unit 28 includes a power source for supplying voltage across the sensors, and circuitry for receiving and processing signals. For example, the control unit 28 includes circuitry for detecting and measuring current levels across the sensors.

The control unit 28 is connected to an activator 30 and a display 32. The control unit 28 is further connected to the actuator 24. In one embodiment, the actuator 24 is automatically controlled depending upon signals received from the sensors by the control unit 28. For example, the actuator 24 is directed to move the distal end probe or to stop moving the distal end probe 22 dependent upon a predetermined relative position of the distal end probe 22 with respect to the tissue surface 18. The display 32 displays information about the relative position, such as the angle of the distal end probe 22 with respect to the tissue surface 18 and the degree of intrusion of the distal end probe 22 into the tissue surface 18. In one embodiment, the display 32 further presents EKG information.

In one embodiment, the assembly 16 is a known steerable catheter assembly. In one application, the assembly 16 is used to access an internal target tissue region, and to provide a therapeutic stimulus. The therapeutic stimulus can be any of several known stimuli, such as injection of a therapeutic compound, cells, or gene, forming a laser channel, or introducing an injury on or below the surface of the target region. Ultrasonic waves, infrared radiation, electromagnetic radiation, or mechanical means, for example, can introduce the injury. In one embodiment useful for treatment of atrial fibrillation, an ablative agent or other tissue-damaging fluid may be injected through and/or below the surface of the target tissue. The therapeutic stimulus may be administered/provided through the distal end probe 22.

In one embodiment, the assembly 16 is sized to be manipulated through the vasculature of a patient until the distal end probe 22 is proximate a surface or wall region of a selected tissue or organ. For example, the distal end probe 22 may be placed within about 5 mm of a tissue surface within a heart chamber, such as the heart endocardial wall within the left ventricle.

In embodiments used for procedures that include injecting a compound or gene into tissue, the actuator 24 includes a drug delivery module. The drug can be delivered by a needle or by a needleless injection mechanism in the distal end probe 22.

In various embodiments, the assembly 16 is an endoscopic device having a distal end probe and a distal end working element (not shown) for introducing or providing a therapeutic effect at or adjacent an organ or tissue target site. Also contemplated is a rigid accessing tool (not shown) that includes an elongate rod that can be guided through an incision, such as in the chest wall, for placement of a distal end probe carried on the rod against the surface of the target tissue.

Figure 2:
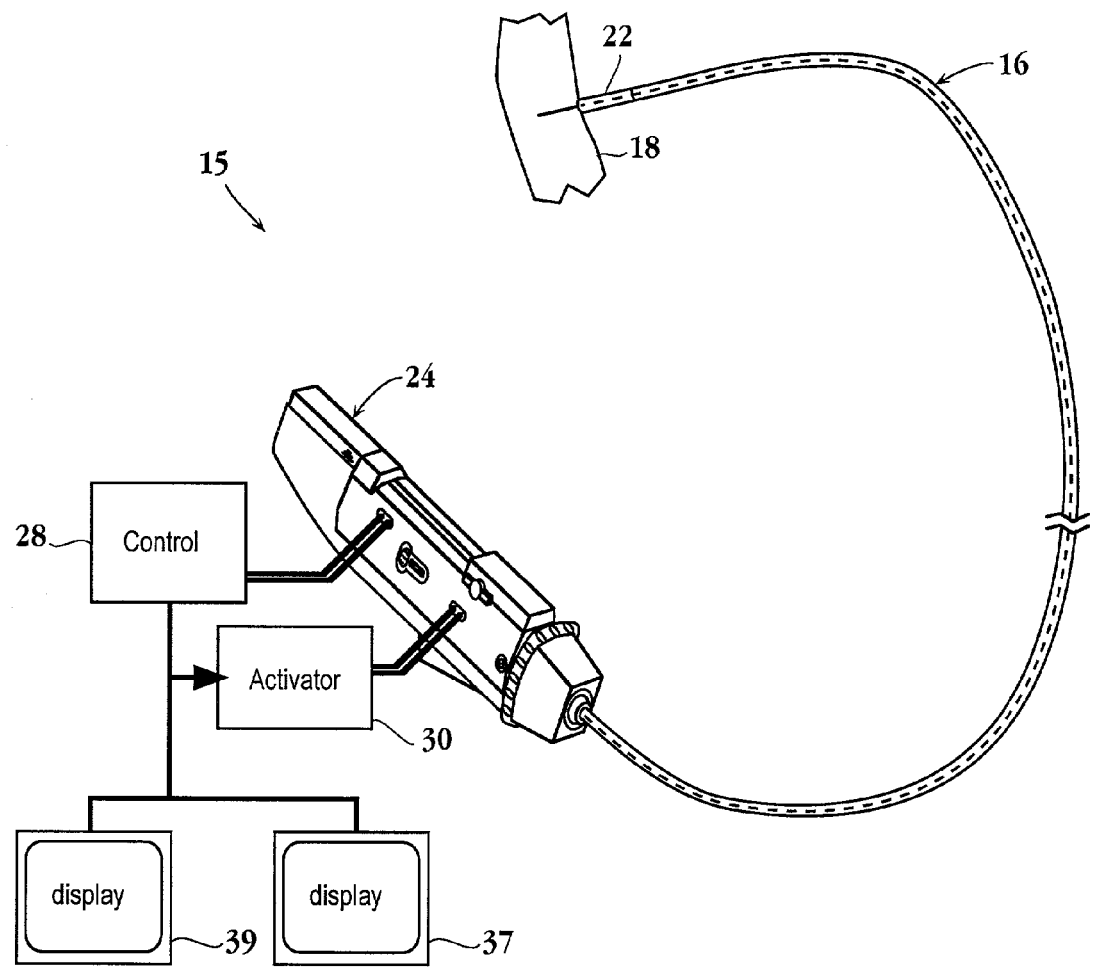
FIG. 2 is a diagram of an embodiment of a catheter apparatus.

FIG. 2 is a diagram of an embodiment of an apparatus 15 for guided interventional procedures that includes separate display devices for position information and for physiological information. The apparatus 15 includes the assembly 16 and the actuator 24. The apparatus further includes the control unit 28 and the activator 30. The display 37 displays position information from sensors as described below. The display 39 displays EKG information. In one embodiment, the display 39 is a commercially available EKG monitor. In one embodiment, the display 37 and the display 39 receive the same signal and filter out unneeded signal components. In one embodiment, the signal is one or more current levels from electrode sensors, as described below.

Figure 3A:
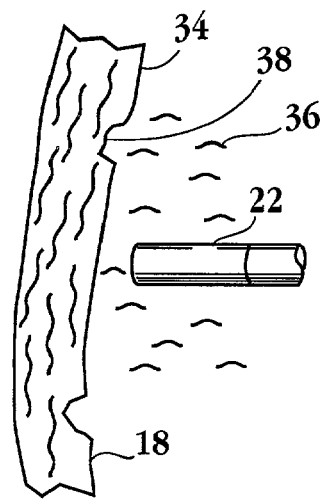
FIG. 3A is a diagram of the distal end of an embodiment of an apparatus showing the relative position of the distal end to body tissue.

FIG. 3A is a diagram showing the distal end probe 22 and the tissue surface 18. The tissue surface 18 is part of a target region of cardiac tissue 34, e.g., a heart interior wall or exterior wall. A heart-wall trabecula 38 is also shown. Heart-wall trabeculae are typically about 2–3 mm in diameter and have a depth of 1.5 to 2 mm. As an example of an application, the target region can be a hypoxic region identified as lacking sufficient oxygen, presumably due to poor vascularization in the region. The therapeutic objective is to stimulate angiogenesis in the hypoxic region by introducing an angiogenic agent and/or by stimulating the tissue with an angiogenic injury. The tissue surface 18 in this example may comprise part of a heart chamber wall. The heart chamber may be filled with blood in contact with the tissue surface 18. A second example is the injection of cells for tissue regeneration in an infarcted region of the heart. In accordance with another embodiment useful in treating cardiac arrhythmia, particularly atrial fibrillation, the cardiac tissue 34 shown in FIGS. 3A–E may comprise a portion of an atrial wall. For example, the cardiac tissue 34 may be located adjacent a pulmonary vein such that forming a cardiac lesion at the site could help electrically isolate a pulmonary vein.

The sensors and the control unit (neither of which are shown in FIG. 3) can be used to detect that the distal end probe 22 probe is properly placed with respect to the tissue surface when the therapy is delivered. Optimal placement of distal end probe 22 has several components. For example, the distal face of the distal end probe may be in contact with, or very close to, the tissue surface 18 in the target region receiving the treatment to more effectively control the level of therapeutic stimulus being delivered. FIG. 3A illustrates a situation in which the distal end probe 22 is in the chamber but not in contact with the heart wall 34. In many methods of the invention, the therapeutic stimulus should not be applied in this situation.

Figure 3B:
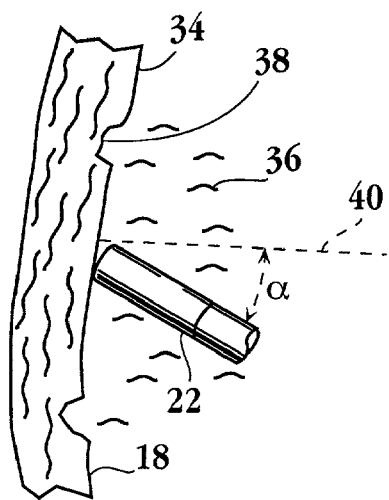
FIG. 3B is a diagram of the distal end of an embodiment of an apparatus showing the relative position of the distal end to body tissue.

FIG. 3B illustrates the angle of contact a between the distal end probe 22 and the tissue surface 18. This is another component of optimal distal end probe 22 placement. The angle of contact a should be within a desired range, e.g., no more than 10°–30°, with respect to an axis 40 that is normal to the tissue surface 18. Typically, as the angle a increases, the distal end probe 22 is less in contact with the tissue surface 18, and consequently the therapeutic stimulus is distributed over a wider area rather than being concentrated in the target region. If the therapeutic stimulus comprises a tissue-damaging agent for use in creating lesions to treat cardiac arrhythmia, for example, dispersing the agent over a wider or less precisely controlled area may lead to collateral tissue damage.

Figure 3C:
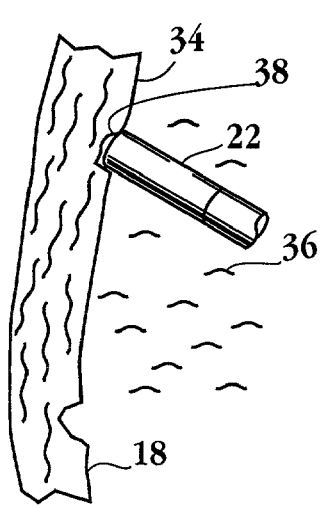
FIG. 3C is a diagram of the distal end of an embodiment of an apparatus showing the relative position of the distal end to body tissue.

Optimal placement of the distal end probe 22 can be complicated by the presence of trabecula 38 or other irregularities on the heart wall 34, as illustrated in FIG. 3C. FIG. 3C shows initial contact of the probe with trabecula 38, which is essentially a recessed area in the target region. In this case, the distal end probe 22 makes contact with the target region, and even intrudes into the target region, but contact between the distal face of the distal end probe 22 and the tissue surface 18 is limited. As will be explained below, this limited contact may be detected and avoided using embodiments of the apparatus 14.

Figure 3D:
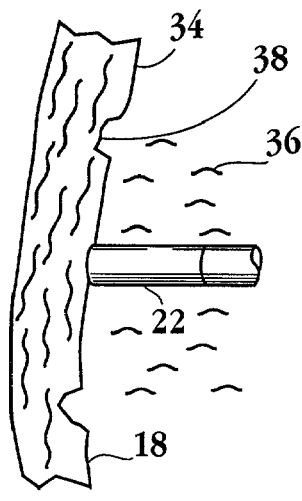
FIG. 3D is a diagram of the distal end of an embodiment of an apparatus showing the relative position of the distal end to body tissue.

FIG. 3D illustrates a surface contact condition between the distal end probe 22 and the tissue surface 18 that is optimal for certain procedures. In this illustrated condition, the longitudinal axis of the distal end probe 22 is substantially perpendicular to the plane of the tissue surface 18. For some procedures to be most effective, the distal end probe 22 should be applied to the tissue surface 18 with a force that is within a predetermined optimal range.

Figure 3E:
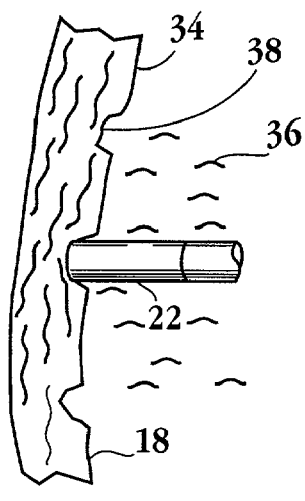
FIG. 3E is a diagram of the distal end of an embodiment of an apparatus showing the relative position of the distal end to body tissue.

The depth of intrusion of the distal end probe 22 into the tissue surface 18 is another factor that can effect optimal distal end probe 22 placement. FIG. 3E shows the distal end probe 22 intruding into the tissue surface 18 in the target region. The tissue surface 18 in the target region is distorted as a result. In addition, the thickness of the heart wall is reduced locally. The tissue distortion may adversely affect the application of the stimulus, and the reduced tissue thickness may lead to suboptimal targeting of the stimulus.

Achieving a desired contact angle and contact force is further complicated in the heart by the beating of the heart. In one embodiment (not shown), the heart wall movement is compensated for by a mechanism near the distal end probe 22 that accommodates movement in multiple axes with little change in contact angle and pressure. In other embodiments, the distal end probe is flexible so as to allow movement in multiple axes. In various embodiments, the procedure includes timing the delivery of the therapy to coincide with a defined period of the cardiac cycle when optimal contact occurs.

Figure 4A:
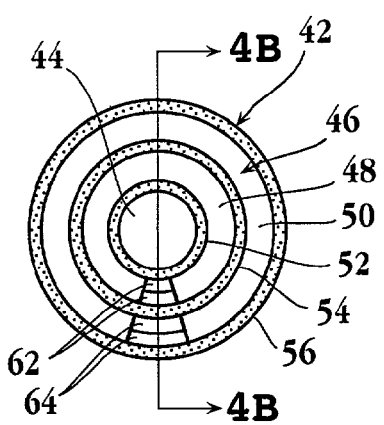
FIG. 4A is an end view of an embodiment of a probe with sensors.

FIG. 4A is an end view of an embodiment of a distal end probe 42 that allows surface contact between the distal end probe 42 and a tissue surface to be sensed during a procedure. The distal end probe 42 includes a lumen 44 through which a therapeutic stimulus can be administered. A planar front face 46 may be placed in contact with the target tissue when the stimulus is administered. Inner and outer annular electrodes, or sensors, 48 and 50, respectively, surround the lumen 44 and are separated by insulators 52, 54, and 56. In one embodiment, the electrodes 48 and 50 are formed of gold, silver, or another conductive material, and are formed on the probe face by plating or attachment methods.

Figure 4B:
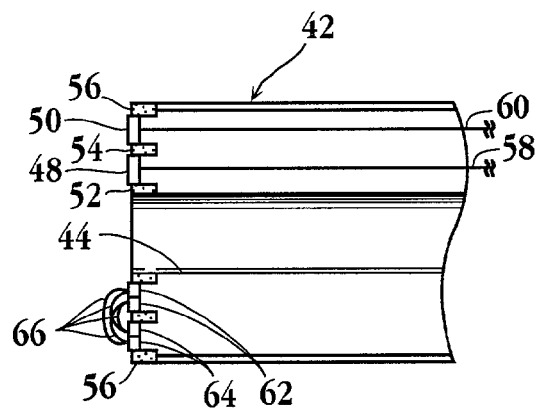
FIG. 4B is a cross-sectional view of an embodiment of a probe with sensors.

In describing the operation of the electrodes, it is useful to consider each electrode as being made up of multiple electrode surface elements, such as electrode elements 62 in electrode 48 and corresponding electrode elements 64 in electrode 50. The electrode elements have arbitrarily defined sizes and positions on their respective electrodes. Current paths exist between electrode elements of electrode 48 and corresponding electrode elements of electrode 50. Referring to FIG. 4B, current paths between corresponding electrode elements 62 and 64 are indicated at 66. Each such current path represents a path current flow between corresponding electrode elements of electrodes 48 and 50. Current flows along the current paths 66 when a voltage potential is applied across the electrodes 48 and 50, and corresponding electrode elements are electrically connected.

In certain applications, corresponding electrode elements of electrodes 48 and 50 are electrically connected when immersed in an electrolytic medium, such as blood. When the electrode elements are electrically connected by the medium, there is maximum current flow. When an electrode element is in contact with a tissue surface, the current path between the electrode elements passes through the tissue surface, which may have a much higher resistance. By monitoring the current between electrode elements 48 and 50, the electrodes may be employed as sensors to detect contact between the distal end probe 42 and the tissue surface.

In various embodiments, the electrodes 48 and 50 are electrically connected to circuitry, such as that described with reference to the control unit 28 of FIG. 1, through conductors 58 and 60. The circuitry measures the extent to which the current paths between corresponding electrode elements are blocked or enabled by measuring total current flow across the electrodes 48 and 50 when a voltage is applied across the electrodes 48 and 50.

Figure 5A:
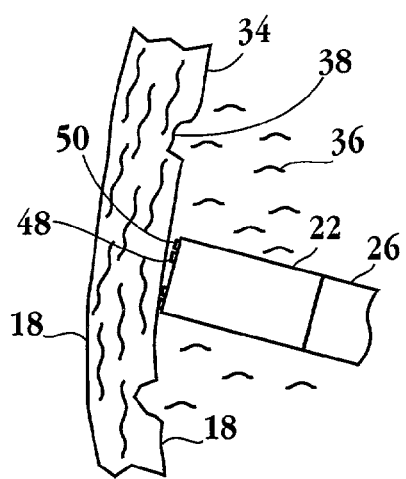
FIG. 5A is a diagram of an embodiment of a probe with sensors, showing the relative position of the probe and the sensors to body tissue.
Figure 5B:
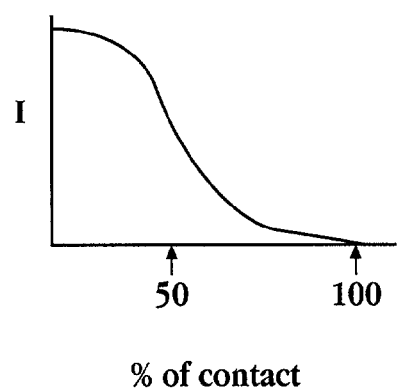
FIG. 5B is a graph of current as a function of percentage of contact between sensors and body tissue.

FIG. 5A is a diagram showing the distal end probe 22 in partial contact with the tissue surface 18. Inner electrode 48 and outer electrode 50 are also shown schematically. When the distal end probe 22 contacts the tissue surface 18 at an angle other than 90°, as shown in FIG. 5A, the electrode elements in contact with the tissue surface will conduct relatively little current while the exposed electrode elements may remain in contact with a more conductive medium, such as blood. The relationship between the percentage of the probe face 46 in contact with the tissue surface and the current through the electrode elements is shown in FIG. 5B. Little or no contact results in maximum current. The amount of current decreases in the manner shown until complete or substantially complete contact is achieved, thus providing an indication of the amount of contact between the distal end probe 22 and the tissue surface.

When the distal end probe is guided into place transvascularly, the blood will provide a conductive path between the electrodes 48 and 50 and the tissue will provide a relatively less conductive path. In other embodiments of the invention, however, blood may not provide a consistent conductive medium between the electrodes 48 and 50 prior to contact with the tissue. For example, if the distal end probe 22 is introduced into a relatively dry field, such as the thoracic cavity via an intercostal incision, little or no current will be conducted between the electrodes 48 and 50 prior to contacting the patient's tissue. When the patient's tissue is contacted, however, the relatively moist tissue surface may provide sufficient conductivity to establish a detectable increase in current between the electrodes 48 and 50. Again, the increase in detected current may be proportional to the surface area of the electrodes 48 and 50 in contact with the target tissue surface, but with current increasing with increasing tissue contact in this circumstance. By appropriate modification of the circuitry in the control unit 28 (FIG. 1), the electrodes 48 and 50 can, therefore, be adapted to detect tissue contact as reflected in a drop in current or an increase in current.

In one embodiment of the distal end probe 22, one or more of the electrodes 48 and 50 function as physiological sensors. In one embodiment, the physiological sensors are EKG sensors. The electrodes 48 and 50 transmit EKG data to a control unit, such as the control unit 28 in FIG. 1, via the conductors 58 and 60. The EKG data is processed and displayed. The availability of EKG information with position information during a procedure has several advantages. For example, the position information provides a precise origin of the EKG information. In addition, when a therapeutic agent is introduced into a target region of tissue, the change in the tissue can be observed in real-time through the EKG. The EKG information assists the user in assessing the health of tissue in a prospective target region. For example, a user may discard a previously chosen target region for injecting an angiogenic agent because the EKG information indicates the tissue in the region is infarcted. Conversely, the user can check the EKG information when the distal end probe has been positioned and deliver the therapeutic agent if the condition of the tissue is satisfactory per the EKG information.

Figure 6A:
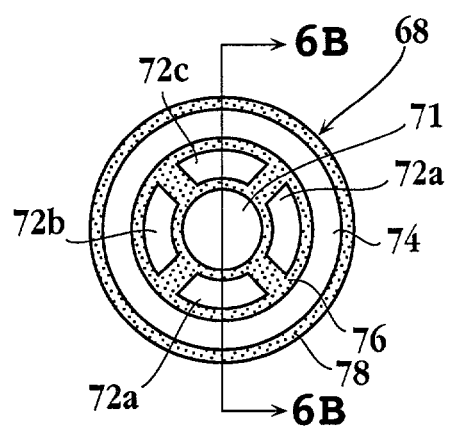
FIG. 6A is an end view of an embodiment of a probe with sensors.

FIG. 6A is an end view of an embodiment of a distal end probe 68 that allows the quality of contact between the distal end probe 68 and a tissue surface to be sensed. The quality of contact includes degree of contact and the angle between the longitudinal axis of the distal end probe 68 and the tissue surface. The distal end probe 68 includes a lumen 71. A probe face 70 (shown in FIG. 6B) of the distal end probe 68 includes an outer annular electrode, or sensor, 74, and an inner annular electrode, or sensor, 72 that includes multiple electrode sections 72a, 72b, 72c, and 72d. The insulators 78 and 76 separate the electrodes 72 and 74. The insulator 76 further separates the sections of the electrode 72 from each other.

Figure 6B:
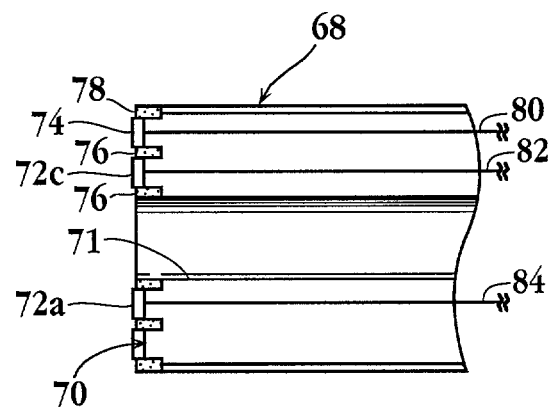
FIG. 6B is a cross-sectional view of the embodiment of FIG. 6A.

As shown in the cross-sectional view of FIG. 6B, the electrodes 72 and 74 are electrically connected to circuitry, such as that described with reference to the control unit 28 of FIG. 1, through conductors 80, 82, and 84. The coupling 80 is connected to the electrode 74. Each of the electrodes 72a, 72b, 72c, and 72d are connected to a different coupling, only two of which (82 and 84) are shown.

Figure 7A:
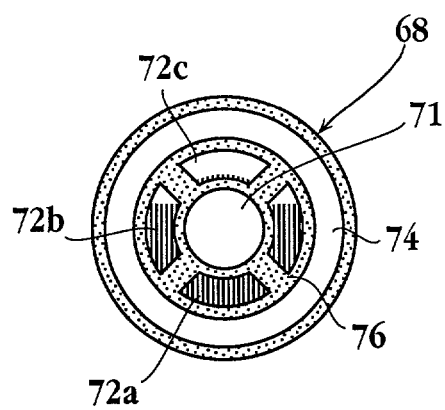
FIG. 7A is an end view of an embodiment of a probe with sensors, illustrating partial contact between the sensors and body tissue.

Through the conductors 80, 82, and 84, voltages are applied separately to each of the electrodes 72 and to electrode 74. Current may flow best between the electrodes 74 and 72 in the areas that are not in contact with tissue. FIG. 7A illustrates a case in which the distal end probe 68 is in partial contact with a tissue surface such that there is an angle of less than 90° between the longitudinal axis of the distal end probe 68 and the tissue surface. The shaded regions of the electrodes 72 indicate contact with the tissue surface. In this case, there is complete contact between the lower portion (in the figure) of the planar probe face 71 and the tissue surface. There is also partial contact between the right and left sides (in the figure) of the probe face 71 and the tissue surface.

Figure 7B:
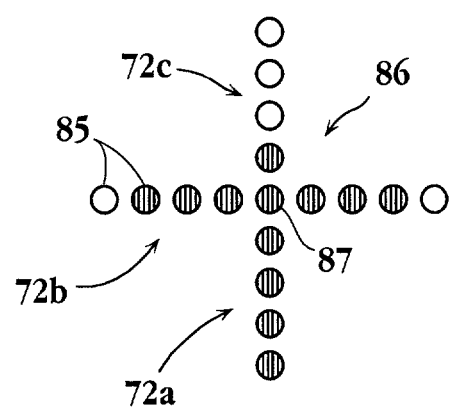
FIG. 7B is a diagram of an embodiment of a display that indicates partial contact between sensors and body tissue.

FIG. 7B is a diagram of an embodiment of a display 86. The display 86 indicates the angle and degree of contact corresponding to the current flow as shown in FIG. 7A. Indicators 85 are typical of the 17 indicators that are arranged in two lines that intersect at an indicator 87 as shown. The indicators 85 are arranged to suggest the manner in which the plurality of sensors is arranged on the distal end probe 68. The arrangement of the indicators generally corresponds to locations on the probe face 71. A shaded indicator 85 indicates contact between the probe face 71 and the tissue surface at the location of the shaded indicator. An unshaded indicator 85 indicates no contact between the probe face 71 and the tissue surface at the location of the unshaded indicator. In one embodiment, the indicators are lights, such as light emitting diodes (LEDs), and are lit when a corresponding electrode is in contact with tissue. The display 86 allows a user to quickly assess angle and degree of contact between the probe face 71 and the tissue surface.

In one embodiment of the distal end probe 68, one or more of the electrodes 72 and 74 function as physiological sensors. In one embodiment, the physiological sensors are EKG sensors. The electrodes 72 and 74 transmit EKG data to a control unit, such as the control unit 28 in FIG. 1, via the conductors 80, 82, 84, etc. The EKG data is processed and displayed.

FIGS. 8A–8C are diagrams of an embodiment of a distal end probe 88 that facilitates a determination of the angle of contact between the probe face 92 and a tissue surface. The distal end probe 88 further facilitates a determination of a degree to which the distal end probe 88 intrudes into the tissue surface. The probe face 92 is rounded, as seen in cross-section in FIG. 8B. Annular electrodes, or sensors, 94, 96, and 98 are arranged at increasing radii about a lumen 93. Insulators 100, 102, 104, and 106 separate the electrodes 94, 96, and 98. The electrodes 94, 96, and 98 are electrically connected to connected to circuitry, such as that described with reference to the control unit 28 of FIG. 1, through conductors 108, 110, and 112. Voltages are separately applied to each of the electrodes 94, 96, and electrode 98 through the respective conductors 108, 110, and 112, creating a current flow in proportion to amount and location of contact between the electrodes and the tissue surface.

FIG. 8C is a diagram of an alternative electrode configuration. The distal end probe 89 includes a lumen 91. An inner annular electrode 95 substantially covers the rounded face of the distal end probe 89. The inner annular electrode 95 is separated from an outer annular electrode 99 by an insulator 97. The electrodes 95 and 97 are electrically connected to circuitry, such as that described with reference to the control unit 28 of FIG. 1, through conductors 101 and 103.

FIGS. 9A and 9B illustrate an example of one application for the distal end probe 88 and the information provided by the electrodes 94, 96, and 98. FIG. 9A shows the distal end probe in contact with the tissue surface 18. The distal end probe 88 intrudes into the tissue surface 18 such that the electrode 94 is in contact with the tissue surface 18, but the electrodes 96 and 98 are not in contact. FIG. 9B shows two graphs that each plot current as a function of degree of contact between an electrode and the tissue surface 18. The curve 112 shows the plot for the distal end probe intruding into the tissue surface 18 to distance d1. The curve 114 shows the plot for the distal end probe intruding into the tissue surface 18 to distance d2. Distances d1 and d2 are illustrated in FIG. 8B.

The current levels on the plots for d1 and d2 vary depending on the angle of contact and depth of intrusion of the distal end probe 18. For example, an optimal contact would give a low current level at $d_1$, indicating a good contact angle, and a high level at $d_2$, indicating a desired depth of intrusion. Various current levels can indicate a contact angle that is not close enough to 90° and/or a level of tissue intrusion that is too high or too low.

Figure 10A:
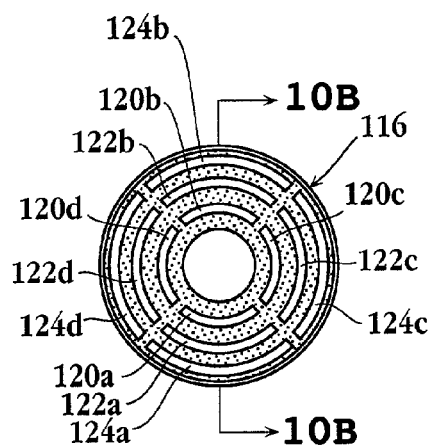
FIG. 10A is an end view of an embodiment of a probe with sensors.
Figure 10B:
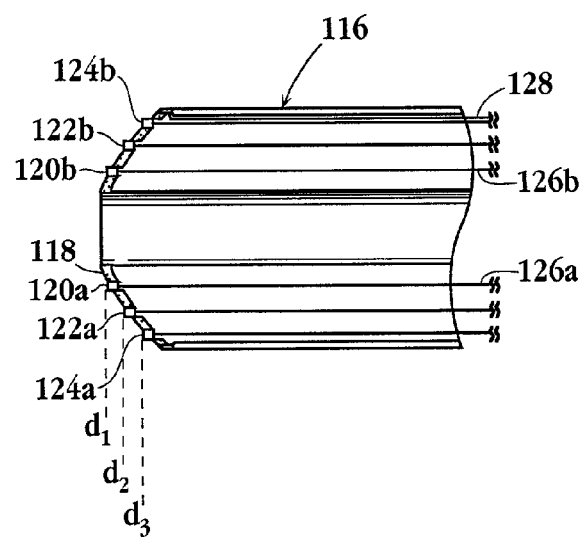
FIG. 10B is a cross-sectional view of an embodiment of a probe with sensors.

FIGS. 10A and 10B illustrate an embodiment of a distal end probe 116 that allows the user to obtain information about the angle of contact of the distal end probe 116 with the tissue, and the depth of intrusion into the tissue. The distal end probe 116, as shown in FIG. 10A, includes electrodes, or sensors, 120, 122, and 124. Each of the electrodes 120, 122, and 124 are annular and arranged concentrically about the longitudinal axis of the distal end probe 116. Each of the electrodes 122, 124, and 126 are divided into four electrode sections (labeled a, b, c, and d) that are each electrically insulated from any other electrode section by an insulating material, indicated by shading.

The distal end probe 116, as shown in FIG. 10B, has a rounded probe face 118 that includes the electrodes 120, 122, and 124 at distances $d_1$, $d_2$, and $d_3$, respectively, from the distal end of the distal end probe 118. Each of the sections a, b, c, and d of the electrodes 120, 122, and 124 are electrically connected to circuitry, such as that described with reference to the control unit 28 of FIG. 1, through conductors. For example, the coupling 128b is connected to the electrode section 124b, the coupling 126b is connected to the electrode section 120b, and the coupling 126a is connected to the electrode section 120a.

Figure 11A:
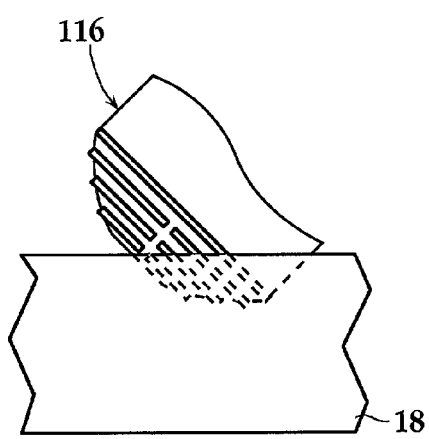
FIG. 11A is a diagram of an embodiment of a probe with sensors partially intruding into body tissue such that the probe is not perpendicular to the body tissue surface.
Figure 11B:
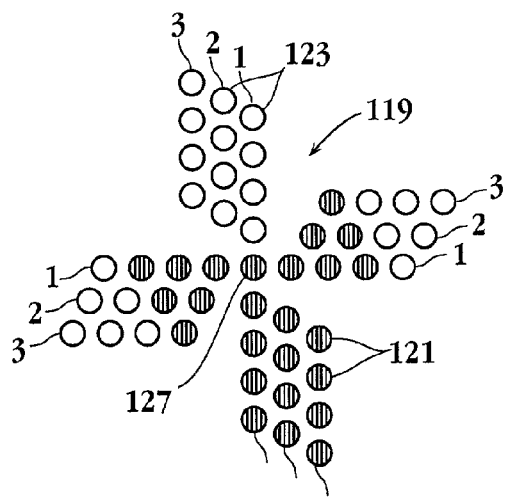
FIG. 11B is a diagram of a display of one embodiment that indicates the position of the probe with respect to the body tissue surface and a degree of intrusion into the body tissue.

FIG. 11A illustrates the distal end probe 116 in contact with the tissue surface 18 such that the electrodes, or sensors, 120, 122, and 124 are partially in contact with the tissue surface 18, including partial intrusion into the tissue surface 18. FIG. 11B is an embodiment of a display with four groups of indicators. The indicators are arranged to suggest the manner in which the plurality of sensors is arranged on the distal end probe 116. The arrangement of the indicators generally corresponds to locations about the distal end probe 116. Each of the indicators is similar to exemplary indicators 122 and 124. Indicators 122 are shaded to indicate contact between the distal end probe 116 and the tissue surface 18. Indicators 124 are not shaded to indicate no contact between the distal end probe 116 and the tissue surface 18. In one embodiment, the indicators are lights, such as light emitting diodes (LEDs), and are lit when a corresponding electrode is in contact with tissue. Within each of the four groups of indicators, four indicators are in a line with a central indicator 125, indicated as lines 1. These indicators indicate the current flow through electrode sections at probe depth $d_1$ thus indicating contact at depth d1. The four indicators in lines 2 indicate the current flow through electrode sections at depth d2. The next four indicators in lines 3 indicate the current flow through electrode sections at depth $d_3$. The display pattern in FIG. 11B indicates that the electrode sections at all three depths at an arbitrarily designated "lower" portion of the distal end probe 116 are in contact with the tissue surface, as shown by the shaded indicators. The inner electrode sections on two "sides" of the distal end probe 116 adjacent the lower portion are also in contact with the tissue surface. The "upper" electrode sections are not in contact with the tissue, as indicated by unshaded indicators. This display reflects the contact situation shown in FIG. 11A.

The information displayed as in FIGS. 5B, 7B, 9B, and 11B can be used to determine when to deliver a drug, or some other therapy, to the tissue through the distal end probe. As discussed in more detail below, in certain embodiments of the invention, an injectate is injected into the patent's tissue only after appropriate surface contact between the medical device and the tissue has been detected.

In one embodiment of the distal end probe 116, one or more of the electrodes 120, 122, and 124 function as physiological sensors. In one embodiment, the physiological sensors are EKG sensors. The electrodes 120, 122, and 124 transmit EKG data to a control unit, such as the control unit 28 in FIG. 1, via the conductors 128b, 126a, 126b, etc. The EKG data is processed and displayed.

Referring to control unit 28 of FIG. 1, in one embodiment, the control unit 28 further controls the delivery of a drug or therapy when an appropriate position of the distal end probe with respect to the tissue surface has been achieved. In one embodiment, the activator 30 receives data from the control unit 28, and sends an activation signal to the actuator 24 when the data indicates that the appropriate position of the distal end probe with respect to the tissue surface has been achieved. The activator 30 is programmable to send the activation signal under specified conditions, including specified distance from tissue, specified degree of contact with tissue, specified angle of contact with tissue and specified degree of intrusion into tissue. In one embodiment, the activator 30 further includes circuitry for guiding the position of the distal end probe via the actuator 24 until a desired contact position is achieved.

Embodiments Employing Needles

Figure 12A:
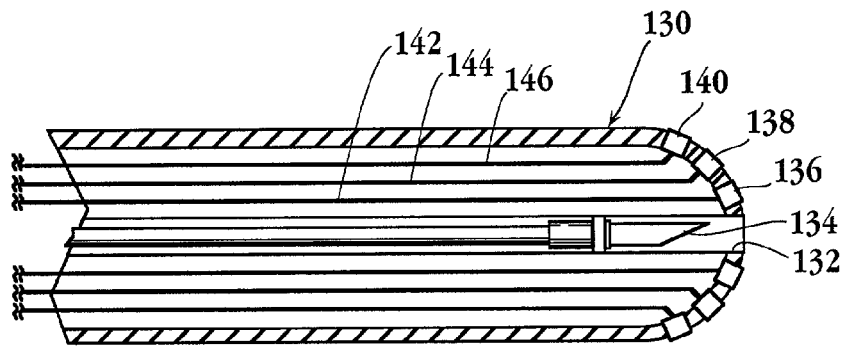
FIG. 12A is a cross-sectional view of an embodiment of a probe with a working element and sensors, showing the working element in a retracted position.
Figure 12B:
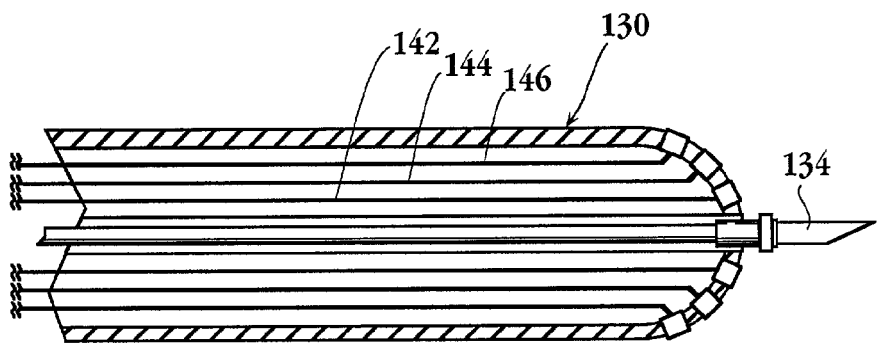
FIG. 12B is a cross-sectional view of an embodiment of a probe with a working element and sensors, showing the working element in an extended position.
Figure 13:
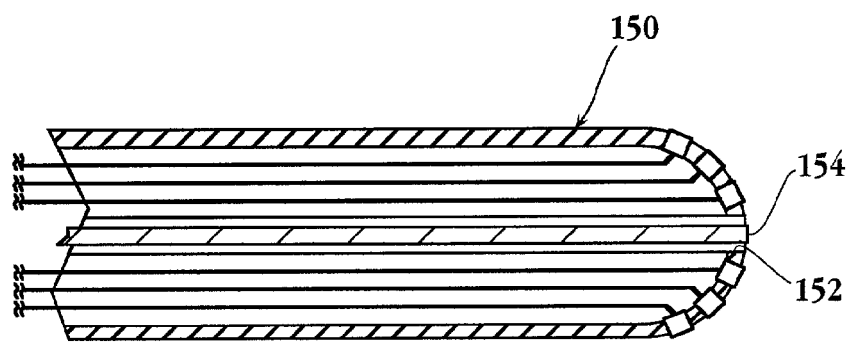
FIG. 13 is a cross-sectional view of an embodiment of a probe with a working element and sensors, showing the working element in a retracted position.

FIGS. 12A, 12B, and 13 illustrate embodiments of distal end probe assemblies for delivering a therapeutic stimulus to tissue. FIG. 12A is a cross-sectional view of a distal end probe 130 that has a rounded contact surface with a central lumen 132 through which a needle 134 can be extended. In one embodiment, a therapeutic solution is administered from a reservoir in the actuator 24 (FIG. 1) into the target tissue through a lumen (not shown) of the needle 134. The distal end probe 130 includes electrodes, or sensors, 136, 138, and 140. The electrodes serve as sensors as previously described with reference to other embodiments, and communicate with a control unit, as previously described, through conductors 142, 144, and 146.

In FIG. 12A, the distal end probe 130 is in a deployment configuration with the needle 134 in a retracted position wherein the distal end of the needle is received within the lumen 132 of the distal end probe 130. The needle 134 may be axially slidable in the lumen 132 of the distal end probe 130. An operator may control movement of the needle 134 along the lumen 132 manually, under control of a control unit (28 in FIG. 1), or through any other means known in the art. FIG. 12B shows the distal end probe 130 in a treatment configuration with the needle 134 advanced distally into an extended position. In one embodiment, the needle 134 may be advanced after the sensors 136–140 detect surface contact with a patient's tissue. This will advance the needle 134 into the tissue, facilitating delivery of a therapeutic stimulus, e.g., injection of a tissue-damaging agent to create a cardiac lesion in treating atrial fibrillation.

In various other embodiments, working elements other than needles may be employed. The working element can retract into the distal end probe in the lumen, or can be fixed in a position. Various working elements can be used to perform various therapeutic and diagnostic procedures. For example, FIG. 13 is a cross-sectional diagram of a distal end probe 150 that includes an optical fiber 154 in a central lumen. The optical fiber 154 delivers a pulse of laser light as a therapeutic stimulus. In another example, needle 134 acts as an RF electrode causing localized thermal injury in the tissue surrounding the needle.

In one embodiment, a distal end probe such as 130 or 150 is maneuvered, e.g., at the tip of a catheter, to a selected target site. During this maneuvering, the user may track the probe fluoroscopically, according to known methods. When the probe is at or near the target site, the user views a display, such as the ones previously described, to determine the angle of contact and/or depth of contact between the distal end probe and the tissue surface, and also to monitor physiological data. The user continues to position the distal end probe until the desired position is achieved. For example, if the distal end probe encounters a trabecula, attempts to improve the contact area by rotating the catheter shaft or adjusting the axial force applied to the shaft may not significantly improve the indicated degree of contact. In this case, the user may simply move the probe to another region and attempt to position the distal end probe again. The user may also select a site and position based on the physiological data, such as EKG data.

Figure 14:
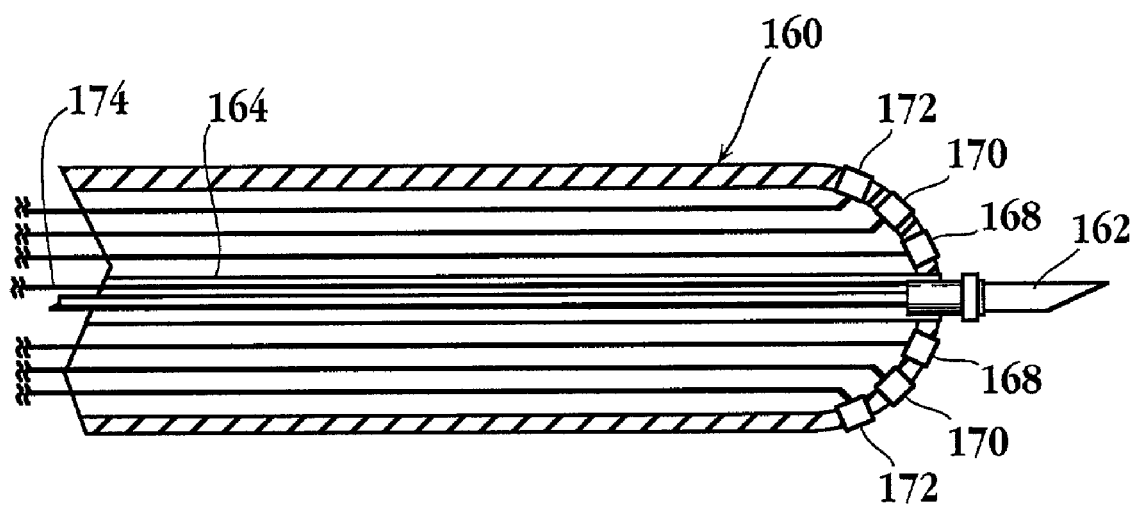
FIG. 14 is a cross-sectional view of an embodiment of a probe with a working element that is a sensor.

FIG. 14 is a diagram of an embodiment including a distal end probe 160 and a working element 162 in a lumen 164. The working element 162 may be a needle for delivering a drug, cells, or creating an injury using mechanical or other means. In other embodiments, the working element can be any one of any of a variety of working elements used in conjunction with catheters to perform various medical procedures. The distal end probe 160 includes electrodes, or sensors, 168, 170, and 172. The electrodes 168, 170, and 172 function similarly to the electrodes 136, 138, and 140 described with reference to FIG. 12A. The working element 162 is connected to the coupling 174, which transmits physiological data collected by the working element 162 from tissue the working element is in contact with. In one embodiment, the physiological data is EKG data. The availability of the EKG information from the working element 162 along with the position and/or EKG information from the electrodes 168, 170, and 172 is very useful for obtaining very site-specific information about tissue during a procedure. For example, in the case of non-transmural infarcts, an infarcted area can be isolated between the endocardium and the epicardium. As the working element progresses through the tissue, the EKG signal from the working element gives an accurate indication of relative tissue health at the site of the working element. Thus, information that is not available from the tissue surface becomes available. There may be no electrical activity on the endocardium, but as the working element is advanced through the tissue, electrical activity may be detected closer to the epicardium. Hence, a therapeutic agent may be delivered through a needle 162 to treat tissue and the same needle 162 can be used to monitor physiological data pertaining to the tissue as it is being treated.

Figure 29:
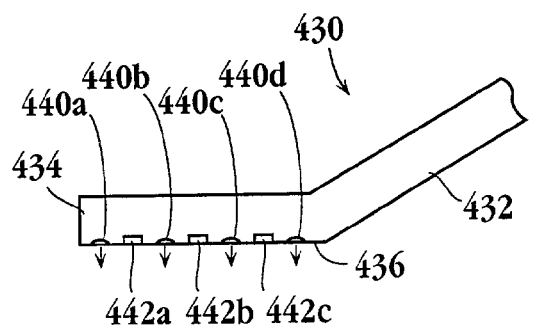
FIGS. 29–32 are top views of tissue treatment devices having tissue-contacting members in accordance with other embodiments of the invention.

FIGS. 12–14 illustrate embodiments employing a single needle. It should be understood that the invention may be practiced with a plurality of needles. The needles may communicate with a common reservoir of injectate, or may be used to deliver different injectates. If the needles are retractable during deployment, they may be deployed individually or with a common deployment mechanism. If multiple needles are employed, they need not all be oriented for deployment distally from a distal end of the injectate delivery device. For example, they may be spaced along a length of an elongate tissue-contacting member (e.g., member 434 of FIG. 29 or member 454 of FIG. 30) adapted to position the needles in close proximity to the surface of the target tissue prior to deployment.

Embodiments Employing Needleless Injection

Figure 15:
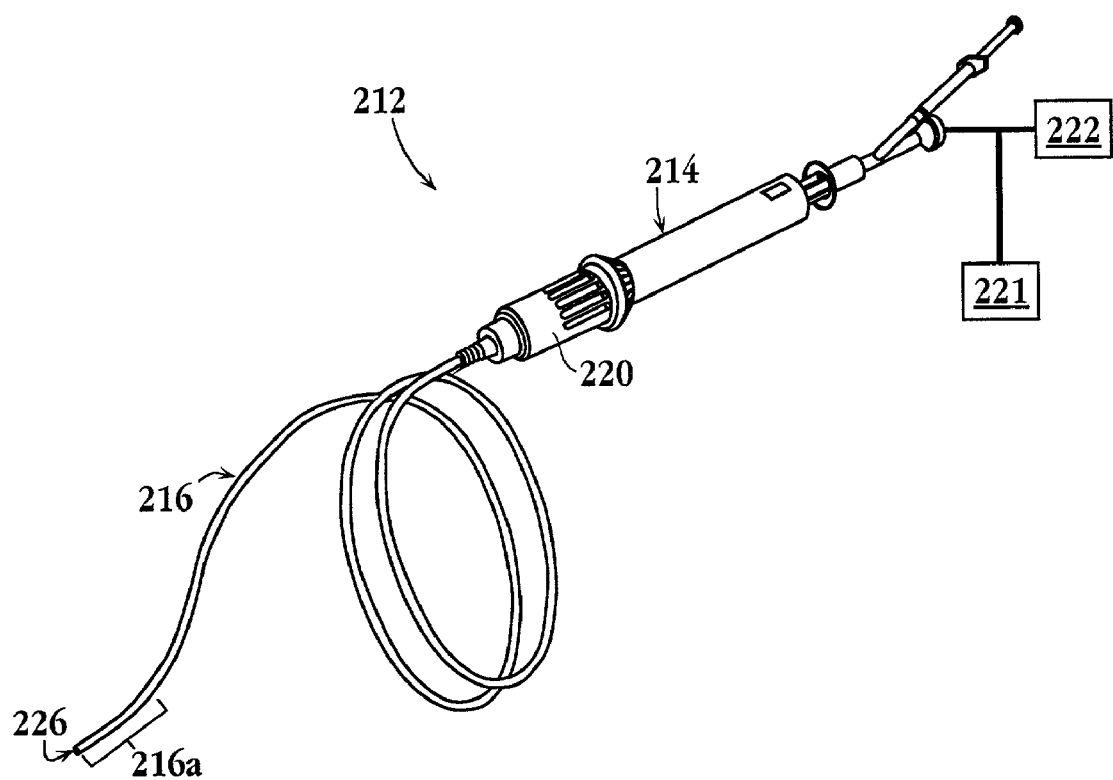
FIG. 15 illustrates a steerable catheter-type device for delivering selected diagnostic and/or therapeutic agents to target sites within a selected body tissue using high-energy jets, in accordance with an embodiment of the present invention.

FIG. 15 illustrates a catheter assembly, indicated generally by the reference numeral 212, in accordance with another embodiment of the invention. The catheter assembly 212 (or even just selected aspects thereof) can be used instead of the apparatus 14 or 15 of FIGS. 1 and 2, respectively, (or selected aspects thereof) in the embodiments discussed above. Likewise, aspects of the apparatus 14 and 15 may be used in conjunction with the catheter assembly 212 and other embodiments discussed below.

Figure 25:
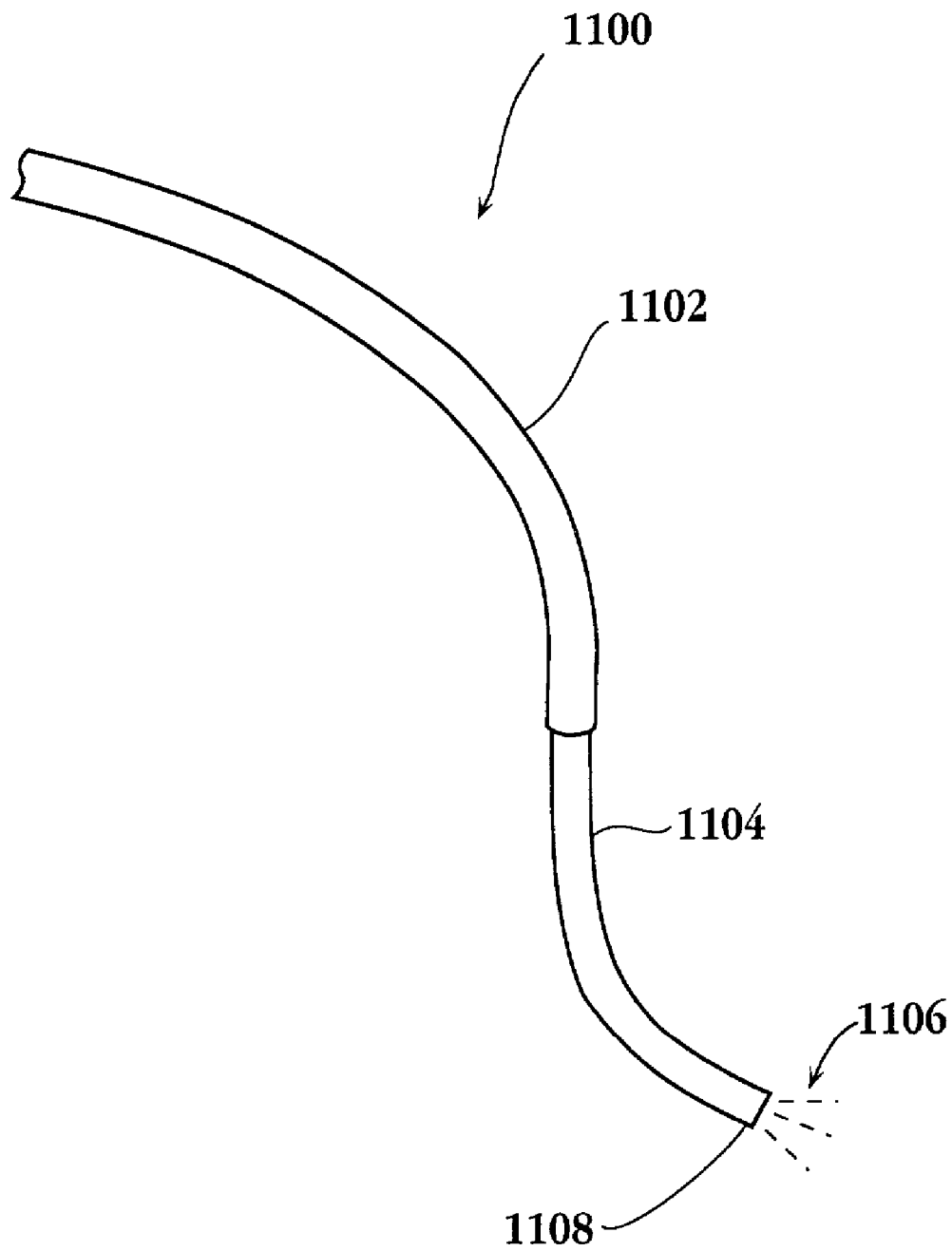
FIG. 25 illustrates an example of the invention where the device is combined with a steerable catheter in one structure.

The catheter assembly 212 of FIG. 15 includes a hand unit 214 attached to a steerable catheter shaft or jacket 216 having a controllably deflectable distal-end portion, as at 216a. Steering of the catheter assembly can be accomplished in a variety of ways. For example, the catheter assembly can include steering components like those disclosed in U.S. Pat. No. 5,876,373, entitled "Steerable Catheter," to Giba et al.; and/or in U.S. Pat. No. 6,182,444, entitled, "Drug Delivery Module," to Glines et al.; and/or in published European Patent Application No. EP 0 908 194 A2; each of which is incorporated entirely herein by reference. In one exemplary arrangement, a conventional pull wire (not shown) is secured at a distal tip of the jacket and extends through a wire-guide channel, formed longitudinally through a sidewall of the jacket, to the hand unit, whereat the wire's proximal end is coupled to a deflection or steering actuator assembly. Rotation of a deflection knob, such as 220, which is threadedly mounted along a forward end of the hand unit, causes the pull wire to be pulled backward, and/or the jacket to be pushed forward, relative to one another, thereby inducing deflection of the distal end of the jacket. Rather than running the pull wire through a channel extending through a sidewall of the jacket, another embodiment provides the pull wire extending longitudinally along an interior sidewall of the jacket. An advantage of the steerable catheter embodiment of the present embodiment over Giba's steerable catheter is the omission of the third inner tool, housed within the second, steerable catheter of Giba. Embodiments of the present invention provide for a unified structure of the tool and steerable catheter making the device simpler, more easily operated, and less costly to manufacture than Giba's triaxial, or coaxial arrangement. Another embodiment of the invention provides for a single catheter unified system where the jet device is integrated into a steerable catheter and omitting the outer, non-steering sheath catheter of Giba, discussed above. Alternatively, the inner tool or fiber optic of Giba may be omitted resulting in a steerable catheter slidably housed within an outer sheath. Other navigation mechanisms and arrangements, suitable for use herein, will be apparent to those skilled in the art. For example, the catheter shaft or jacket can be configured with a fixed shape (e.g., a bend) at its distal end to facilitate navigation as described in application Ser. No. 08/646,856 by Payne filed May 8, 1996, entirely incorporated by reference herein. Another embodiment of the present invention provides for an arrangement that includes a dual steering mechanism where both the inner and outer catheter are steerable with either or both catheters steering as a result of either or both having a pull wire or a pre-shaped member. FIG. 25 illustrates a double steerable catheter device 1100, having a first outer steerable catheter 1102 slidably housing a second inner catheter 1104 having a jet discharge tip 1106 located on its distal end 1108.

Jacket 216 is dimensioned to be placed in the vasculature of a subject and navigated therethrough until the distal tip is disposed proximate a surface or wall region of a selected tissue or organ, e.g., within about 5 mm from a surface within a heart chamber (such as the endocardial wall within the heart's left ventricle). The outer diameter of the catheter jacket is not critical, provided only that it can be navigated to a desired site within a subject body. Suitable catheter jackets range in size, for example, from about 3 French to about 9 French. One preferred catheter jacket is 7 French. Suitable catheter jackets are available commercially, for example as guiding catheters and diagnostic catheters from Bard Cardiology, Cordis, and Schneider Worldwide. Certain preferred jackets from such sources include fixed shapes at their distal end, instead of pull-wire steering mechanisms.

Visualization enhancement aids, including but not limited to radiopaque markers, tantalum and/or platinum bands, foils, and/or strips may be placed on the various components of the catheter assembly, including on the deflectable end portion 216a of catheter jacket 216. In one embodiment, for example, a radiopaque marker (not shown) made of platinum or other suitable radiopaque material is disposed adjacent the distal tip for visualization via fluoroscopy or other methods. In addition, or as an alternative, one or more ultrasonic transducers can be mounted on the catheter jacket at or near its distal tip to assist in determining its location and/or placement (e.g., degree of perpendicularity) with respect to a selected tissue in a subject, as well as to sense proximity with, and/or wall thickness of, the tissue. Ultrasonic transducer assemblies, and methods of using the same, are disclosed, for example, in published Canadian Patent Application No. 2,236,958, entitled, "Ultrasound Device for Axial Ranging," to Zanelli et al., and in U.S. Pat. No. 6,024,703, entitled, "Ultrasound Device for Axial Ranging," to Zanelli et al., each of which is incorporated entirely herein by reference. In one embodiment, for example, two transducers are angle mounted at the distal tip of the catheter shaft in the axis or plane of pull-wire deflection. This construction permits an operator to determine, by comparing signal strength, whether the catheter tip region is perpendicular to a selected tissue surface or wall. Additionally, this two-transducer arrangement provides an operator with information useful for determining an appropriate adjustment direction for improving perpendicularity, as compared to single-transducer arrangements that, while capable of indicating perpendicularity by signal strength amplitude, are generally incapable of indicating a suitable direction in which to move the tip to improve perpendicularity. In a related embodiment, third and fourth transducers (not shown) are added, off of the deflection axis, to aid an operator with rotational movement and rotational perpendicularity in the non-deflecting plane of the subject tissue surface. Additional details of the just-described embodiment are provided in co-pending U.S. patent application Ser. No. 09/566,196, filed May 5, 2000, entitled, "Apparatus and Method for Delivering Therapeutic and Diagnostic Agents," to R. Mueller; incorporated entirely herein by reference. Ultrasonic transducers may, preferably, be substituted with one or more force contact transducers as described in U.S. Provisional Patent Application No. 60/191,610, filed Mar. 23, 2000 by Tom, entirely incorporated by reference herein.

Figure 26:
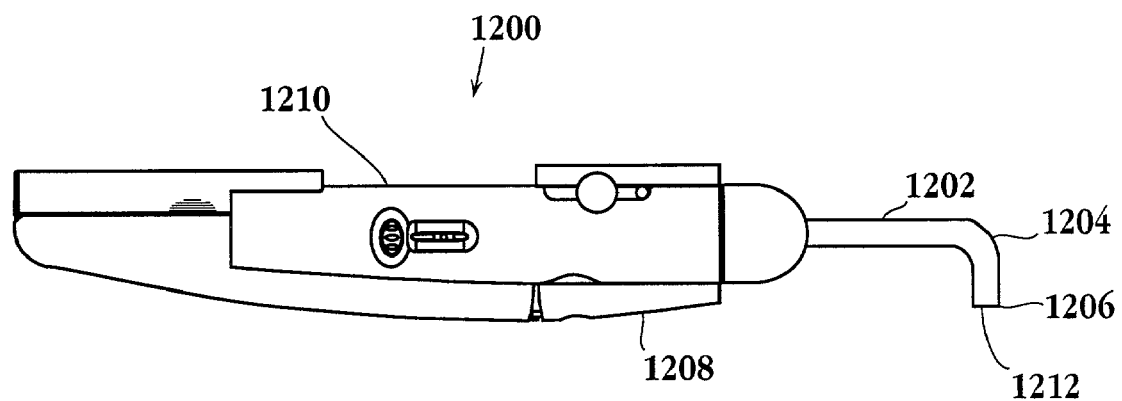
FIG. 26 illustrates an example of the invention where the device is combined with a first steerable catheter in one structure which resides in a second steerable catheter having an axial lumen where the first steerable catheter is slidably maintained.

With respect to hand held, open surgery devices, it is often important to insure that proper contact force is created between the device and a target tissue before discharging the device. Otherwise, the device may inadvertently discharge as it is manipulated towards a target tissue, or it may, in the case where too much force is applied, cause perforation of a tissue that is thinned out as a result of distention caused by excessive force. A force sensing interlock may be incorporated into the invention thus only permitting discharge when such force is within a certain range, both minimally and maximally. For example, ultrasound transducers, force contact transducers, and mechanical interlocks having a minimal and maximal limit. Consequently, hand held needleless hypodermic injector devices, such as those described in U.S. Pat. Nos. 3,057,349, 3,859,996, 4,266,541, 4,680,027, 5,782,802, each entirely incorporated by reference herein, lacking interlocks altogether, or only providing interlocks that activate at a minimum threshold force, without regard to a maximum force limit, are often inadequate. These handheld needleless injectors are further limited in that their structure is not amenable for use inside of a patient cavity created by open surgery, thoroscopic or other "portal" procedures. For example, each of those disclosures provides for a snub nosed hand-held gun for use against a patient's skin, typically a shoulder region of a human. The present invention provides for an elongated jacket portion of the tool to facilitate reaching inside a remote region of the patient. The tool distal end may further be angled or bent, either fixedly, or by bending on demand, or by remote steering of the distal region of the tool. FIG. 26 illustrates an open surgical tool where device 1200 has an elongated jacket portion 1202 having a bend portion 1204, ending in jet tip 1206 located at distal end 1212 which is where liquid is ejected when actuator 1208 is compressed thereby causing a liquid reservoir located around 1210 to deliver fluid to tip 1206 through a fluid conduit not shown.

Internal to the jacket is one or more lumens, extending between the jacket's distal and proximal ends. The lumens serve as passages through which one or more selected agents can pass en route to a selected tissue or organ. In the arrangement of FIGS. 16A–B and 17, for example, a single lumen, denoted as 222, extends longitudinally through jacket 216. In another embodiment, shown in FIG. 18, a plurality of elongate tubes, such as 224a–d, extend through a primary lumen 222 defined by the jacket 216. In this latter embodiment, each of the tubes includes an internal longitudinal conduit or channel, defining a respective sub-lumen or delivery lumen through which one or more agents can pass. Advantageously, this configuration reduces the dead volume in the system. Also, the "on/off" response is optimized, and the pressure limit requirement for the conduit can be readily met.

Catheter jacket 216 terminates at a distal-end face, indicated generally at 226, defining one or more narrow outlet ports or orifices, such as 228a–d (FIG. 17). Face 226 is configured with a relatively broad distal surface region of sufficient area to accommodate a desired number of outlet ports such that each port can be placed against, or very close to (e.g., within about 5 mm, and preferably within about 2 mm), a selected wall or surface region of a target body organ or tissue. Accordingly, one embodiment provides the distal-end face as a generally blunt structure with a broad distal surface. For example, in FIGS. 16–18, a cylindrical plate 232 defines the distal-end face, with the plate having a distal surface that is substantially planar. Alternatively, the distal surface can be somewhat curved (e.g., convex). One or more bores extend through the plate, between its proximal and distal broad surfaces, defining outlet ports for the passage of selected agents.

The plate 232 can be secured along the distal-end region of the jacket 216 in any suitable manner. In one embodiment, for example, the plate is attached directly to the distal tip of the jacket, or in a counterbore formed from the distal tip. Another embodiment, shown in FIGS. 16–18, contemplates the use of an intermediate adapter plug or cap, denoted as 234, having a proximal end configured to fit snugly over the outer circumference of a distal-end region of jacket 216. The distal portion of the adapter cap 234 includes an annular counterbore, or stepped region, configured to receive a peripheral region of the plate 232. Adapter cap 234 can be formed of a suitable plastic material, such as polyethylene or nylon, or of a metallic material such as stainless steel, and bonded to the jacket by heat sealing and/or a conventional adhesive, or other bonding means. The outlet port(s) can be formed, for example, by laser boring, photochemical machining, or other suitable technique; or the plate and bores can be formed together as a molded component.

With further regard to the outlet ports, each is adapted for communication with one or more of the agent-delivery lumens extending through the jacket. In a preferred embodiment, there are from about 1–12 outlet ports (e.g., four, in the illustrated arrangement), each having a diameter of no greater than about 0.025"; and preferably within a range of from about 0.00025" to about 0.020" (e.g., 0.006"). The size and orientation of each outlet port serves to direct agents passed through the catheter lumen(s) in an axial direction, or at an angle no greater than about 35 degrees off axis (i.e., relative to the catheter's longitudinal axis at its distal-end region), in the form of a narrow jet or stream. Axially directed jets or streams can help to maximize penetration depth, while angled jets or streams can help to increase the treated area/volume of tissue. Axially directed jets are illustrated in FIG. 16B, wherein four outlet ports are configured to direct an agent passed through lumen 222 (indicated by the large, darkened arrow) axially into a selected tissue 228 as four separate jets or streams (indicated by the four smaller, substantially parallel arrows).

The outlet ports can be configured to achieve desired jet or spray patterns by modifying, for example, the port diameter, length and/or internal shape. The pressure at the port can also be adjusted to influence the patterns. Injection streams can be further modified with secondary injection of additional drug, or a compatible gas, such as $CO_2$ and/or other absorbable gas. Such a gas can be a good accelerator. In addition, a pulsed injection pattern can be employed to capitalize on tissue recoil effects. In these regards, attention is directed to FIG. 20A which shows an exemplary agent-delivery port 268 and a secondary drug or gas port 272 that meets the delivery port 268 at an angle. Also depicted are several exemplary jet or spray patterns, denoted as "A," "B" and "C." Pattern "A" (FIG. 20B) can be achieved by passing an agent through port 268 under pressure, without the use of a secondary port. Pattern "A" is modified to that of pattern "B" (FIG. 20C) by additionally passing an agent or gas through secondary port 272. Pattern "C" (FIG. 20D) is a pulsed spray pattern that can be used to take advantage of tissue recoil effects. This pattern can be achieved by passing an agent through port 268 as rapid, controlled bursts, without the use of a secondary port.

Figure 23A:
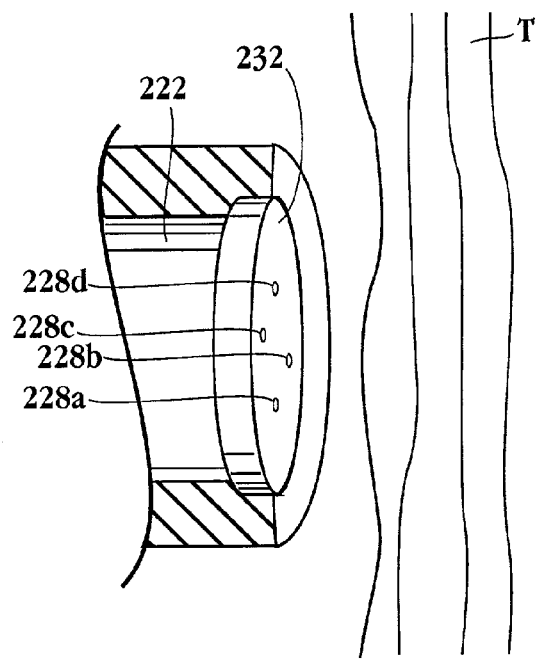
FIG. 23A-D are partial side view of an example of the invention as it is placed near a tissue (23A), urged against the tissue (23B) thus creating a contact force between the device and the tissue, the application of hydraulic force causing ejection of a fluid stream from each outlet port thus propelling the fluid into the tissue (23C), and the removal of hydraulic force and the retention of fluid by the tissue within pockets created by hydraulic erosion (23D).
Figure 23B:
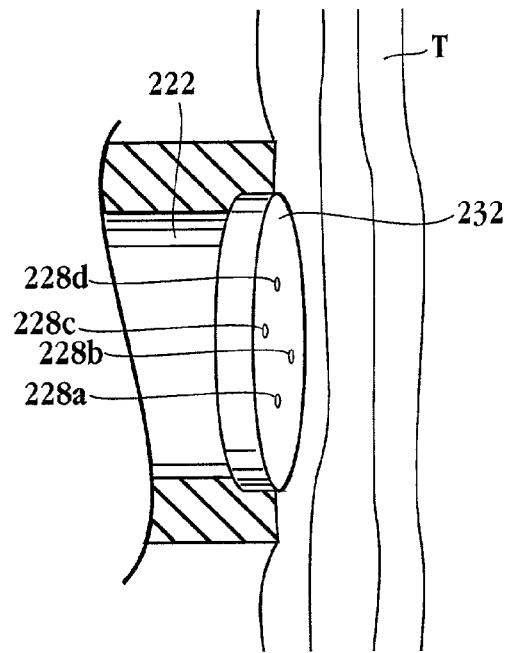
Figure 23C:
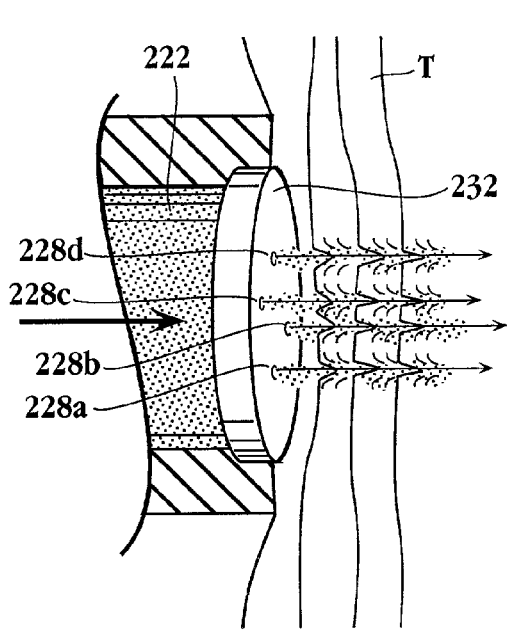
Figure 23D:
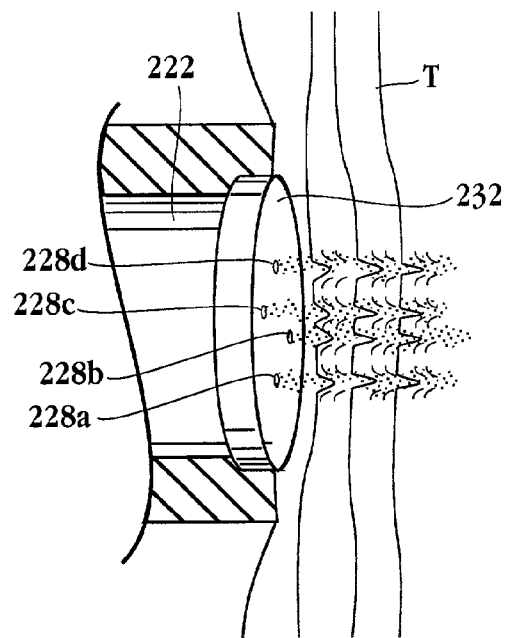

FIGS. 23A–D are partial side views of the apparatus of FIG. 18 as it is placed near a tissue T, such as cardiac tissue (FIG. 23A); urged against the tissue T (FIG. 23B), thus creating a contact force between the device and the tissue T, the application of hydraulic force causing ejection of a fluid stream from each outlet port thus propelling the fluid into the tissue T (FIG. 23C); and the removal of hydraulic force and the retention of fluid by the tissue T within pockets created by hydraulic erosion (FIG. 23D).

In one embodiment, one or more of the agent-delivery lumens and/or outlet ports includes a valving mechanism operable to regulate fluid flow therethrough. Such an arrangement can be useful, for example, for controlling the timing and/or energy of each jet. For example, a quick-action valve can permit controlled, rapid-fire bursts from an outlet port. In one embodiment, a first burst causes a target tissue to recoil and expand, and a subsequent burst then penetrates the tissue while in an expanded state. An exemplary valving mechanism is shown in FIG. 21. Here, an elongate needle plunger 280 has a distal, pointed end 282 that is normally urged against a seat seal 284 by a coil spring 286, thereby closing a respective outlet port. Needle 280 can be withdrawn from seat 284, against the normal bias of spring 286, by pulling on an actuation line (not shown), manually or otherwise, that connects to a proximal end of the needle, thereby opening the port. In another embodiment, a pressure-actuated valving mechanism is employed. Here, the valve is adapted to open automatically upon reaching a certain, predetermined threshold pressure at the port.

Employing a needleless injection system such as that shown in FIGS. 16–19 can reduce the tissue damage often associated with the use of needles. Nevertheless, it should be noted that in certain circumstances a limited amount of tissue damage at or about the injection site may be desirable. For example, where angiogenic agents are being delivered, tissue injury can be beneficial in creating an environment where the action of such agents is enhanced. Likewise, when creating a lesion in cardiac tissue to treat atrial fibrillation, damaging the tissue during the process of injection may enhance lesion formation by the agent being injected. Thus, it will sometimes be desired to configure the outlet ports to produce jet or spray patterns appropriate for effecting a desired amount of tissue damage over a selected area.

In addition to the lumen arrangements described above with respect to FIGS. 16–18, the present invention further contemplates an assembly including one or more elongate tubular elements that can be removably received within a primary lumen defined by an outer elongate sleeve. Each removable tubular element, in this embodiment, defines a sub-lumen or delivery lumen through which one or more selected agents can pass, and includes a distal-end face defining one or more respective outlet ports. Preferably, each tubular element is adapted to slide longitudinally through the primary lumen of the elongate sleeve for placement therein and removal therefrom, as desired.

Figure 24:
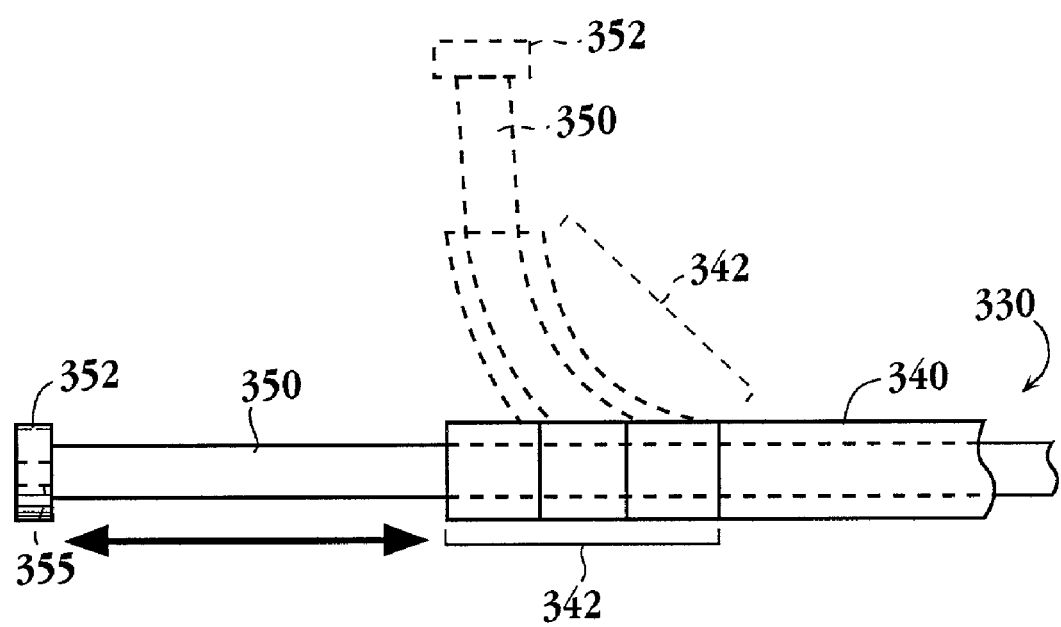
FIG. 24A illustrates an example of the invention where the device is conveyed to the target tissue via a steerable catheter with having an axial lumen where the device is slidably directed towards the target tissue.

FIG. 24 illustrates a steerable treatment device 330 in accordance with one embodiment of the invention. In this embodiment, the steerable treatment device includes a steerable outer sleeve 340 and a delivery catheter 350. The delivery catheter 350 is slidably received in the lumen of the outer sleeve 340. The delivery catheter may include an end member 352 defining a plurality of outlet ports 355 for delivery of a treatment fluid to target tissue at a selected treatment site. A distal length 342 of the guide catheter 340 may be steered by the operator, e.g., by means of control wires (not shown), causing it to deflect from a relaxed state (shown in solid lines) to a curved state (shown in phantom lines). The end member 352 of the delivery catheter 350 can be positioned at a desired location by controlling the axial orientation of the guide catheter 340, the curvature of the distal length 342, and the extent of the end member 352 of the delivery catheter 350 beyond the distal length 342 of the guide catheter 340.

Another embodiment provides such a tubular element extending side-by-side with a guidewire lumen from a proximal to a distal end of an elongate sleeve. In still a further embodiment, such a tubular element is incorporated in a rapid-exchange external-guidewire apparatus. In an exemplary construction of the latter, the tubular element extends longitudinally from a proximal to a distal end of the elongate sleeve, and runs side-by-side with a guidewire lumen along a distal region (e.g., about 3–5 mm) of the sleeve. For example, the present invention can be incorporated in a rapid-exchange apparatus substantially as taught in U.S. Pat. No. 5,061,273, which is incorporated entirely herein by reference. In yet a further embodiment, such a tubular element is adapted to be removed from a lumen extending longitudinally through the sleeve and replaced with a guidewire for facilitating catheter advancement across an anatomical structure such as a heart valve.

In a further exemplary arrangement, a guidewire lumen is coaxial with one or more delivery lumens, with the guidewire lumen at the center and the delivery lumens surrounding the guidewire lumen. It is contemplated that the guidewire lumen can be used to place other elongated devices, if desired, such as ultrasound sensors to measure wall thickness or pressure sensors to infer contact against a wall.

An agent reservoir can be utilized for holding a selected therapeutic and/or diagnostic agent until delivery. The reservoir can be of any suitable type. In one exemplary construction, the reservoir is configured to hold a fluidic agent (e.g., in liquid form) for introduction, using a substantially closed system, into an agent-delivery lumen of the jacket. For example, the agent can be held within a chamber provided inside the catheter jacket, or it can be introduced from an external reservoir (shown schematically as reservoir 221 in FIG. 15), such as a syringe or bag, via a conventional introduction port located along the hand unit or along a proximal region of the jacket. In one embodiment, the hand unit is provided with a fixed internal reservoir for holding a supply of a selected agent to be dispensed. In this embodiment, a supply reservoir, such as a syringe, can communicate with the internal reservoir via a connector provided in the hand unit's outer housing. The connector is preferably a substantially sterile connector, such as a standard Luer-type fitting or other known standard or proprietary connector. In another embodiment, the supply reservoir comprises a syringe, pre-loaded with a selected agent, that can be removably fit into a holding area inside the housing of the hand unit, as taught, for example, in U.S. Pat. No. 6,183,444, entitled, "Drug Delivery Module," to Glines et al, incorporated entirely herein by reference.

A pressure control (shown schematically as pump 222 in FIG. 15) is provided in fluid communication with one or more of the agent-delivery lumens. The pressure control, e.g., a manual or automatic pump, is operable to establish an elevated pressure within such lumen(s) sufficient to propel an agent placed therein toward, and out of, one or more of the outlet ports, thereby forming one or more respective fluid jets or streams capable of penetrating a selected tissue disposed adjacent thereto. In one embodiment, the pressure control is a hand-operable syringe-type pump, connected to one or more lumens along a proximal end of the jacket. Commercially available pressure controls that can be readily adapted for use herein include, for example, power injectors, such as the ACIST Injection System Model CL100 (ACIST Medical Systems), and inflation devices, such as the ARIA or BREEZE inflation devices from Schneider/Namic (Glen Falls, N.Y.). Examples of such injection devices are disclosed in U.S. Pat. Nos. 4,592,742, 5,383,851, 5,399,163, 5,520,639, 5,730,723, 5,746,714, and 5,782,802, each of which is incorporated entirely herein by reference.

An exemplary method of using the above catheter assembly will now be described, wherein the catheter assembly is used for intra-myocardial delivery of a selected therapeutic and/or diagnostic agent. Initially, catheter shaft 16 is percutaneously introduced via femoral or radial artery access. Once arterial access is established, the catheter shaft is slid across the aortic valve and into the left ventricle chamber. The distal end of the catheter shaft is maneuvered so as to be substantially perpendicular to the endocardial wall 228 (FIG. 16B), using fluoroscopic visualization and/or ultrasound guidance, and pressed into contact therewith. A selected agent, in fluidic form, is then introduced into a proximal-end region of lumen 222, and the lumen is pressurized. Under the influence of such pressure, the agent is propelled through the lumen, to and out of one or more outlet ports. In this way, one or more narrow jets or streams are directed at the endocardial wall.

The depth to which each jet penetrates the tissue being treated may depend, at least in part, on the pressure at which the fluid is delivered through the outlet ports and the length of time during which fluid is delivered. In one embodiment, the operating parameters are selected such that the jets penetrate to a tissue depth of at least about 2–10 mm, e.g., about 5 mm. The injection may be carried out over a time period of about 1–15 seconds. In certain embodiments, suitable fluid delivery pressures, i.e., the fluid pressure adjacent the outlet ports, may be about 20–4,500 psi. Lower delivery pressures (e.g., 100 psi or less) may be useful in introducing low viscosity materials in a more superficial portion (e.g., less than 2 mm deep) of the tissue being treated. Higher delivery pressures, such as 400 psi or greater may be employed where deeper tissue penetration is desired.

In one embodiment particularly well suited for treatment of atrial fibrillation, delivery pressures are selected to permit the jets to penetrate the entire thickness of the myocardium. Delivery pressures in excess of 100 psi, more likely at least about 400 psi, may suffice; delivery pressures of about 600–2,000 psi are expected to work well. If the jets penetrate the entire thickness of the myocardium, a tissue-ablating agent may be retained throughout the entire thickness of the tissue, creating a fairly precisely positioned lesion which can extend from one surface of the tissue to the opposite tissue surface.

This embodiment of the invention can provide a distinct advantage over processes employing needles to inject fluids into the myocardium. If a needle is used to inject an ablating agent into the myocardium, the fluid will exit the needle at a specific location within the tissue wall. As more fluid is delivered through the needle, the thickness of the tissue affected by the delivered fluid will increase. However, the tissue will also tend to diffuse laterally at the same time. As a consequence, a transmural lesion created with a needle-based injection may be significantly wider than necessary. In addition, if the needle is placed imprecisely with respect to the thickness of the myocardium, a standard volume of fluid may not be sufficient to extend from one tissue wall to the other.

If pressurized fluid jets capable of penetrating the entire thickness of the myocardium are used instead of a needle, an operator can be assured that the entire thickness of the tissue will be treated with a predetermined fluid volume. By appropriately orienting the jets with respect to the tissue surface and one another, the width of the affected tissue can be controlled. For example, orienting the outlet ports substantially perpendicular to the endocardial wall 228 (FIG. 16B), the jets may define a transmural path that is much more focused than would be achievable with a needle.

Instead of a catheter-type device, the invention can be incorporated in other percutaneous and/or surgical devices. For example, one embodiment contemplates an endoscope-type device having an elongate shaft with one or more longitudinally extending lumens extending therethrough. As with the catheter-type device, the structure defining each lumen (e.g., the endoscope shaft, or one or more tubes extending through the shaft) is configured to withstand an elevated pressure (e.g., up to 2000 psi) in the lumen. Also, like the catheter-type device, a substantially blunt, distal-end face defines one or more outlet ports communicating with one or more of the lumens, with each of the outlet ports having a diameter of about 0.025" or less (e.g., 0.006"). A pressure control, such as a pump, is provided in fluid communication with one or more of the lumens, operable to establish an elevated pressure within such lumen(s) such that an agent placed therein will be propelled toward, and out of, one or more of the outlet ports, thereby forming one or more respective fluid jets or streams capable of penetrating a selected tissue disposed adjacent thereto Various other details pertaining to agent delivery are substantially like those set forth herein with regard to the catheter-type device.

In an exemplary use, the endoscope-type device of the invention is introduced thoracoscopically or through a thoracotomy to direct high-energy jets at the wall or surface of a selected tissue or organ. For example, one or more high-energy jets can be directed at the epicardial surface of the heart, permitting one or more selected agents to penetrate the myocardial tissue. The surgical device can incorporate a thoracoscopic camera (e.g., a reusable 5 mm camera) axially mounted to provide an operator with a suitable field of view through a lens. This allows the operator to work through a common trocar access port placed, for example, through a patient's chest wall.

It is noted that the above-described methods are merely exemplary in nature. Those skilled in the art will appreciate that the present invention provides for the delivery of selected agents to a wide variety of body organs and regions.

In another embodiment of the present invention, a selected therapeutic and/or diagnostic agent is held within a reservoir at the distal-end region of an elongate shaft and delivered into a tissue by means of ultrasonic energy. Pertinent portions of an exemplary agent-delivery apparatus, which can be incorporated in a catheter-type device or an endoscope-type, such as previously described, are shown in FIG. 19. Here, the distal-end region of a catheter-type device is shown, having an ultrasonic transducer 252 (e.g., a piezoelectric transducer, such as barium titanate, lead zirconate titanate, or the like) disposed across lumen 222. The distal end of the catheter jacket defines a single, relatively large opening, denoted as 256; however, a cap or plug with one or more smaller openings (similar to that described above) can be used instead. The transducer is operable to emit ultrasonic energy, of appropriate intensity (e.g., up to about 6 watts/cm$^2$) and frequency (e.g., up to about 20 MHz), along a generally axial direction toward a wall or surface region of a selected organ or tissue 228 within a subject body. The energy, so applied, is effective to cause an agent 258, held within a holding region near the distal end of the catheter jacket, to move toward and penetrate the tissue wall. In one embodiment, the agent is distributed in a polymer matrix, or other solid or semi-solid form, within the holding region. The agent is maintained in the matrix within the holding region until the time of delivery. Alternatively, the agent (e.g., in liquid or semi-solid form) can be maintained within the holding region until delivery by providing a semi-permeable membrane between the agent and the opening at the distal end of the catheter jacket. Other means for maintaining the agent in the holding region until delivery will be apparent to those skilled in the art.

In another embodiment, a selected therapeutic and/or diagnostic agent is held within a distal-end region of a catheter or endoscope-type device and propelled into a target tissue or organ using a biolistic particle-delivery or bombardment assembly. In one embodiment, the biolistic assembly (e.g., a so-called "gene gun" incorporated along a distal-end region of the agent-delivery device) introduces nucleic acid-coated microparticles, such as DNA-coated metals, into a tissue at high energies. The coated particles can be propelled into the tissue using any suitable means, e.g., an explosive burst of an inert gas e.g., (helium), a mechanical impulse, a centripetal force, and/or an electrostatic force (See, e.g., U.S. Pat. No. 5,100,792 to Sanford et al.; incorporated entirely herein by reference). In an exemplary embodiment, a spark discharge between electrodes placed near the distal-end region of the catheter, proximal of a distal-end agent-holding region, is employed to vaporize a water droplet deposited therebetween, which then creates a shock wave capable of propelling the DNA-coated particles. The technique allows for the direct, intracellular delivery of DNA. The carrier particles are selected based on their availability in defined particle sizes (e.g., between about 10 and a few micrometers), as well as having a sufficiently high density to achieve the momentum required for cellular penetration. Additionally, the particles used are preferably chemically inert to reduce the likelihood of explosive oxidation of fine microprojectile powders, as well as non-reactive with DNA and other components of the precipitating mixes, and display low toxicity to target cells (See, e.g., Particle Bombardment Technology for Gene Transfer, (1994) Yang, N. ed., Oxford University Press, New York, N.Y., pages 10–11, incorporated entirely herein by reference). For example, tungsten and/or gold particle microprojectiles can be employed to achieve adequate gene transfer frequency by such direct injection techniques. Alternatively, or in addition, diamond particles, as well as glass, polystyrene and/or latex beads can be used to carry the DNA. The DNA-coated particles can be maintained in the agent-holding region by any suitable means, e.g., precipitated on the distal face of a carrier sheet suspended across a lumen at or near the distal end of the jacket. In this latter embodiment, the propulsion means propels the DNA-coated particles from a distal face of the carrier sheet into a selected target tissue or organ adjacent thereto.

Figure 22:
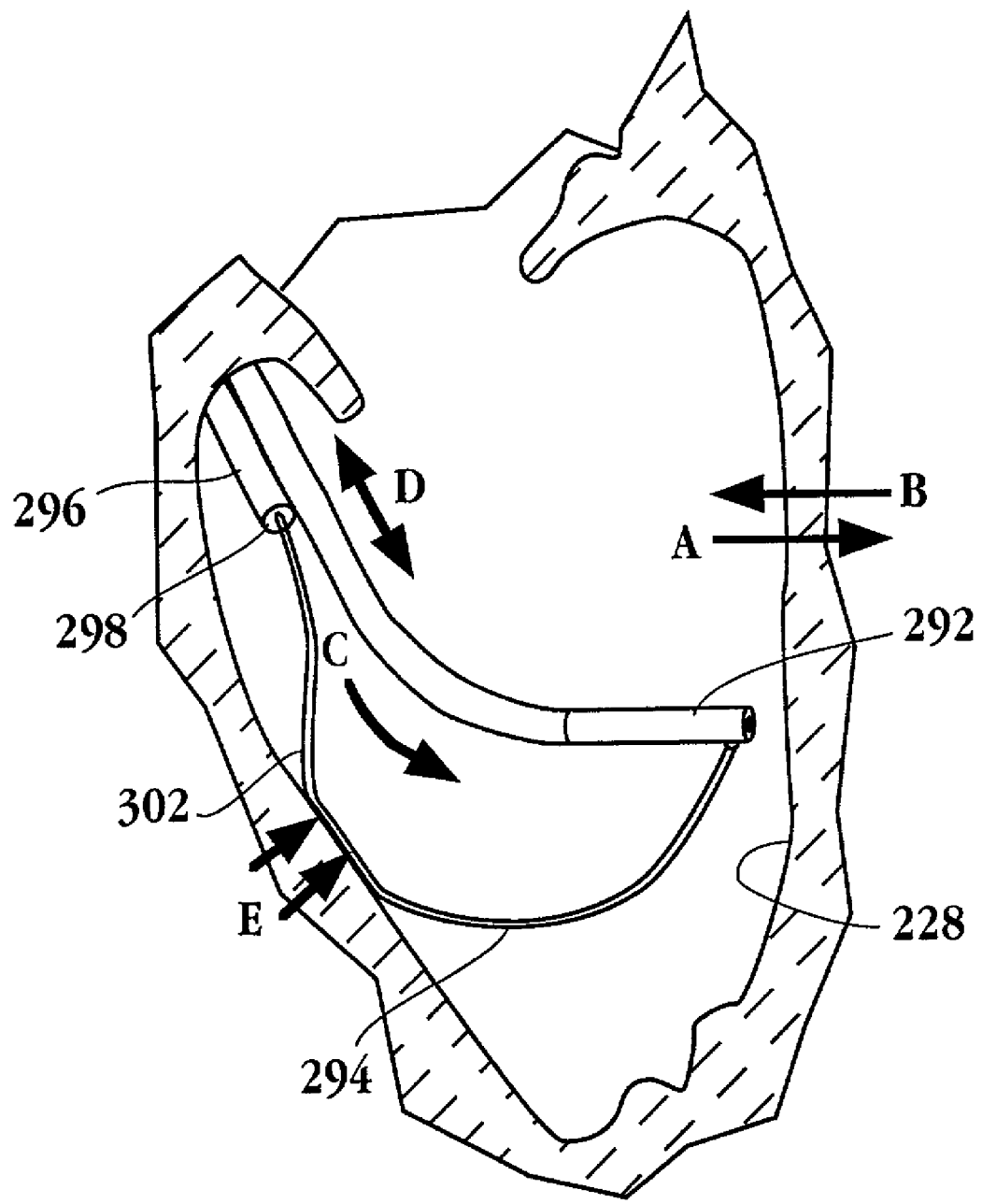
FIG. 22 shows a portion of a steerable catheter positioned with its distal end adjacent a target region of an endocardial wall of a patient's left ventricle, with the catheter being adapted to maintain its distal end at such position notwithstanding "action-reaction" forces due to high-energy jets emanating therefrom that would tend to push it away from the wall.

It will be appreciated that, especially with regard to catheter-type delivery apparatus, an agent directed from a distal end of the apparatus with sufficiently high energy may cause such end to move away from a target tissue wall or surface. FIG. 22, for example, shows a portion of a steerable catheter 292 having a distal end positioned adjacent a target region of an endocardial wall 228 of a patient's left ventricle 294. Arrows "A" and "B" depict an "action-reaction" phenomenon, with (i) arrow "A" representing an injection force provided by one or more high-energy fluid jets or streams directed against the wall 228, with the jet(s) carrying, for example, an angiogenic agent (e.g., "naked" DNA), and (ii) arrow "B" representing a resultant, oppositely-directed force tending to push the distal tip of the catheter away from the endocardial wall. To counter the latter, means are provided for maintaining the distal end of the catheter proximate the endocardial wall. In the illustrated embodiment, a secondary lumen 296 extends longitudinally along the catheter and terminates at a distal orifice 298, short of the catheter's distal end (e.g., by between about 1–4 cm). An elongate wire 302 is slidably received within the secondary lumen 296 and has its distal end attached to the catheter at, or near, the catheter's distal end. From a remote (proximal) location, wire 302 can be moved between a retracted position, with the distal region of the wire positioned closely adjacent the catheter (not shown), and an extended position, with a distal region of the wire extended beyond the secondary lumen's distal orifice so as to bow away from the catheter shaft (shown in FIG. 22). At such extended position, a central region of the bowed portion of the wire presses against a back wall of the ventricle, as at arrows "E," thereby causing a distal region of the bowed portion to urge the catheter's distal end toward the target region of the endocardial wall, as indicated by arrow "C." In another embodiment, a region of the catheter, toward its distal end, is configured with a pre-formed (normal) bend of sufficient stiffness or rigidity to maintain the distal tip of the shaft proximate the target region of the endocardial wall, notwithstanding such "action-reaction" forces. For example, a reinforced external sleeve can be placed over the region "D" of the catheter shaft to impart the desired bend along such region. Alternatively, the bend along region "D" can be inducible from a remote position.

In general, the apparatus and method of the present invention may employ a wide variety of agents, e.g., ranging from active compounds to markers to gene therapy compounds. Exemplary agents, contemplated for use herein, are set forth in U.S. Pat. Nos. 5,840,059; 5,861,397; 5,846,946; 5,703,055; 5,693,622; 5,589,466; and 5,580,859, each incorporated entirely herein by reference. In one embodiment, for example, the invention is employed to deliver one or more genes (e.g., as so-called "naked DNA") into cavities formed into the myocardium of a subject.

In one embodiment, wherein the agent includes DNA, controlled-release preparations are formulated through the use of polymers to complex or absorb the selected gene sequence (with or without an associated carrier, e.g., liposomes, etc.). The agents can be formulated according to known methods to prepare pharmaceutically useful compositions, whereby these materials, or their functional derivatives, are combined in admixture with a pharmaceutically acceptable carrier vehicle. Suitable vehicles and their formulation are described, for example, in Nicolau, C. et al. (*Crit. Rev. Ther. Drug Carrier Syst.* 6:239–271 (1989)), which is incorporated entirely herein by reference. In order to form a pharmaceutically acceptable composition suitable for effective administration, such compositions will contain an effective amount of the desired gene sequence together with a suitable amount of carrier vehicle.

Additional pharmaceutical methods may be employed to control the duration of action. Controlled delivery may be exercised by selecting appropriate macromolecules (for example polyesters, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Another method to control the duration of action by controlled release preparations is to incorporate the agent into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin microcapsules and poly(methylmethacylate) microcapsules, respectively, or in colloidal drug delivery systems, for example, liposomes, albumin microspheres, microemulsions, nanoparticles, or nanocapsules in macroemulsions.

In a typical use, the agent will enter at one or more target regions along a surface or wall of a selected tissue, and diffuse into the tissue, aided by the action of the jets. Advantageously, the high-energy jets provided herein can be utilized even when the distal end of the apparatus (e.g., a catheter shaft) is highly deflected.

Figure 27A:
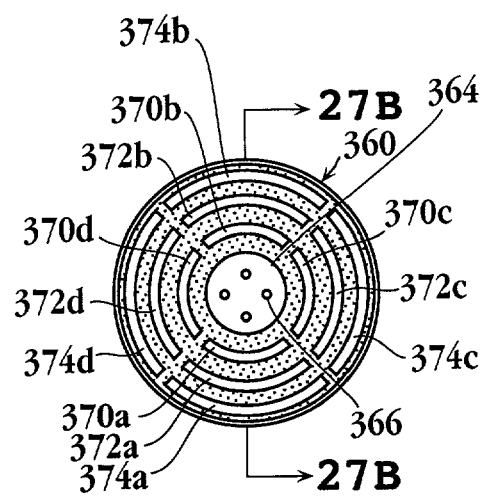
FIG. 27A is an end view of an injection device incorporating tissue contact sensors.
Figure 27B:
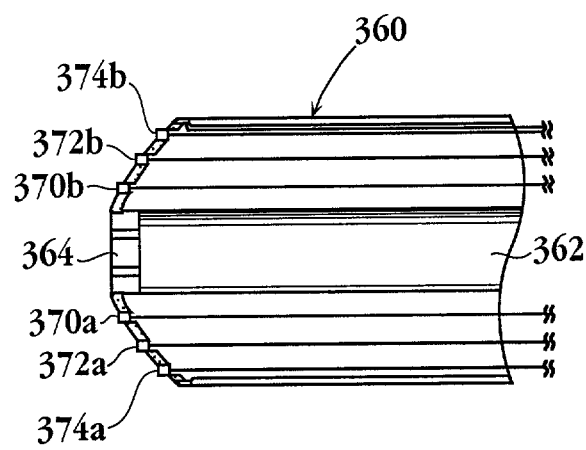
FIG. 27B is a cross-sectional view of the injection device of FIG. 27A.

FIGS. 27A and 27B illustrate a distal length of a treatment apparatus 360 in accordance with another embodiment of the invention that incorporates tissue contact sensors and needleless injection capabilities. In a manner analogous to the distal end probe 116 of FIGS. 10A–B, the treatment apparatus 360 includes a series of sensors 370*a*–*d*, 372*a*–*d*, and 374*a*–*d*. These electrodes 370–374 may be arranged concentrically about the lumen 362 of the treatment apparatus 360. The distal end of the treatment apparatus is rounded to facilitate detection of the degree of penetration of the treatment apparatus 360 in a patient's tissue. Unlike the probe 116 of FIG. 10, the treatment apparatus 360 of FIGS. 27A–B includes a distribution plate 364 adjacent a distal end of the lumen 362. This distribution plate 364 may include a plurality of outlet ports 366, similar to the plate 232 and outlet ports 228 of FIGS. 16–18. The sensors 370–374 permit an operator to detect, prior to injecting an agent through the outlet ports 366, when the distal end of the treatment apparatus 360 (and hence the plate 364) is in contact with the tissue to be treated.

Figure 28A:
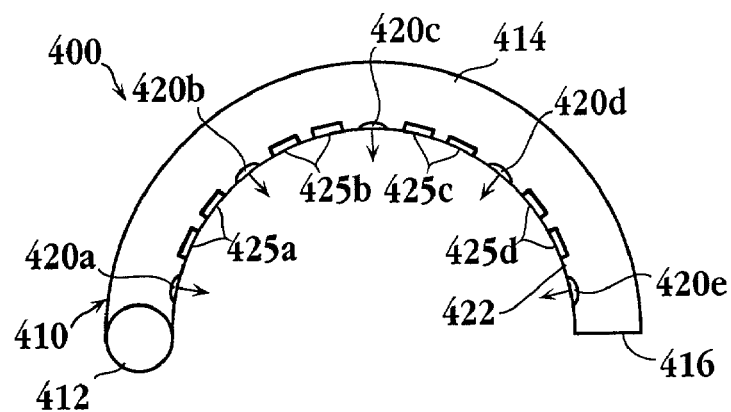
FIGS. 28A–C are top, lateral and front views, respectively, of a tissue treatment device in accordance with still another embodiment of the invention having a flexible tissue-contacting member.
Figure 28B:
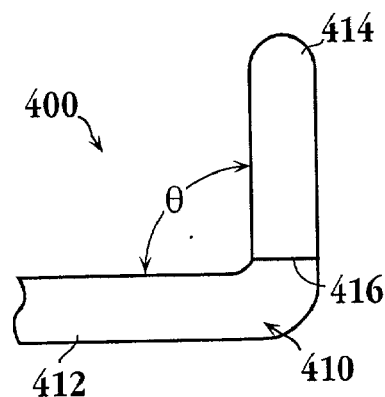
Figure 28C:
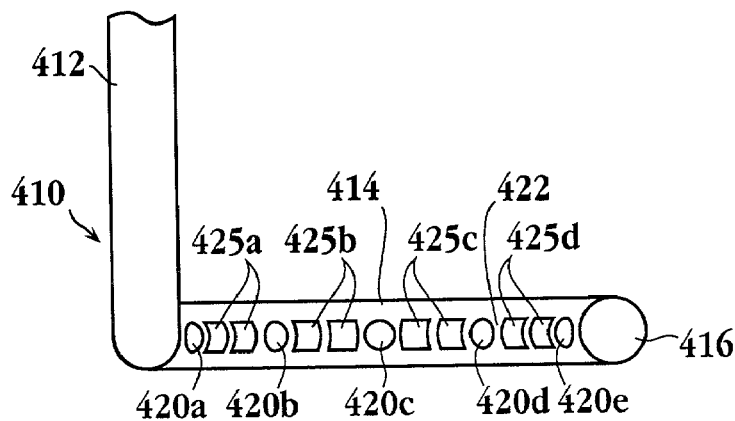

FIGS. 28A–C illustrate a treatment apparatus 400 in accordance with another embodiment of the invention. The treatment apparatus 400 comprises an elongate body 410, e.g., a catheter, having an elongate proximal length 412 and a tissue-contacting member 414. A distal end 416 of the body 410 may be sealed to prevent fluid delivered through the lumen of the body from exiting the distal end 416. In one embodiment, the tissue-contacting member 414 of the body 410 is relatively rigid and retains the curved shape shown in FIGS. 28A–C. The proximal length 412 and the tissue-contacting member 414 may be coplanar. In the illustrated embodiment, which is well suited for thoracic approaches to the exterior of a patient's myocardium, the proximal length 412 and tissue-contacting member 414 meet at an angle θ of about 90°. The angle θ can be varied as desired, with a suitable range depending on the nature of the procedure for which the apparatus 400 is employed and the manner in which the targeted tissue is approached.

If so desired, at least a portion of the length of the tissue-contacting member 414 of the body 410 may be flexible, permitting it to deform from the rest configuration. For example, the tissue-contacting member 414 may be deformed to pass through a steerable outer sleeve (e.g., sleeve 340 in FIG. 24) or an intercostally positioned guide canula, then resiliently assume the curved rest configuration shown in FIGS. 28A–C. The rest configuration of the tissue-contacting member 414 may be selected as desired to permit it to conform to a surface of the tissue to be treated. For example, the shape shown in FIGS. 28A–C may be adapted to encircle a portion of a junction between a patient's myocardium and a pulmonary vein.

A plurality of outlet ports 420a–e are arranged along a tissue-contacting inner surface of the tissue-contacting member 414. Each of these outlet ports 420a–e may be in fluid communication with the lumen of the body 410 so pressurized jets of fluid (shown schematically by arrows in FIG. 28A) can be directed toward tissue in contact with the tissue-contacting surface 422.

The tissue-contacting member 414 may include a plurality of sensors or electrodes 425 adapted to detect surface contact between the tissue-contacting surface 422 of the body 410 and a surface of tissue to be treated. In many of the embodiments noted above, the sensors (e.g., sensors 94–98 of FIGS. 8A–B) are carried at a distal tip of the apparatus. In the embodiment of FIGS. 28A–C, though, the sensors are spaced along the tissue-contacting surface 422, with one electrode pair 420a–d between each pair of adjacent outlet ports 420a–e. By connecting the sensors 425 to an appropriate control system (e.g., control system 28 in FIG. 1), the areas of the tissue-contacting surface 422 in contact with tissue can be detected and displayed in a suitable display (e.g., display 32 in FIG. 1).

FIGS. 29–32 illustrate alternative embodiments employing differently shaped tissue-contacting members. The body 430 of FIG. 29 includes a proximal length 432 and a tissue-contacting member 434 with a generally straight tissue-contacting surface 436. A plurality of outlet ports 440a–d are spaced along the tissue-contacting surface 436 and a sensor 442a–c or a sensor pair (not shown) may be positioned between each adjacent pair of outlet ports 440.

Figure 30:
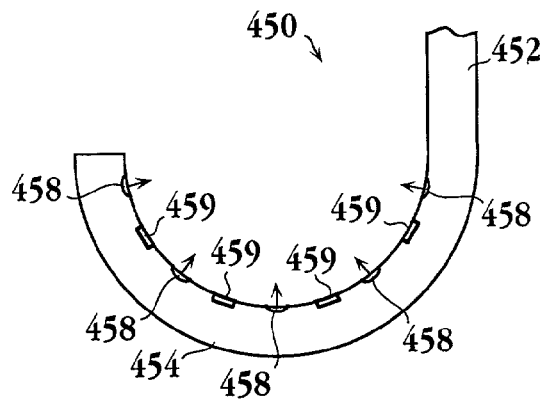

The body 450 of FIG. 30 includes a proximal length 452 and a tissue-contacting member 454 with a generally concave tissue-contacting surface 456. This tissue-contacting member 454 is similar to the tissue-contacting member 414 of FIGS. 28A–C, but the proximal and tissue-contacting members 452 and 454 are substantially coplanar rather than meeting at an angle θ as in FIGS. 28A–C. A plurality of outlet ports 458 are spaced along the tissue-contacting surface 456 and a sensor 459 may be positioned between each adjacent pair of outlet ports 458.

Figure 31:
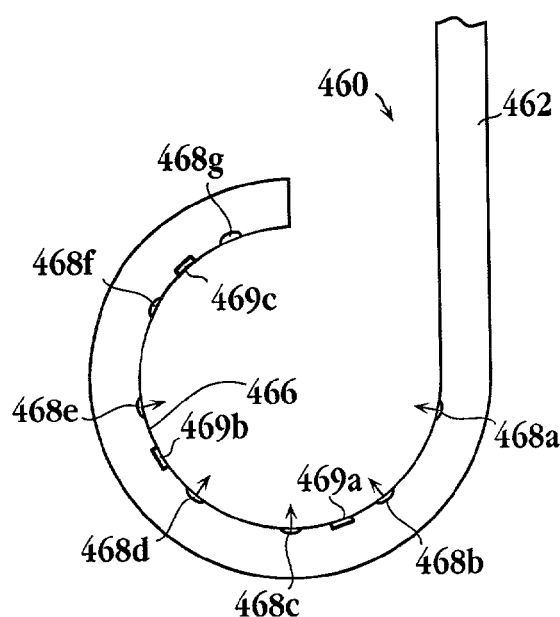

In FIG. 31, the body 460 includes a proximal length 462 and a tissue-contacting member 464 with an arcuate, generally concave tissue-contacting surface 466. The tissue-contacting member 464 of FIG. 31 is similar to the tissue-contacting member 454 of FIG. 30, but extends through a longer arc. A series of outlet ports 468a–g are spaced along the tissue-contacting surface 466. Three sensors 469a–c are spaced from one another along the tissue-contacting surface 466.

Figure 32:
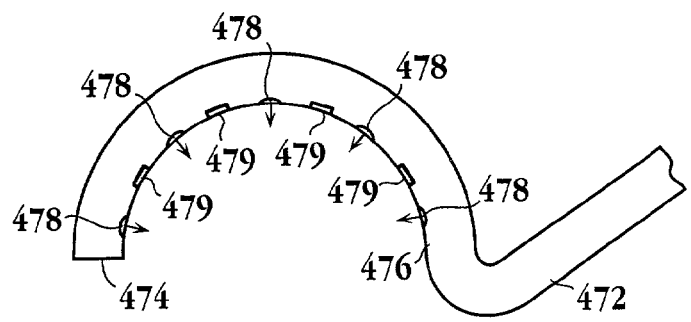

The body 470 of FIG. 32 has a proximal length bending away from the inner, generally concave tissue-contacting surface 476 of the body's tissue-contacting member 474. This can facilitate guiding the tissue contacting surface 476 into surface contact with the tissue to be treated. A plurality of outlet ports 478 are spaced along the tissue-contacting surface 476 and a sensor 479 may be positioned between each adjacent pair of outlet ports 478.

Figure 33:
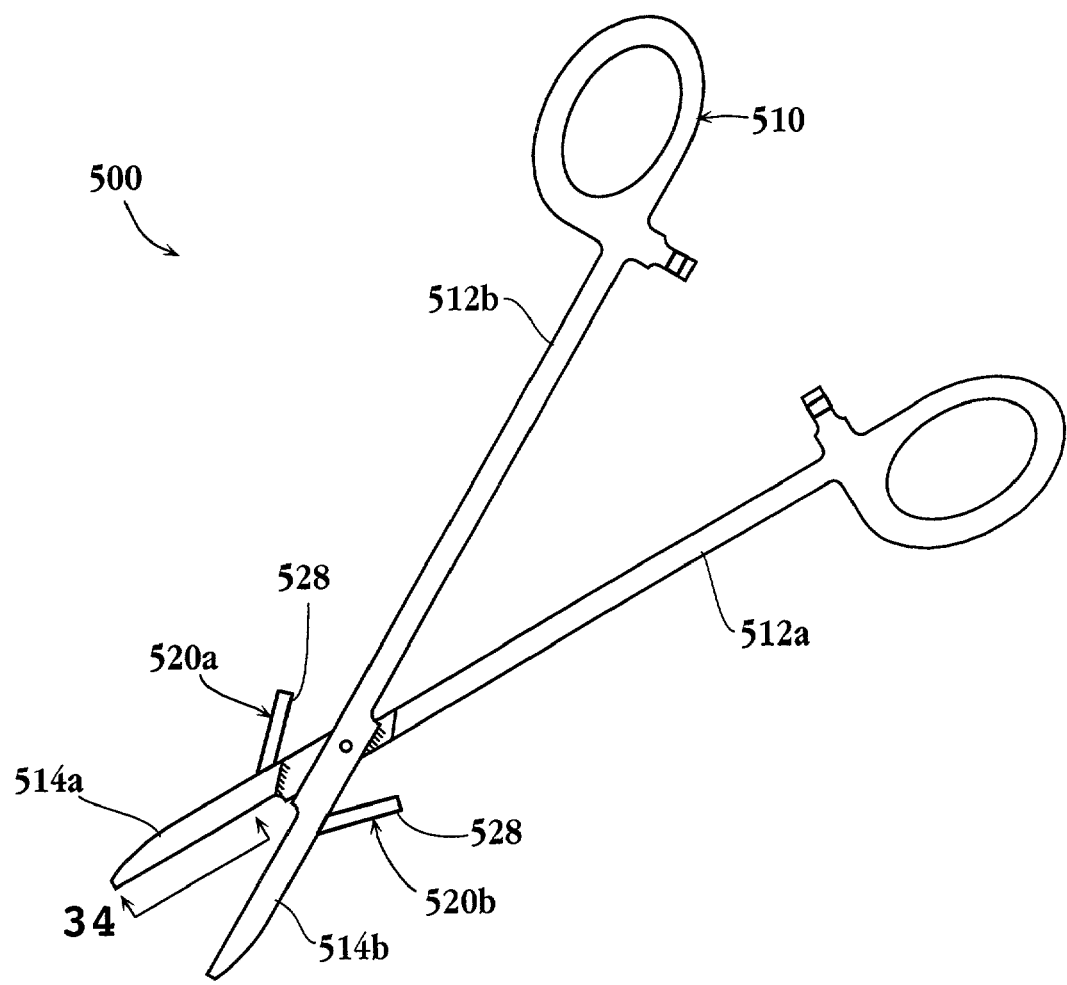
FIG. 33 is a top view of another embodiment of a tissue treatment device.
Figure 34:
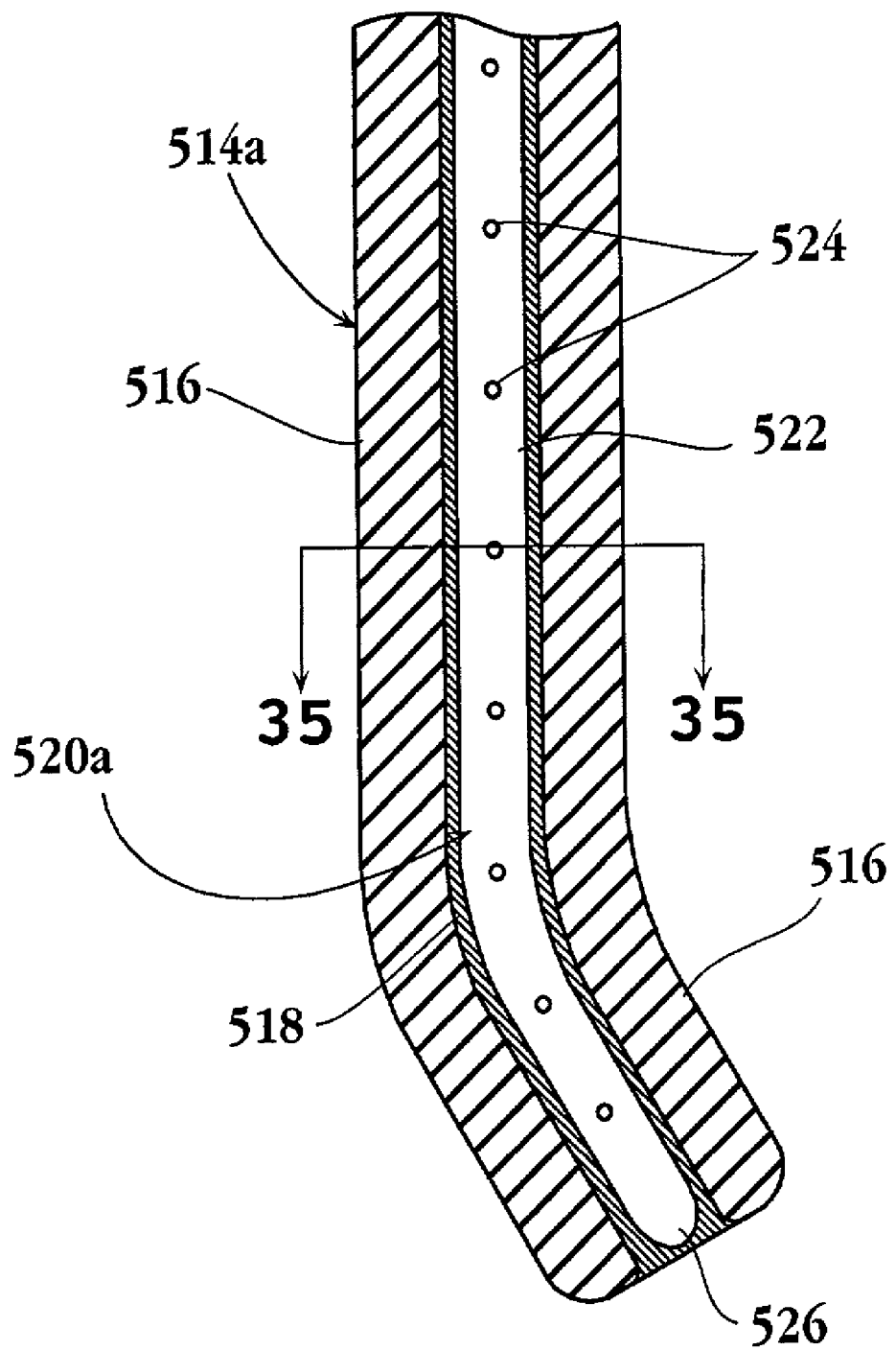
FIG. 34 is a partial side view of the tissue treatment device of FIG. 33 taken along line 34—34 in FIG. 33.
Figure 35:
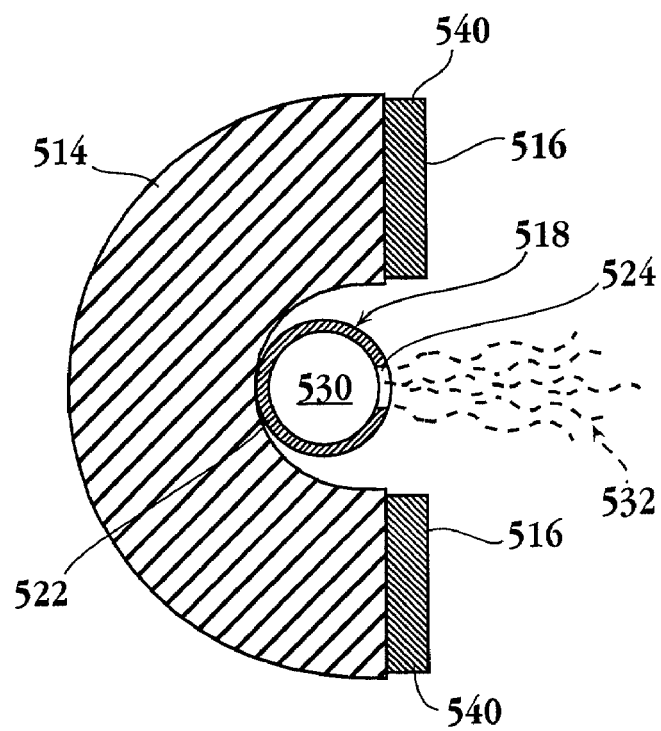
FIG. 35 is a schematic cross sectional view of the tissue treatment device of FIGS. 33–34 taken along line 35—35 in FIG. 34.

FIGS. 33–35 illustrate a tissue treatment apparatus 500 in accordance with another embodiment of the invention. The tissue treatment apparatus 500 generally includes a tissue grasping member 510 and at least one fluid delivery conduit 520. The tissue grasping member shown in FIG. 33 takes the general form of a pair of medical pliers or a medical clamp. The tissue grasping member 510 may include a pair of grasping actuators 512a–b which are pivotally connected to one another. The distal length 514 of each of the grasping actuators 512a–b is adapted to contact tissue and is desirably formed of a biocompatible material, e.g., stainless steel.

Hence, the grasping actuator 512a has a tissue contacting member 514a and the other grasping actuator 512b has a tissue contacting member 514b.

As best seen in FIGS. 34 and 35, the tissue contacting member 514a includes a tissue-contacting face 516 and a recess 518. The recess 518 may take any desired shape. In the illustrated embodiment, the recess 518 comprises a generally U-shaped channel which extends along a center line of the tissue contacting member 514a. This bisects the face 516 into two tissue-contacting surfaces separated by a gap. The gap may be thought of as a plane extending between the two tissue-contacting surfaces.

In one embodiment of the invention, the tissue-contacting face 516 comprises an integral surface of the body of the tissue contacting member 514. In the embodiment shown in FIG. 35, though, the distal face 516 includes a pair of spaced-apart sensors 540. In a manner analogous to the sensors described above, these sensors 540 can be used to detect contact of the tissue contacting member 514 with the patient's tissue and, if so desired, be used to monitor a physiological aspect of the tissue. In one embodiment, the sensors 540 comprise a pair of electrodes which are spaced from one another across the width of the recess 518. By monitoring the current flow between these two electrodes 540, one can detect when the face 516 of the tissue contacting member 514 is in contact with the patient's tissue.

The tissue grasping member 510 is adapted to carry at least one fluid delivery conduit 520 for delivering a fluid to treat a patient's tissue. In the illustrated embodiment, the tissue treatment apparatus 500 includes two fluid delivery conduits 520a–b. The first fluid delivery conduit 520a is associated with the first tissue contacting member 514a and the second fluid delivery conduit 520b is associated with the second tissue contacting member 514b. The fluid delivery conduits 520a–b are in fluid communication with a fluid reservoir (not shown in FIG. 33 for purposes of simplicity). The two conduits 520a–b can be separately connected to the reservoir. Alternatively, the two conduits can be joined proximally of the tissue contacting members 514 and communicate with the fluid reservoir through a common conduit (not shown). In another embodiment, only one of the tissue contacting members 514a–b includes a fluid delivery conduit 520. The other tissue contacting member 514 may simply be used to position tissue against the tissue-contacting face 516 of the member 514 carrying the fluid delivery conduit for treatment, as described below. If one of the tissue contacting members 514 does omit a fluid deliver conduit 520, that tissue contacting member 514 may have a flat tissue-contacting face 516 without a recess 518 to receive the conduit 520.

The fluid delivery conduit 520a has a proximal length 528 which extends proximally of the tissue contacting member 514a and a distal length 522 which is received within and extends along the recess 518. (FIG. 34 only shows the first tissue contacting member 514a, but the second tissue contacting member 514b may have essentially the same structure.) The distal length 522 of the conduit includes a plurality of spaced-apart fluid delivery ports 524. A distal end 526 of the conduit 520 can be sealed to direct all of the fluid delivered through the lumen 530 of the conduit 520 through the ports 524.

The recess 518 in the tissue contacting member 514 is adapted to receive the conduit's distal length 522, or at least the portion of the distal length 522 which includes the outlet ports 524. The distal length 522 may be attached to the inner surface of the recess 518 to keep the distal length 522 in place and orient the ports 524 outwardly from the recess and toward the gap in the face 516 of the member 514. The distal length 522 can be bonded to the inner surface of the recess 518 using a biocompatible adhesive, for example.

The recess 518 is deep enough to permit the outlet ports 524 of the distal length 522 to be spaced inwardly from the tissue-contacting face 516 of the member 514. In the illustrated embodiment, the recess 518 has a depth which is greater than the outer diameter of the distal length 522. The distance between the outlet port 524 and a plane extending across the gap in the forward face 516 can be varied as desired. In one embodiment, the distance is sufficient to ensure that the outlet ports 524 will be spaced away from the surface of a tissue being treated. If the tissue being treated is expected to bulge into the recess, the distance between the port 524 and the face 516 may be greater than if the tissue is not expected to bulge very far into the recess 518 during ordinary conditions of use.

Figure 36:
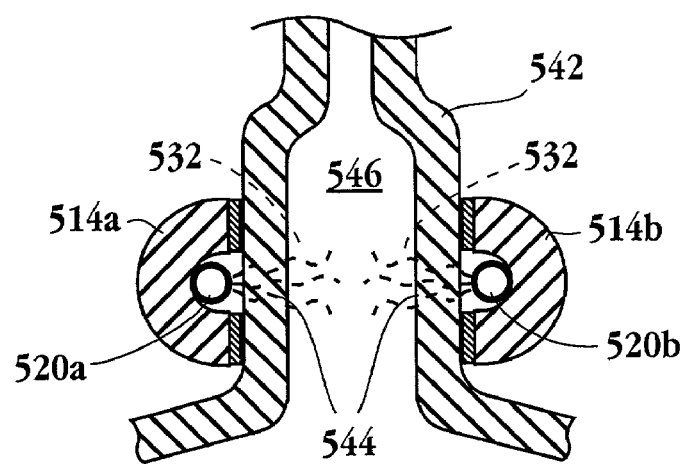
FIG. 36 is a schematic illustration of the device of FIG. 33 being used to treat tissue of a pulmonary vein.

FIG. 36 is a schematic cross-sectional view of the tissue treatment device 500 being used to treat a target tissue 544, exemplified in this case as tissue of a pulmonary vein 542. While the following discussion focuses on the use of the tissue treatment apparatus 500 to treat a pulmonary may, it should recognize that the apparatus 500 can be used in a variety of other contexts to inject a suitable treatment fluid in any tissue which needs to be treated.

The two tissue contacting members 514a–b are placed on opposite sides of the pulmonary vein 542. The grasping actuators 512a–b are moved toward one another to bring the tissue-contacting faces 516 of the tissue contacting members 514a–b against the target tissue 544 of the pulmonary vein 542. In particular, the two opposed tissue contacting members 514 are in contact with the target tissue 544 on opposite sides of the pulmonary vein 542. The fluid delivery ports 524 of each of the fluid delivery conduits 520 are oriented inwardly for the pulmonary vein 542. In the illustrated embodiment, the fluid delivery ports 524 of each conduit 520 are oriented generally toward the other fluid delivery conduit 520.

As shown in FIG. 36, when the tissue contacting members 514 are urged against the target tissue 544, the distal length 522 of each fluid delivery conduit 520a or 520b is spaced a distance from the surface of the target tissue 544. A treatment fluid, e.g., a tissue ablating agent, can be delivered through the conduits 520a–b and directed out of the ports 524 in a series of fluid jets 532. In one embodiment, the pressure of the jets is sufficient to drive fluid through the entire thickness of the wall of the pulmonary vein 542, with an excess volume of the fluid being delivered into the lumen 546 of the vein 542. In another embodiment, the pressure may be reduced to permeate only partially through the thickness of the target tissue 544. Delivering the pressurized fluid jets in this fashion permits the apparatus 500 to treat tissue along lines on opposite sides of the tissue. In the context of treating a pulmonary vein 542 with a tissue-damaging fluid, this can create lesions on opposite sides of the pulmonary vein 524 which extend through the entire thickness of both walls.

Spacing the outlet ports 524 from the tissue being treated can be advantageous in some applications. As noted above, placing the outlet ports directly against the tissue will yield a focused treatment area. Spacing the outlet ports 524 away from the surface of the tissue will permit the fluid jets to disperse into a somewhat wider spray pattern, effectively treating a larger tissue area. In the illustrated embodiment, the width of the spray is con strained by contact of the face 516 against the tissue being treated. While this contact need not be fluid tight, the walls of the recess 518 and the contact between the face 516 and the tissue will limit dispersion of the fluid to a fairly predictable range. In the context of ablating tissue in treating atrial fibrillation, for example, this will yield a lesion in the tissue having a predictable, reproducible width.

The embodiment illustrated in FIGS. 33–36, which includes a pair of opposed tissue contacting members 514a–b, can also help ensure proper positioning of the outlet ports 524 with respect to the tissue being treated. Urging the members 514a–b toward one another will compress the tissue. Urging the members 514a–b against the tissue can pull the tissue more taut, reducing the tendency of the tissue to recoil under the impact of the pressurized jets 532. The force against the tissue should not be too great, though. In one embodiment, the members 514 urge the opposite sides of the pulmonary vein 542 toward one another, but not far enough to come into contact.

In One Embodiment of a Method of Treating Tissue, JJJ

Figure 37A:
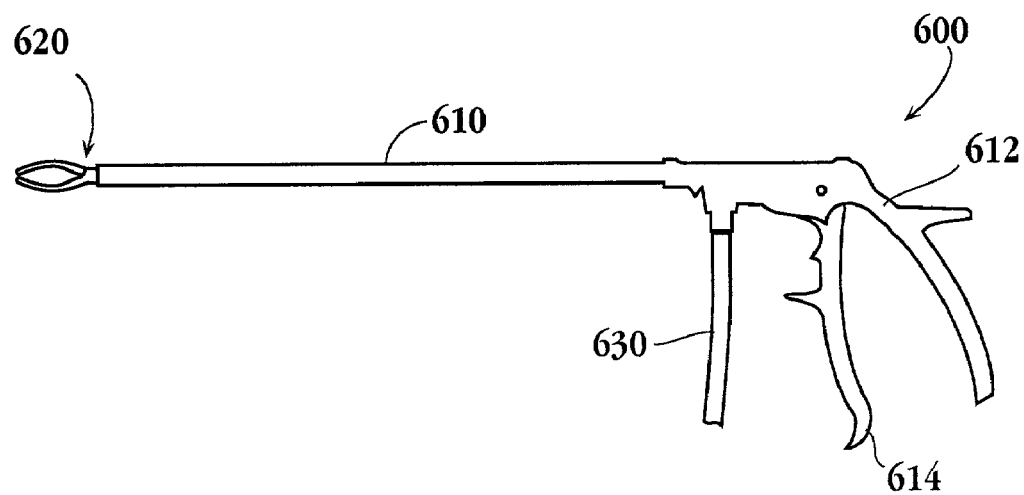
FIG. 37A is a side view of a tissue treatment device in accordance with still another embodiment of the invention.

FIG. 37A illustrates a tissue treatment apparatus 600 in accordance with another embodiment of the invention. This tissue treatment apparatus 600 includes an elongate body 610 with a manually graspable handle 612 adjacent its proximal end and a distal grasping member 620 adjacent its distal end. The body 610 and the distal grasping member 620 may be sized to be introduced into a patient's thoracic cavity through an intercostal incision. The body 610 may comprise a generally rigid tubular member having a lumen extending from the handle 612 to the distal end of embodiment adjacent the distal grasping member 620. The handle 612 may include an actuator 614 which can be used to move the distal grasping member 620 between a closed position (shown in FIG. 37A) which may be used when delivering fluid to treat tissue and an open position (not shown) adapted to receive the tissue to be treated. Movement of the actuator 614 can be translated into motion of the distal grasping member 620 in any desired fashion, e.g., by means of a flexible cable (not shown). A number of grasping tools adapted for endoscopic procedures are known in the art and the mechanisms useful in those devices may be employed to remotely manipulate the distal grasping member 620 of the tissue treatment apparatus 600 of FIG. 37A.

A fluid delivery conduit 630 may be employed to deliver a fluid to treat tissue from a reservoir (not shown in FIG. 37A) to a series of distally located ports. Although not shown in detail in FIG. 37A, the fluid delivery conduit 630 may bifurcate distally to provide a pair of distal lengths similar to the distal lengths 522 of the fluid conduits 520a–b in the previous embodiment.

FIGS. 38A and 38B illustrate the distal grasping member 620 in greater detail. The distal grasping member 620 includes a first tissue contacting member 622a and a second tissue contacting member 622b which can be moved with respect one another between an open position (FIG. 38A) wherein the tissue contacting members 622 are spaced from one another and a closed position (FIG. 38B) wherein the tissue contacting members 622 are closer to one another. A first branch 632a of the fluid delivery conduit 630 may be associated with the first tissue contacting member 622a and a second branch 632b of the fluid delivery conduit 630 may be associated with the second tissue contacting member 622b. The first tissue contacting member 622a may include a first tissue contacting face 624a and the second tissue contacting member 622b may include an opposed second tissue contacting face 624b. If so desired, the tissue contacting members 622 may include a recess for receiving the associated portion of the fluid delivery conduit 630 in a fashion directly analogous to that described above in connection with FIGS. 34–36.

FIGS. 39A and 39B illustrate an alternative distal grasping member 640 that may be used in the tissue treatment apparatus 600 instead of the distal grasping member 620 shown in FIGS. 38A and 38B. The distal grasping member 640 may include a first tissue contacting member 642a having a first tissue-contacting face 644a and a second tissue contacting member 642b having an opposed second tissue-contacting face 644b. A first branch 632a of the fluid delivery conduit (630 in FIG. 37A) may be associated with the first tissue contacting member 642a and a second branch 632b of the fluid delivery conduit 630 may be associated with the second tissue contacting member 642b. The primary distinction between the distal grasping member 640 of FIGS. 39A–B and the distal grasping member 620 of FIGS. 38A–B is that the tissue contacting members 642 of FIGS. 39A–B are inwardly concave, whereas the tissue contacting members 622 of FIGS. 38A–B have a relatively straight tissue contacting face 624. As a consequence, the tissue contacting faces 624 may be generally parallel to one another in the closed orientation (FIG. 38B), defining a relatively straight gap, whereas the distal grasping member 640 has a more elliptical space between the tissue contacting faces 644 in the closed configuration (FIG. 39B).

Figure 37B:
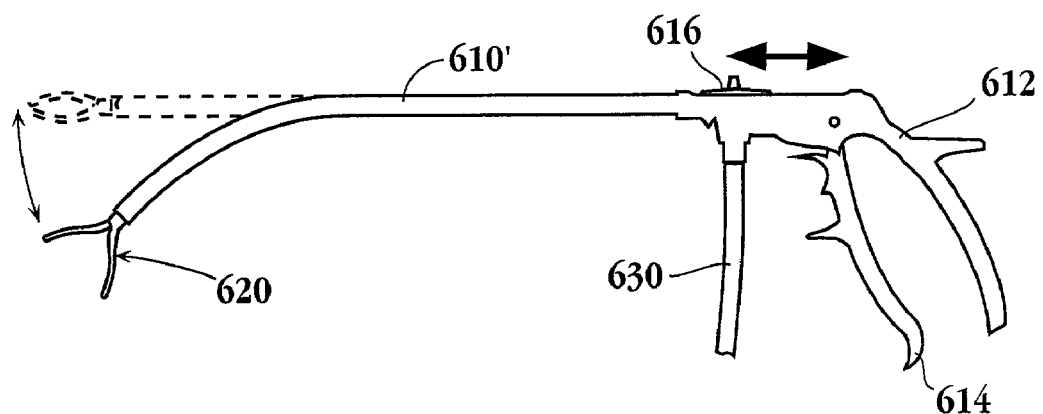
FIG. 37B is a side view of a modified version of the embodiment of FIG. 37A.
Figure 40:
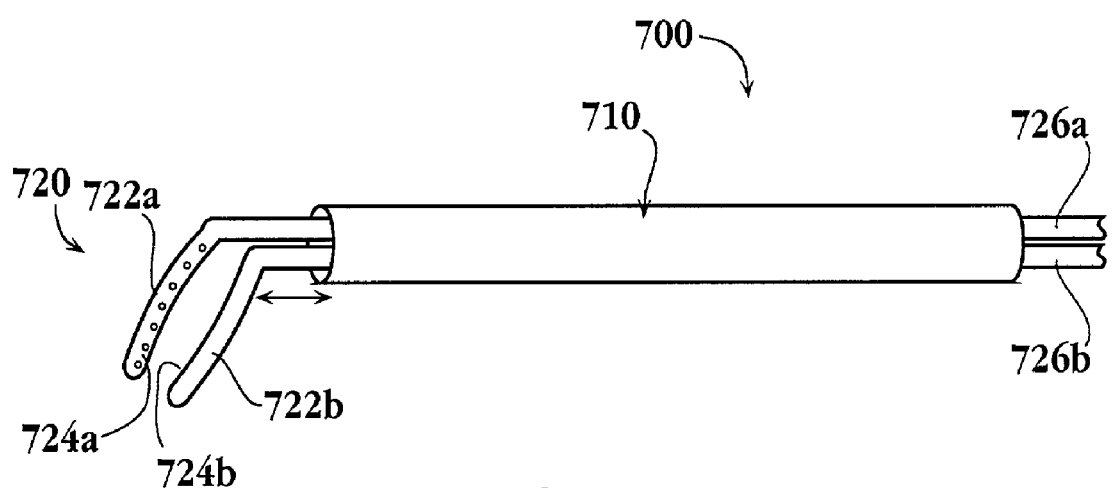
FIG. 40 is a side view of a tissue treatment device in accordance with still another embodiment of the invention.

As noted above, the body 610 of the tissue treatment apparatus 600 shown in FIG. 37A may be generally rigid. FIG. 37B illustrates an alternative embodiment wherein the rigid body 610 is replaced with a more flexible body 610'. If so desired, the tissue treatment apparatus may include a flexure control 616 adjacent the handle 612. The flexure control 616 is connected to the body 610' such that manual movement of the flexure control proximally or distally (as indicated by the arrows in FIG. 37B) can move the body 610' between a deflected position (shown in solid lines) and a variety of straighter positions (one of which is shown in dashed lines). This can facilitate the proper placement of the distal grasping member 620 adjacent the target tissue for grasping and subsequent treatment.

As noted above, forming myocardial lesions to create a "maze" which helps redirect the cardiac electrical impulse can treat atrial fibrillation. In accordance which embodiments of the invention, injecting a tissue-damaging agent into the myocardium may create such lesions. The tissue-damaging agent may comprise any injectable fluid agent which, when injected alone or with another agent into cardiac tissue, will create a lasting, signal-impeding cardiac lesion suitable for the maze approach to treating atrial fibrillation. In certain embodiments, the tissue-damaging agent may comprise a tissue-ablating agent, i.e., a material that will lead to a permanent destruction of a function of the tissue, such as effectively conducting cardiac electrical impulses. The tissue-damaging agent may comprise a liquid, a gas, or both liquid and gas, such as in the embodiment discussed above in connection with FIGS. 20A–20C. For example, the tissue-damaging agent may comprises a fluid ablating agent selected from the group consisting of alcohols (e.g., ethanol), hypertonic saline (e.g., 10–25% wt./vol.), thermally-ablating agents, sclerosing agents, and necrotic antineoplastic agents. Thermally damaging agents may comprise materials that are biocompatible at or near body temperature (e.g., saline, glycerine or ethylene glycol), but are heated so far above or cooled so far below body temperature that their injection will induce permanent tissue ablation. Hot injectates which are hot enough to raise the temperature of the tissue into which it is injected to 50° C.–100° C. should suffice; cold injectates which are delivered at a temperature below 0° C., e.g., minus 0.1–5° C., are expected to work well, too. A variety of sclerosing agents are known in the art and commercially available, including ethanolamine oleate (e.g., ETHANOLIN), sodium tedradecyl sulfate (e.g., SOTRADECOL), ATHOXYSCLEROL, polyethyleneglycol-monododecylether (e.g., POLIDOCANOL), sodium morrhuate, and hypertonic saline with dextrose (e.g., SCLERODEX). Known antineoplastic agents with tissue necrotic effects include CISPLATIN, DOXORUBICIN and ADRIAMYCIN, each of which is commercially available.

Methods of Treating Tissue

The apparatus shown in FIGS. 1–40 and detailed above may be used in a variety of procedures, a number of which are outlined above. Several embodiments of the invention, however, provide methods for treating cardiac arrhythmia. While reference is made in the following discussion to specific apparatus disclosed in the drawings used to treat cardiac arrhythmia, it should be understood that this is solely for purposes of illustration and is not intended to limit the scope of the invention. In particular, devices other than those shown in the drawings or described above may be employed to carry out methods in accordance with the invention, tissues other than cardiac tissue can be treated, and fluids other than tissue ablating agents can be injected into the tissue.

As noted above, forming myocardial lesions to create a "maze" which helps redirect the cardiac electrical impulse can treat atrial fibrillation. In accordance with embodiments of the invention, injecting a tissue-damaging agent into the myocardium may create such lesions. The tissue-damaging agent may comprise any injectable fluid agent which, when injected alone or with another agent into cardiac tissue, will create a lasting, signal-impeding cardiac lesion suitable for the maze approach to treating atrial fibrillation. In certain embodiments, the tissue-damaging agent may comprise a tissue-ablating agent, i.e., a material that will lead to a permanent destruction of a function of the tissue, such as effectively conducting cardiac electrical impulses. The tissue-damaging agent may comprise a liquid, a gas, or both liquid and gas, such as in the embodiment discussed above in connection with FIGS. 20–20c. For example, the tissue-damaging agent may comprise a fluid ablating agent selected from the group consisting of alcohols (e.g., ethanol), hypertonic saline (e.g., 10–25% wt./vol.), thermally-ablating agents, sclerosing agents, and necrotic antineoplastic agents. Thermally damaging agents may comprise materials that are biocompatible at or near body temperature (e.g., saline, glycerine or ethylene glycol), but are heated so far above or cooled so far below body temperature that their injection will induce permanent tissue ablation. Hot injectates which are hot enough to raise the temperature of the tissue into which it is injected to 50°–100° C. should suffice; cold injectates which are delivered at a temperature below 0° C., e.g., minus 0.1–5° C., are expected to work well, too. A variety of sclerosing agents are known in the art and commercially available, including ethanolamine oleate (e.g., ETHAMOLIN), sodium tedradecyl sulfate (e.g., SOTRADECOL), ATHOXYSCLEROL, polyethyleneglycolmonododecylether (e.g., POLIDOCANOL), sodium morrhuate, and hypertonic saline with dextrose (e.g., SCLERODEX). Known antineoplastic agents with tissue necrotic effects include CISPLATIN, DOXORUBICIN and ANDRIAMYCIN, each of which is commercially available.

The tissue-damaging agent may be delivered through an injectate delivery device that an operator can control from a position outside the patient's body. For example, the catheter assembly 212 of FIG. 15 may be employed to inject the agent from the reservoir 221 into the patient's tissue. A tissue-contacting portion of the injectate delivery device will be guided within the patient's thoracic cavity into proximity with the selected region of the heart for treatment. For example, catheter assembly 212 can be introduced into a patient's femoral artery and the catheter shaft may be passed through the aortic valve and into the left ventricle chamber. The distal end 226 of the catheter 216 may be maneuvered using fluoroscopic and/or ultrasound guidance, as noted above. Alternatively, the heart may be approached through an intercostal incision and the delivery device can be positioned or guided within the thoracic cavity. If so desired, the operator may position an endoscope within the thoracic cavity to see the location of the delivery device with respect to the heart.

The tissue-contacting portion of the delivery device may then be brought into surface contact with the tissue surface of the patient's cardiac tissue. For example, the distal face 226 of the catheter assembly 212 (see, e.g., FIG. 18) may be brought into contact with the tissue surface T, as illustrated in FIG. 23b. As illustrated in FIGS. 28–32, however, devices in accordance with other embodiments of the invention employ elongate tissue-contacting areas and merely urging the distal tip of the device against the tissue may not bring the intended tissue-contacting area against the tissue. For example, the body 410 of FIGS. 28A–C may be guided adjacent the heart with the tissue-contacting member 414 deflected (e.g., straightened) from its relaxed state. Once the tissue-contacting member 414 is determined to be in the desired position, the operator may allow the tissue-contacting member 414 to relax and more closely conform to the tissue surface.

If so desired, the agent may be injected into the cardiac tissue without separately confirming appropriate contact between the delivery device and the tissue. In other embodiments of the invention, however, surface contact between the tissue-contacting portion of the delivery device and the cardiac tissue surface is detected before the agent is injected into the tissue. Appropriate surface contact may be detected in any desired fashion. In embodiments of the invention, surface contact may be detected by supplying an excitation voltage to a plurality of electrodes positioned on the tissue-contacting portion of the body and measuring a level of at least one current conducted by the plurality of electrodes, as discussed above.

For example, contact between the distal end probe 130 of FIG. 12A and the tissue surface can be can be detected using the sensors 136, 138, and 140 and monitoring the display (32 in FIG. 1) until appropriate surface contact is indicated on the display. Once appropriate surface contact is detected, the needle 134 can be advanced distally into the tissue (not shown in FIG. 12) and the agent can be injected through the needle 134. If a needleless delivery device such as that shown in FIGS. 28A–C is used, surface contact between the tissue and the tissue-contacting surface 422 can be detected using the sensors 425 and, thereafter, the agent can be injected as a series of jets from the outlet ports 420a–e.

As noted above, some embodiments of the invention well suited for treating atrial fibrillation employ pressurized jets of fluid to inject a tissue-ablating agent into the tissue. Fluid delivery pressures may be on the order of 400 psi or higher, e.g., 600–2,000 psi. By selecting pressure and other operating parameters, the jets may be adapted to penetrate 2 mm or more into the cardiac tissue. In one useful embodiment, the jets are adapted to pass through the entire thickness of the myocardium, creating a relatively focused transmural lesion, as discussed above. In such an embodiment, a quantity of the tissue-ablating agent may pass into the patient's bloodstream (for injection into the heart from an external delivery device) or into the thoracic cavity into contact with other organs or tissue (for injections from outlet ports positioned in the interior of the heart). In such embodiments, it may be advantageous to select a tissue-ablating agent that is effective to damage the cardiac tissue in which it is received, but is not overly deleterious to the patient if it enters the bloodstream, for example. For example, ethanol, hypertonic saline and hot saline may all effectively ablate cardiac tissue to create a transmural lesion, but reasonable excess fluid volumes may be introduced into the patient's bloodstream without significant adverse consequences.

By way of example only, one embodiment that has been found to function acceptably employs five spaced-apart outlet ports with diameters of about 0.004–0.008 inches. Delivering about 1 ml of ethanol at a delivery pressure of about 1000–2000 psi adjacent the outlet ports creates a transmural lesion in atrium walls having a thickness of about 3–8 mm. These operating parameters may be suitable for penetrating entirely through even thicker walls, as well.

As noted above, embodiments of the invention permit physiological properties of a tissue (e.g., EKG) to be measured. If so desired, such a device may be employed to measure the physiological properties of the cardiac tissue on a real-time basis to monitor effect of the tissue-damaging agent on the cardiac tissue, helping ensure that an appropriate cardiac lesion is created. For example, the needle 162 of FIG. 14 may be used both to deliver the agent and to collect EKG data indicative of the state of the tissue adjacent the needle 162. This allows an operator to ensure that a desired tissue effect is achieved before terminating the procedure or moving on to another location for further treatment.

The medical device may have a relatively small tissue-contacting surface delivering tissue to a relatively focused tissue volume (e.g., the distribution plate 364 of the treatment apparatus 330 of FIGS. 27A–B). If so, a lesion of the desired length may require a series of injections at spaced-apart locations along the tissue surface. Repeated repositioning of the device may be reduced, if not eliminated, by employing a device with an elongate tissue-contacting member, such as the embodiments of FIGS. 28–32.

Another embodiment provides a method of treating tissue which involves urging two opposed tissue-contacting members against the tissue. FIGS. 41–45 schematically illustrate selected applications of this embodiment to ablate tissue in treating cardiac arrhythmia. These drawings schematically illustrate a tissue treatment apparatus 600' similar to that shown in FIG. 37A, but with the tissue grasping member 620 replaced with the tissue grasping member 640 shown in FIGS. 39A–B.

Figure 41:
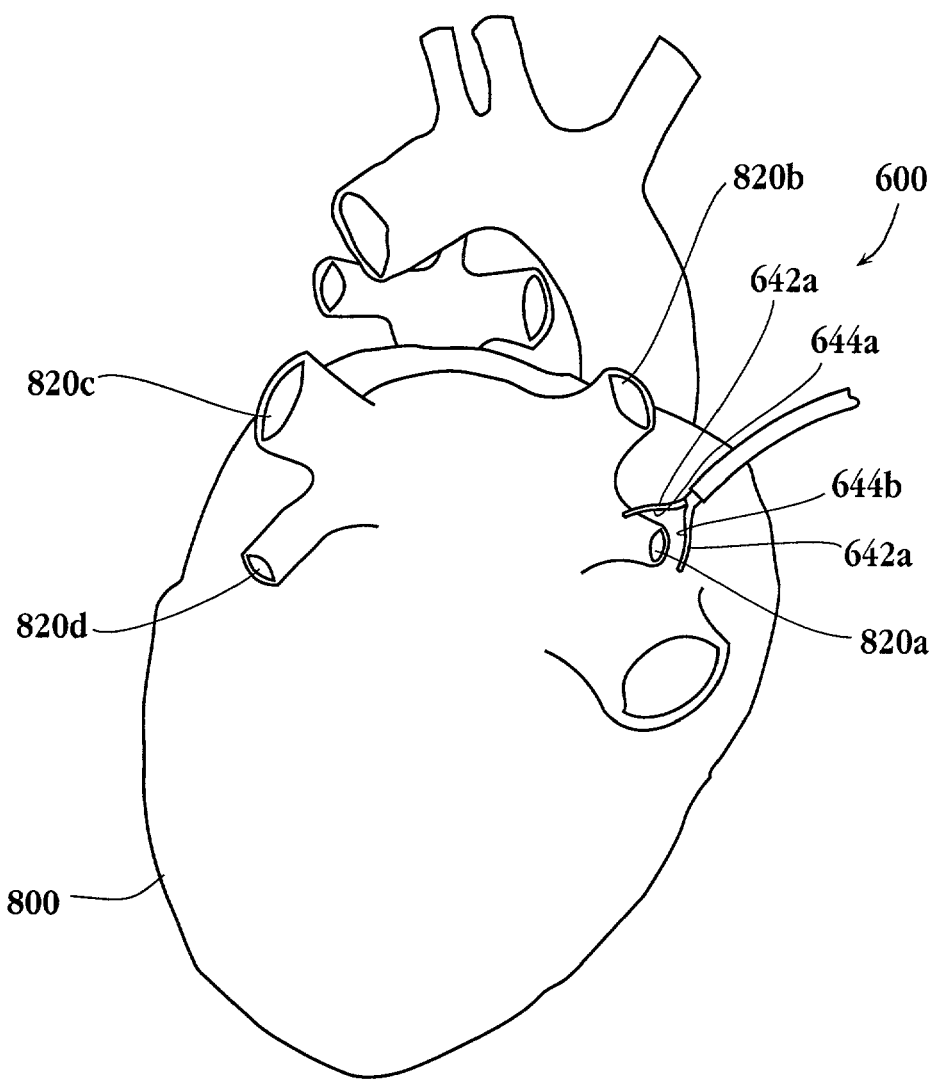
FIG. 41 schematically illustrates positioning of the tissue treatment device of FIG. 33 adjacent to a patient's heart to treat atrial fibrillation.

As shown in FIG. 41, the tissue treatment apparatus 600' may be positioned within a thoracic cavity adjacent the heart 800. The distally positioned tissue grasping member 640 may be guided toward one of the pulmonary veins 820a–d, e.g., pulmonary vein 820a. Positioning the tissue grasping member 640 in an open position, wherein the tissue-contacting members 642 are oriented more away from one another than in the closed position (FIG. 39B), provides an area between the two tissue-contacting members 642 within which the pulmonary vein 820a can be received. With the pulmonary vein 820a received between the tissue-contacting members 642, the tissue-contacting members 642 can be moved toward one another and into engagement with a tissue surface of the pulmonary vein 820a.

Although FIG. 36 schematically illustrates use of the tissue treatment apparatus 500 of FIGS. 33–35, the arrangement of the tissue-contacting members 642 when brought into contact with the pulmonary vein 820a may look much the same in cross-section as the arrangement shown in FIG. 36. In particular, the two tissue-contacting members 642 may contact the target tissue 544 along a plane through the target tissue, which may be thought of as a plane extending between the opposed sets of outlet ports in the fluid delivery conduit 630 (conduits 520a–b are shown in the embodiment of FIG. 36). In a modification of this environment, the tissue-contacting members are instead brought into contact with a target location on the atrium of the heart 800 proximal of the pulmonary vein at a location wherein the pulmonary vein 820a can be electrically isolated from the rest of the heart.

In some embodiments, the tissue-contacting members 642 may be urged against the target tissue (544 in FIG. 36) of the pulmonary vein 820a with sufficient force to deform the pulmonary vein 820a. This will urge segments of the pulmonary vein wall located on opposite sides of the pulmonary vein 820a toward one another. This can effectively grasp a length of the pulmonary vein 820a, holding the target tissue in a relatively stable position for treatment with a treatment fluid, e.g., a tissue-ablating fluid. If so desired, the wall segments may be juxtaposed with respect to one another, yet remain spaced from one another. This permits the blood to continue to flow through the pulmonary vein 820a in a minimally invasive procedure and avoids undue damage to the intima of the pulmonary vein's lumen.

Figure 42:
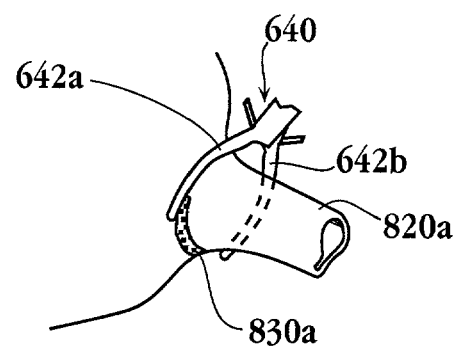
FIG. 42 is a close-up view schematically illustrating a step in a process of forming a lesion around a pulmonary vein.

A treatment fluid may then be delivered through the fluid delivery conduit 630 of the tissue treatment apparatus 600. If the treatment fluid comprises a tissue-ablating fluid, this will simultaneously ablate a line of tissue on each side of the wall of the pulmonary vein 820a to form a transmural lesion along a length of the wall. The length of this lesion will depend on the length of the tissue-contacting members 642 and the positioning of the outlet ports on the fluid delivery conduit 630 carried by the tissue-contacting members 642. FIG. 42 illustrates a lesion 830a that extends only along a portion of the wall of the pulmonary vein 820a.

Figure 43:
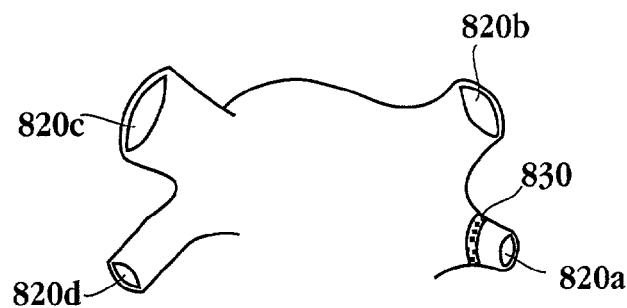
FIG. 43 schematically illustrates the lesion formed in the process illustrated in FIG. 42.

This partial lesion 830 a may be insufficient to effectively electrically isolate the pulmonary vein 820a from the atrium of the heart 800. To better isolate the pulmonary vein 820a, the tissue treatment apparatus 600 may be repositioned so a portion of the pulmonary vein 820a which remains untreated is positioned between the tissue-contacting members 642 of the tissue grasping member 640. A second lesion may be formed in much the same fashion as lesion 830a. This second lesion may adjoin the first lesion 830a to form a longer, effectively continuous lesion. This process can be repeated until the resultant series of lesions forms a relatively continuous lesion 830 that substantially circumscribes the pulmonary vein 820a, as shown in FIG. 43. Each of the four pulmonary veins 820a–d can be treated in much the same fashion to effectively electrically isolate the pulmonary veins 820 from the atrium of the heart 800.

Figure 44:
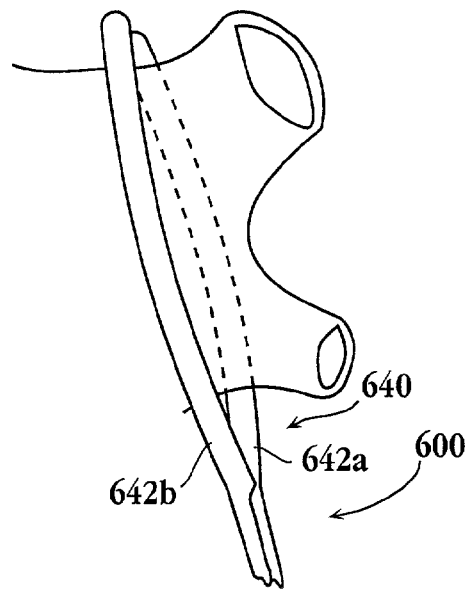
FIG. 44 schematically illustrates positioning of an alternative tissue treatment device with respect to two pulmonary veins.
Figure 45:
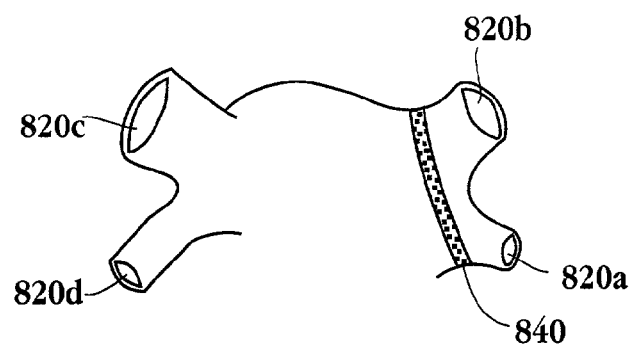
FIG. 45 schematically illustrates the lesion formed in the process illustrated in FIG. 44.

FIGS. 44 and 45 schematically illustrate a slightly different adaptation of this embodiment, wherein a lesion is formed in the atrium to isolate to pulmonary veins 820a–b from the atrium. In the embodiment shown in FIG. 44, much the same distal grasping member 640 of the tissue treatment apparatus 600 is illustrated. In this embodiment, though, the distal grasping member 640 is larger than the distal grasping member shown in FIGS. 41 and 42, permitting a lesion 840 to be formed in a single ablating step rather than requiring a series of separate ablations. As in the embodiment discussed above in connection with FIGS. 41–43, the tissue-contacting members 642 may be urged into contact with the target tissue of the atrium. The opposed inner surfaces of the wall of the atrium may be brought closer together for the urging force of the tissue-contacting members 642 and an ablating fluid may be delivered through the fluid delivery conduit (630 in FIG. 37A) to ablate atrial tissue, creating the lesion 840.

Various embodiments of the invention have been illustrated and described. Many alternatives, modifications and variations not shown or described are within the scope of the invention, and are available to one of ordinary skill in the art.

What is claimed is:

1. A medical device for treating tissue comprising:
   a fluid reservoir;
   a first tissue contacting member adapted to be manipulated into contact with a surface of a target tissue, the first tissue contacting member having a body, first and second tissue-contacting surfaces spaced apart from one another to define a gap therebetween, and a recess proximate to the gap; and
   a first fluid delivery conduit in fluid communication with the reservoir and having a plurality of outlet ports, the first fluid delivery conduit having a length received in the recess, wherein the outlet ports are oriented toward the gap and the first fluid delivery conduit is spaced apart from the plane extending across the gap such that the first fluid delivery conduit does not contact the tissue.

2. The medical device of claim 1 further comprising a second tissue contacting member having a body and a tissue-contacting surface, the second tissue contacting member being operatively associated with the first tissue contacting member to permit movement between an open configuration and a closed configuration, the tissue-contacting surfaces of the first tissue contacting members being oriented generally toward the second tissue contacting member in the closed configuration.

3. The medical device of claim 1 further comprising:
   a second tissue contacting member having a body, first and second tissue-contacting surfaces spaced from one another to define a second gap therebetween, and a second recess proximate to the gap, the second tissue contacting member being operatively associated with the first tissue contacting member to permit movement between an open configuration and a closed configuration, the tissue-contacting surfaces of the first and second tissue contacting members being oriented generally toward one another in the closed configuration; and
   a second fluid delivery conduit in fluid communication with the reservoir and having a plurality of outlet ports, the second fluid delivery conduit having a length received in the second recess with the outlet ports oriented toward, but spaced from, the second gap.

4. The medical device of claim 3 further comprising an elongate body sized to be introduced into a thoracic cavity through an intercostal incision, the first tissue contacting member and the second tissue contacting member being disposed adjacent a distal end of the body, and a manually operable actuator spaced proximally from the distal end of the body and adapted to move the first and second tissue contacting members between the open and closed configurations.

5. The medical device of claim 1 wherein the first tissue contacting member carries a tissue contacting sensor.

6. The medical device of claim 5 wherein the contact sensor comprises a pair of electrodes, one electrode of the pair being carried on the first tissue-contacting surface and the other electrode of the pair being carried on the second tissue-contacting surface.

7. The medical device of claim 1 wherein the ports of the conduit are spaced a distance from a plane extending between the first and second tissue-contacting surfaces.

8. The medical device of claim 1 further comprising a pressure control in fluid communication with the reservoir, the pressure control being operable to establish an elevated pressure within the fluid delivery conduit sufficient to propel a fluid in the fluid reservoir through the outlet ports to define a plurality of spaced-apart fluid jets capable of penetrating a target tissue to a gap of at least about 2 mm.

9. The medical device of claim 8 wherein the pressure control is operable to establish an elevated delivery pressure of about 600–2000 psi.

10. The medical device of claim 8 wherein the pressure control is operable to define the fluid jets capable of penetrating an entire thickness of a patient's myocardium.

11. The medical device of claim 1 further comprising a tissue-ablating agent in the reservoir, the tissue-ablating agent comprising a fluid selected from the group consisting of alcohols, hypertonic saline, hot saline, hot glycerine, hot ethylene glycol, cold saline, cold glycerine, cold ethylene glycol, sodium tetradecyl sulfate, and polyethyleneglycol-monododecylether.

12. A medical device for treating tissue comprising:
a fluid reservoir;
a tissue grasping member comprising a first tissue contacting member and an opposed second tissue contacting member, the first and second tissue contacting members being operatively associated with one another and movable between a first configuration wherein they have a first relative orientation adapted to receive the tissue therebetween and a second configuration wherein they have a second relative orientation adapted to grasp the tissue therebetween; wherein the first and second tissue contacting members each have first and second tissue contacting surfaces spaced apart from one another to define a gap therebetween, and
first and second fluid delivery conduits in fluid communication with the reservoir, the first fluid delivery conduit having a distal length carried by the first tissue contacting member and a plurality of outlet ports spaced along that distal length, and the second fluid delivery conduit having a distal length carried by the second tissue contacting member and a plurality of outlet ports spaced along that distal length, the outlet ports of the first and second fluid delivery conduits being oriented generally inwardly toward one another when the tissue grasping member is in the second configuration, wherein the first and second delivery conduits are spaced apart from the planes extending across the gaps such that the first and second delivery conduits do not contact the tissue.

13. The medical device of claim 12 wherein the tissue grasping member carries a tissue contact sensor.

14. The medical device of claim 13 wherein the tissue contact sensor comprises a pair of electrodes.

15. The medical device of claim 12 wherein the first tissue contacting member includes an elongate first recess within which the distal length of the first fluid delivery conduit is received and the second tissue contacting member includes an elongate second recess within which the distal length of the second fluid delivery conduit is received.

16. The medical device of claim 15 wherein the first tissue contacting member has a first tissue-contacting face having a first gap therein, the outlet ports of the first fluid delivery conduit being oriented toward, but spaced from, the first gap, and the second tissue contacting member has a second tissue contacting face having a second gap therein, the outlet ports of the second fluid delivery conduit being oriented toward, but spaced from, the second gap.

17. A medical device for treating cardiac arrhythmia, comprising:
a fluid reservoir for receiving an injectable tissue-ablating agent;
an elongate body adapted for introduction into a thoracic cavity, the body having a distal tissue-contacting member having first and second tissue contacting surfaces spaced apart from one another to define a gap therebetween,
a first fluid delivery conduit in communication with the fluid reservoir having a plurality of outlet ports, wherein the first fluid delivery conduit is spaced apart from the plane extending across the gap such that the first fluid delivery conduit does not contact a desired tissue;
a lumen in the body communicating the reservoir with the outlet ports;
a pressure control in fluid communication with the reservoir, the pressure control being operable to establish an elevated pressure within the lumen sufficient to propel the tissue-ablating agent from the fluid supply through the outlet ports to define a plurality of spaced-apart fluid jets capable of penetrating the target tissue to a depth of at least about 2 mm.

18. The medical device of claim 17 wherein the pressure control is operable to establish an elevated delivery pressure of at least about 400 psi.

19. The medical device of claim 17 wherein the pressure control is operable to establish an elevated delivery pressure of about 600–2000 psi.

20. The medical device of claim 17 wherein the pressure control is operable to define the fluid jets capable of penetrating an entire thickness of a patient's myocardium.

21. The medical device of claim 17 wherein the tissue-contacting member includes a tissue contact sensor.

22. The medical device of claim 21 wherein the tissue contact sensor is operatively coupled to an EKG display.

23. The medical device of claim 21 wherein the tissue contact sensor comprises at least two electrodes spaced from one another along a tissue-contacting surface of the tissue-contacting member of the body.

24. The medical device of claim 23 wherein the electrodes are operatively coupled to an EKG display.

25. The medical device of claim 17 wherein the tissue-contacting member is flexible and adapted to conform to a surface of a target tissue.

26. The medical device of claim 25 wherein the tissue-contacting member has a predetermined curvature in a natural, relaxed state and tends to resiliently return toward the relaxed state when conforming to the surface of the target tissue.

27. The medical device of claim 25 wherein a proximal length of the body is flexible.

28. The medical device of claim 17 wherein the plurality of ports comprises a series of ports aligned along a tissue-contacting surface of the tissue-contacting member of the body.

29. The medical device of claim 17 further comprising a tissue-ablating agent in the reservoir, the tissue-ablating agent comprising a fluid selected from the group consisting of alcohols, hypertonic saline, hot saline, hot glycerine, hot ethylene glycol, cold saline, cold glycerine, cold ethylene glycol, sodium tetradecyl sulfate, and polyethyleneglycol-monododecylether.

30. The medical device of claim 17 further comprising a tissue-ablating agent in the reservoir, the tissue-ablating agent comprising a fluid selected from the group consisting of ethanol, hypertonic saline, hot saline, hot glycerine, hot ethylene glycol, cold saline, cold glycerine, and cold ethylene glycol.

31. The medical device of claim 17 further comprising a tissue-ablating agent in the reservoir, the tissue-ablating agent being selected to damage tissue into which it is injected, yet permit introduction of excess tissue-ablating agent into the patient's bloodstream.

32. The medical device of claim 31 wherein the tissue-ablating agent comprises a fluid selected from the group consisting of ethanol, hypertonic saline, hot saline, hot glycerine, hot ethylene glycol, cold saline, cold glycerine, and cold ethylene glycol.

* * * * *